US009636433B2

(12) United States Patent
Iram et al.

(10) Patent No.: US 9,636,433 B2
(45) Date of Patent: *May 2, 2017

(54) GELATIN-TRANSGLUTAMINASE HEMOSTATIC DRESSINGS AND SEALANTS

(71) Applicant: LifeBond Ltd., Caesarea (IL)

(72) Inventors: Natalie Iram, Tel Aviv-Jaffa (IL); Orahn Preiss-Bloom, Zichron Yakov (IL); Ishay Attar, Haifa (IL)

(73) Assignee: LIFEBOND LTD, Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,316

(22) Filed: Feb. 17, 2015

(65) Prior Publication Data

US 2015/0196683 A1 Jul. 16, 2015

Related U.S. Application Data

(63) Continuation of application No. 12/519,167, filed as application No. PCT/US2007/025726 on Dec. 17, 2007, now Pat. No. 9,017,664.

(60) Provisional application No. 61/000,887, filed on Oct. 30, 2007, provisional application No. 60/875,150, filed on Dec. 15, 2006.

(51) Int. Cl.
*A61L 15/32* (2006.01)
*A61L 15/38* (2006.01)
*A61L 15/42* (2006.01)
*A61L 15/58* (2006.01)
*A61L 24/04* (2006.01)
*A61L 24/10* (2006.01)
*A61L 26/00* (2006.01)

(52) U.S. Cl.
CPC ............... *A61L 15/38* (2013.01); *A61L 15/32* (2013.01); *A61L 15/325* (2013.01); *A61L 15/42* (2013.01); *A61L 15/585* (2013.01); *A61L 24/043* (2013.01); *A61L 24/104* (2013.01); *A61L 26/0038* (2013.01); *A61L 26/0047* (2013.01); *A61L 26/0052* (2013.01); *A61L 26/0061* (2013.01); *A61L 2400/04* (2013.01)

(58) Field of Classification Search
CPC ...... A61L 2400/04; A61L 17/08; A61L 24/08; A61L 24/10; A61L 27/20; A61L 27/22; A61L 15/32; A61L 15/325; A61L 15/38; A61L 15/42; A61L 15/585; A61L 24/043; A61L 24/104; A61L 26/0038; A61L 26/0047; A61L 15/425; A61L 31/045; A61L 31/047; A61L 31/14; A61L 15/24; A61L 15/26; A61L 26/0014; A61L 26/0019; A61L 24/04; C08L 29/04; C08L 71/02; C08L 89/06

See application file for complete search history.

(56) References Cited

U.S. PATENT DOCUMENTS

| | | |
|---|---|---|
| 1,394,654 A | 10/1921 | Tressler |
| 1,844,679 A | 2/1932 | Price |
| 1,873,580 A | 8/1932 | Hailwood |
| 1,950,483 A | 5/1934 | Christopher et al. |
| 2,048,499 A | 7/1936 | Gellednien |
| 2,126,305 A | 8/1938 | Babcock |
| 2,166,074 A | 7/1939 | Reichel |
| 2,398,004 A | 5/1946 | Houck et al. |
| 2,417,713 A | 3/1947 | Oswald Stein |
| 2,558,065 A | 6/1951 | Tice |
| 2,658,001 A | 11/1953 | Young |
| 2,719,145 A | 9/1955 | Skelton et al. |
| 2,803,548 A | 8/1957 | Hagetry |
| 3,220,845 A | 11/1965 | Fort Lee |
| 3,600,482 A | 8/1971 | Salyer et al. |
| 3,939,001 A | 2/1976 | Clausi et al. |
| 3,988,479 A | 10/1976 | Stephan |
| 4,188,373 A | 2/1980 | Krezanoski |
| 4,188,465 A | 2/1980 | Schneider et al. |
| 4,224,348 A | 9/1980 | Hayashi |
| 4,344,181 A | 8/1982 | Baecklund |
| 4,426,443 A | 1/1984 | Shank |
| 4,478,822 A | 10/1984 | Haslam |
| 4,527,906 A | 7/1985 | Jezbera |
| 4,572,906 A | 2/1986 | Sparkes et al. |
| 4,605,513 A | 8/1986 | DiMarchi |
| 4,651,725 A | 3/1987 | Kifune |
| 4,711,848 A | 12/1987 | Insley |
| 4,729,897 A | 3/1988 | Poppe |
| 4,837,379 A | 6/1989 | Weinberg |

(Continued)

FOREIGN PATENT DOCUMENTS

| | | |
|---|---|---|
| EP | 0073908 A1 | 3/1983 |
| EP | 0302953 | 2/1989 |

(Continued)

OTHER PUBLICATIONS

Examination Report for EP2133069 mailed Apr. 4, 2013.
Biomacromolecules, 2004, vol. 5, No. 4, p. 1270-1279.
De Carvalhoet al,; 1997; Physical gelation under shear for gelatin gels. Rheologica Acta 36(6): 591-609.
Examination Report for EP2303344 mailed Jun. 11, 2013.
Examination Report for EP2515957 mailed Jun. 24, 2013.
Extended Search report for EP2586467 mailed Jun. 17, 2013.
Journal of Biomedical Materials Research. Part B, Applied Biomaterials., 2006, 5, vol. 77, No. 2, p. 416-422.

(Continued)

*Primary Examiner* — Debbie K Ware
(74) *Attorney, Agent, or Firm* — Graeser Associates International Inc; Dvorah Graeser

(57) ABSTRACT

An adhesive material for medical use comprising gelatin and a non-toxic cross-linking material such as transglutaminase. An optional embodiment of the invention includes dressings in which a layer of a transglutaminase is sandwiched between a first and second layer of gelatin. The hemostatic products are useful for the treatment of wounded tissue.

12 Claims, 15 Drawing Sheets

(56) References Cited

U.S. PATENT DOCUMENTS

| | | |
|---|---|---|
| 4,891,319 A | 1/1990 | Roser |
| 4,931,501 A | 6/1990 | Lai et al. |
| 4,948,540 A | 8/1990 | Nigam |
| 4,952,618 A | 8/1990 | Olsen |
| 4,985,250 A | 1/1991 | Bee et al. |
| 5,015,677 A | 5/1991 | Benedict et al. |
| 5,059,636 A | 10/1991 | Grenga |
| 5,147,344 A | 9/1992 | Sachau |
| 5,209,776 A | 5/1993 | Bass et al. |
| 5,399,361 A | 3/1995 | Song |
| 5,428,014 A | 6/1995 | Labroo et al. |
| 5,433,943 A | 7/1995 | Osipow |
| 5,441,193 A | 8/1995 | Gravener |
| 5,480,644 A | 1/1996 | Freed |
| 5,487,889 A | 1/1996 | Eckert et al. |
| 5,487,895 A | 1/1996 | Dapper |
| 5,490,984 A | 2/1996 | Freed |
| 5,503,638 A | 4/1996 | Cooper et al. |
| 5,508,202 A | 4/1996 | Enomoto |
| 5,525,335 A | 6/1996 | Kitahara et al. |
| 5,549,628 A | 8/1996 | Cooper et al. |
| 5,549,904 A | 8/1996 | Juergensen et al. |
| 5,575,803 A | 11/1996 | Cooper et al. |
| 5,618,312 A | 4/1997 | Yui |
| 5,702,409 A | 12/1997 | Rayburn et al. |
| 5,736,132 A | 4/1998 | Juergensen et al. |
| 5,752,965 A | 5/1998 | Francis et al. |
| 5,752,974 A | 5/1998 | Rhee et al. |
| 5,810,855 A | 9/1998 | Rayburn et al. |
| 5,834,232 A | 11/1998 | Bishop et al. |
| 5,895,412 A | 4/1999 | Tucker |
| 5,931,165 A | 8/1999 | Reich et al. |
| 5,939,385 A | 8/1999 | Labroo et al. |
| 5,948,662 A | 9/1999 | Kobayashi et al. |
| 6,007,613 A | 12/1999 | Izoret |
| 6,030,821 A | 2/2000 | Soeda |
| 6,054,122 A | 4/2000 | MacPhee et al. |
| 6,063,061 A | 5/2000 | Wallace et al. |
| 6,066,325 A | 5/2000 | Wallace |
| 6,083,524 A | 7/2000 | Sawhney |
| 6,100,053 A | 8/2000 | Bech et al. |
| 6,107,401 A | 8/2000 | Dado et al. |
| 6,117,425 A | 9/2000 | MacPhee et al. |
| 6,121,013 A | 9/2000 | Yamaguchi |
| 6,132,759 A | 10/2000 | Schacht et al. |
| 6,136,341 A | 10/2000 | Petito et al. |
| 6,156,330 A | 12/2000 | Tsukada |
| 6,162,241 A | 12/2000 | Coury et al. |
| 6,190,896 B1 | 2/2001 | Fraij |
| 6,197,325 B1 | 3/2001 | MacPhee et al. |
| 6,228,393 B1 | 5/2001 | DiCosmo |
| 6,267,957 B1 | 7/2001 | Green et al. |
| 6,303,752 B1 | 10/2001 | Olsen |
| 6,371,975 B2 | 4/2002 | Cruise et al. |
| 6,413,742 B1 | 7/2002 | Olsen et al. |
| 6,420,148 B2 | 7/2002 | Yamaguchi |
| 6,454,787 B1 | 9/2002 | Maddalo |
| 6,458,386 B1 | 10/2002 | Schacht |
| 6,465,001 B1 | 10/2002 | Hubbell |
| 6,475,516 B2 | 11/2002 | DiCosmo |
| 6,509,039 B1 | 1/2003 | Nies |
| 6,527,751 B2 | 3/2003 | Fischer et al. |
| 6,531,147 B2 | 3/2003 | Sawhney |
| 6,544,227 B2 | 4/2003 | Sahatjian et al. |
| 6,559,119 B1 | 5/2003 | Burgess et al. |
| 6,576,685 B2 | 6/2003 | Stedreonsky |
| 6,605,066 B1 | 8/2003 | Gravagna et al. |
| 6,610,043 B1 | 8/2003 | Ingenito |
| 6,656,193 B2 | 12/2003 | Grant et al. |
| 6,663,594 B2 | 12/2003 | Sahatjian |
| 6,682,760 B2 | 1/2004 | Noff |
| 6,704,210 B1 | 3/2004 | Myers |
| 6,706,690 B2 | 3/2004 | Reich |
| 6,762,336 B1 | 7/2004 | MacPhee et al. |
| 6,773,156 B2 | 8/2004 | Henning |
| 6,833,258 B2 | 12/2004 | Yokoyama et al. |
| 6,863,783 B2 | 3/2005 | Lin |
| 6,875,796 B2 | 4/2005 | Stredronsky |
| 6,939,358 B2 | 9/2005 | Palacios et al. |
| 6,992,172 B1 | 1/2006 | Chang et al. |
| 7,019,191 B2 | 3/2006 | Looney et al. |
| 7,045,601 B2 | 5/2006 | Metzner |
| 7,074,981 B2 | 7/2006 | Chalmers |
| 7,108,876 B2 | 9/2006 | Grindstaff |
| 7,109,163 B2 | 9/2006 | Pendharkar |
| 7,129,210 B2 | 10/2006 | Lowinger |
| 7,186,684 B2 | 3/2007 | Pendharkar |
| 7,189,410 B1 | 3/2007 | Drohan et al. |
| 7,196,054 B1 | 3/2007 | Drohan et al. |
| 7,208,171 B2 | 4/2007 | Messersmith et al. |
| 7,208,179 B1 | 4/2007 | Drohan et al. |
| 7,229,959 B1 | 6/2007 | Drohan et al. |
| 7,241,730 B2 | 7/2007 | Hubbell |
| 7,285,580 B2 | 10/2007 | Stedronsky |
| 7,320,962 B2 | 1/2008 | Reich |
| 7,435,425 B2 | 10/2008 | Qian |
| 7,459,425 B2 | 12/2008 | Wan et al. |
| 7,468,350 B2 | 12/2008 | Gong |
| 7,766,891 B2 | 8/2010 | McGurk |
| 7,998,466 B2 | 8/2011 | Hadba |
| 8,133,484 B2 | 3/2012 | Preiss-Bloom et al. |
| 8,367,388 B2 | 2/2013 | Bloom et al. |
| 8,722,039 B2 * | 5/2014 | Preiss-Bloom ........ A61L 15/325 424/443 |
| 9,066,991 B2 * | 6/2015 | Preiss-Bloom .......... A61L 24/08 |
| 9,297,464 B1 * | 3/2016 | Wang ..................... F16K 15/20 |
| 2001/0018598 A1 | 8/2001 | Cruise |
| 2002/0015724 A1 | 2/2002 | Yang |
| 2003/0008831 A1 | 1/2003 | Yang |
| 2003/0035786 A1 | 2/2003 | Hendriks |
| 2003/0120284 A1 | 6/2003 | Palacios et al. |
| 2003/0135238 A1 | 7/2003 | Milbocker |
| 2003/0219857 A1 | 11/2003 | Chou |
| 2003/0232944 A1 | 12/2003 | Molenberg |
| 2004/0093029 A1 | 5/2004 | Zubik et al. |
| 2004/0106344 A1 | 6/2004 | Looney |
| 2004/0131728 A1 | 7/2004 | Ootzuka et al. |
| 2005/0113937 A1 | 5/2005 | Binette et al. |
| 2005/0129733 A1 | 6/2005 | Milbocker |
| 2005/0147646 A1 | 7/2005 | Nilsson |
| 2005/0209441 A1 | 9/2005 | Lile |
| 2005/0238683 A1 | 10/2005 | Adhikari et al. |
| 2005/0249839 A1 | 11/2005 | Ishida |
| 2005/0271727 A1 | 12/2005 | Yao |
| 2006/0078962 A1 | 4/2006 | Chen et al. |
| 2006/0100138 A1 | 5/2006 | Olsen |
| 2006/0155234 A1 | 7/2006 | MacPhee et al. |
| 2006/0258560 A1 | 11/2006 | Yang et al. |
| 2006/0269590 A1 | 11/2006 | Trotter et al. |
| 2007/0021703 A1 | 1/2007 | McCarthy |
| 2007/0082023 A1 | 4/2007 | Hopman et al. |
| 2007/0128152 A1 | 6/2007 | Hadba |
| 2007/0172432 A1 | 7/2007 | Stopek |
| 2007/0246505 A1 | 10/2007 | Pace-Florida et al. |
| 2008/0187591 A1 | 8/2008 | Rhee et al. |
| 2008/0195037 A1 | 8/2008 | Hissong |
| 2008/0213243 A1 | 9/2008 | Preiss-Bloom |
| 2008/0260801 A1 | 10/2008 | Ahlers |
| 2008/0286376 A1 | 11/2008 | Qian et al. |
| 2009/0175946 A1 | 7/2009 | Gaissmaier et al. |
| 2009/0191269 A1 | 7/2009 | Gaissmaier |
| 2010/0008989 A1 | 1/2010 | Attar |

FOREIGN PATENT DOCUMENTS

| | | |
|---|---|---|
| EP | 0707474 | 4/1996 |
| EP | 0726317 | 8/1996 |
| EP | 0745670 | 12/1996 |
| EP | 0777726 | 6/1997 |
| EP | 0815742 | 1/1998 |
| EP | 0871712 | 10/1998 |
| EP | 0876166 | 11/1998 |
| EP | 0927053 | 7/1999 |
| EP | 0947142 | 10/1999 |

(56) References Cited

FOREIGN PATENT DOCUMENTS

| | | |
|---|---|---|
| EP | 0982038 | 3/2000 |
| EP | 1124590 | 8/2001 |
| EP | 1263327 | 12/2002 |
| EP | 1267826 | 1/2003 |
| EP | 1267876 | 1/2003 |
| EP | 1288264 | 3/2003 |
| EP | 1372492 | 1/2004 |
| EP | 20030744835 | 1/2005 |
| EP | 1574229 | 9/2005 |
| EP | 1857494 | 11/2007 |
| EP | 1948260 | 7/2008 |
| EP | 2133069 | 12/2009 |
| JP | 2204407 | 8/1990 |
| JP | 2255888 | 10/1990 |
| JP | 7328108 | 12/1995 |
| JP | 10510183 | 10/1998 |
| JP | 2002515300 A | 5/2002 |
| JP | 2004283371 A | 10/2004 |
| JP | 2006503612 A | 2/2006 |
| JP | 07227228 | 9/2007 |
| WO | WO96017929 | 6/1996 |
| WO | WO9640791 | 12/1996 |
| WO | WO9722372 | 6/1997 |
| WO | 9729715 A2 | 8/1997 |
| WO | WO9729715 | 8/1997 |
| WO | 9737694 A1 | 10/1997 |
| WO | WO9740701 | 11/1997 |
| WO | WO9741899 | 11/1997 |
| WO | WO/98/35026 | 8/1998 |
| WO | WO/00/22103 | 4/2000 |
| WO | WO/00/76533 | 12/2000 |
| WO | WO/01/15750 | 3/2001 |
| WO | 02085422 | 10/2002 |
| WO | 02098937 A2 | 12/2002 |
| WO | WO/03/011352 | 2/2003 |
| WO | WO/03/072155 | 9/2003 |
| WO | WO/03/072157 | 9/2003 |
| WO | WO03074004 | 9/2003 |
| WO | WO03080144 | 10/2003 |
| WO | WO03086493 | 10/2003 |
| WO | WO2004004875 | 1/2004 |
| WO | WO/2004/014969 | 2/2004 |
| WO | 20040024195 A1 | 3/2004 |
| WO | WO/2004/029096 | 4/2004 |
| WO | WO2004028404 | 4/2004 |
| WO | WO/2004/098671 | 11/2004 |
| WO | WO/2004/105485 | 12/2004 |
| WO | WO/2005/061701 | 7/2005 |
| WO | WO/2006/014567 | 2/2006 |
| WO | WO/2006/014568 | 2/2006 |
| WO | WO2006016809 | 2/2006 |
| WO | WO2006027622 | 3/2006 |
| WO | WO2006056700 | 6/2006 |
| WO | 2006086479 A1 | 8/2006 |
| WO | WO/2006/134148 | 12/2006 |
| WO | WO2006128685 | 12/2006 |
| WO | 2007008229 | 1/2007 |
| WO | WO/2008/006545 | 1/2007 |
| WO | 20070057175 A2 | 5/2007 |
| WO | WO2007057175 | 5/2007 |
| WO | WO/2007/122232 | 11/2007 |
| WO | WO/2007/123350 | 11/2007 |
| WO | WO/2007/126411 | 11/2007 |
| WO | WO/2007/134118 | 11/2007 |
| WO | WO2008006544 | 1/2008 |
| WO | WO2008006545 | 1/2008 |
| WO | WO/2008/016983 | 2/2008 |
| WO | 20080076407 A2 | 6/2008 |
| WO | WO/2008/073938 | 6/2008 |
| WO | WO2008076407 | 6/2008 |
| WO | WO/2008/103891 | 8/2008 |
| WO | WO/2009/012882 | 1/2009 |
| WO | WO/2009/026158 | 2/2009 |
| WO | WO/2009/036014 | 3/2009 |
| WO | WO/2009/073193 | 6/2009 |
| WO | WO/2009/105614 | 8/2009 |
| WO | 2009153750 A2 | 12/2009 |
| WO | 2009153751 A2 | 12/2009 |
| WO | 20090153748 A2 | 12/2009 |
| WO | WO/2010/027471 | 3/2010 |

OTHER PUBLICATIONS

Kwon, j. 2010; Rheological Behaviour of Gelatin at High Shear Rates. Ph.D Dissertation—University of Florida pp. 1-100. specif. pp. 27-28, 46.
Office Action for CA 2,728,187 mailed Apr. 2, 2013.
Office Action for CN 102124058 A mailed May 9, 2013.
Office Action for CN 101854960 A mailed Apr. 3, 2013.
Office Action for JP 2011-525128 mailed Aug. 6, 2013.
Office Action for JP2011-267107 mailed Jul. 23, 2013.
Orthodontics and Craniofacial Research, 2005, vol. 8, No. 3, p. 145-149.
Viscosity. Encyclopedia entry (online). Wikipedia, the free encyclopedia. "Dynamic Viscosity", p. 6 line 10; "Liquids", p. 9 line 7-8 [URL: http://en.wikipedia.org/wiki/viscosity]; no date specified.
Search report issued for corresponding PCT Application No. PCT/IB2011/053505, mailed Mar. 9, 2012.
Search report issued for corresponding PCT Application No. PCT/IB2011/051714, mailed Nov. 30, 2011.
Drury et al, "Hydrogels for tissue engineering: scaffold design variables and applications", Biomaterials, vol. 24, Nov. 2003, pp. 4337-4351.
Search report issued for corresponding PCT Application No. PCT/IB2010/056008, mailed Apr. 19, 2011.
Office action issued for corresponding European Application No. 12155067, mailed Jul. 3, 2012.
Wichman et al, "Kinetics of Refolding of Completely Reduced Human-Serum Albumin", European Journal of Biochemistry, vol. 79, 1977, pp. 339-344.
Office action issued for corresponding European Application No. 9766288.6, mailed Jun. 6, 2012.
Office action issued for corresponding European Application No. 9766287.8, mailed Mar. 12, 2013.
Office action issued for corresponding Chinese Application No. 200980131973.6, mailed Sep. 24, 2012.
Office action issued for corresponding European Application No. 7867783.8, mailed Jun. 27, 2012.
Office action issued for corresponding Japanese Application No. 2009-541417, mailed Jan. 8, 2013.
Office action issued for corresponding Australian Application No. 2007334394, mailed Jan. 4, 2013.
Office action issued for corresponding Canadian Application No. 2672651, mailed Feb. 1, 2013.
Office action issued for corresponding Chinese Application No. 200780051215.4, mailed Aug. 31, 2012.
Office action issued for corresponding European Application No. 12187110, mailed Nov. 21, 2012.
Examination report for corresponding Australian Application No. 2007334394, mailed Jul. 20, 2012.
Fernandez-Diaz, M.D. et al., "Gel Properties of Collagens from Skins of Cod (*Gadus morhua*) and Hake (*Merluccius merluccius*) and Their Modification by the Coenhancers Magnesium sulphate, Glycerol and Transglutaminase", Food Chemistry, 2001, vol. 74, pp. 161-167.
Nio et al. Gelation Mechanismof Protein Solution by Transglutaminase; Agricultural and Biol Chem 50(4), 1986: p. 851-855.
O'Halloran DM et al. Characterization of a microbial transglutaminase cross-linked type II collagen scaffold. Tissue Eng. Jun. 2006; 12(6): 1467-74.
Ohtake Y et al. Transglutaminase catalyzed dissociation and association of protein-polyamine complex; Life Sciences 2007; 81 ,7: p. 577-584.
Otani Y et al. Sealing Effect of Rapidly Curable Gelatin-Poly (L-Glutamic Acid) Hydrogel Glue on Lung Air Leak; Ann Thorac Surg 1999, 67, 922-6.

(56) References Cited

OTHER PUBLICATIONS

Rodriguez et al. Combined effect of plasticizers and surfactants on the physical properties of starch based edible films; Food Research International 39 (2006) 840-6.
Sanbom TJ et al. In situ crosslinking of a biomimetic peptide-PEGhydrogel via thermally triggered activation of factor XIII; Biomaterials 2002, 23, 2703-10.
Serafinie-Fracassini D et al. First Evidence for Polyamine Conjugation Mediated by an Enzymic Activity in Plants; Plant Physiol. (1988) 87, 757-761.
Shojaei AM et al. Mechanisms of buccal mucoadhesion of novel copolymers of acrylic acid and polyethylene glycol monomethylether monomethacrylate; Journal of Control Release, 1997, 47, 151-61.27.
Silva EA et al. Spatiotemporal control of vascular endothelial growth factor delivery from injectable hydrogels enhances angiogenesis; J Thromb Haemost 2007, 5, 590-8.
Silverman HG et al. Understanding Marine Mussel Adhesion; Mar Biotechnol (NY) 2007, 9, 661-81.
Sperinde J et al. Control and Prediction of Gelation Kinetics in Enzymatically Cross-Linked Poly(ethylene glycol) Hydrogels; Macromolecules 2000, 33, 5476-5480.
Strausberg RL et al, Protein-based medical adhesives, Trends Biotechnol 1990;8:53-5.
Sung HW et al. Evaluation of gelatin hydrogel crosslinked with various crosslinking agents as bioadhesives: In vitro study; J Biomed Mater Res 1999, 46, 520-30.
Ulijn RV et al. Designing peptide based nanomaterials; Chem Soc Rev 2008, 37, 664-75.
Hideraka Nagatomo, Gelatin-based adhesive has fibrin sealant benefit without use of blood products. Biosci, Biotechnol. Biochem, 2005, 128-136, 69 (1).
Blood Weekly Editors. Gelatin-based adhesive has fibrin sealant benefit without use of blood products, Copyright 2004, Blood Weekly via NewsRx.com.
Office Action for EP patent application 07867783.8 dated: Aug. 28, 2011.
Cui L, et al. Purification and characterization of transglutaminase from a newly isolated Streptomyces hygroscopicus. 2007: 105(2). p. 612-618.
D'Cruz NM, et al. Thermal Unfolding of Gelatin in Solids as Affected by the Glass Transition, J Food Science 2005: 70 (2), Kozlov PV, Burdygina GI.
Search Report for EP patent application 09162590.5 dated: Sep. 2, 2009.
Bello J, et al. Mechanism of Gelation of Gelatin. Influence of Certain Electrolytes on the Melting Points of Gels of Gelatin and Chemically Modified Gelatins. Am Chem Soc. Sep. 1956 (60). p. 1299-1306.
Crowe LM,et al. Is Trehalose Special for Preserving Dry Biomaterials? Biophysical Journal 1996 (71): 2087-2093.
Norie N, et al. Factors Affecting the Gelation of a Gelatin Solution in the Presence of Sugar. Journal of Home Economics of Japan. 55(2): p. 159-166 (2004).
J.M. Rocko et al. (1982). J. Trauma 22:635.
OA for EP patent application 09162590.5 dated: Jul. 6, 2010.
D.B. Kendrick, Blood Program in WW II ( Washington, DC: Office of the Surgeon General, Department of Army; 1989), 363-368.
OA for EP patent application 07867783.8 dated: Jan. 28, 2010.
Gorman, J.J; J Bio. Chem. 1980, 255, 419-427.
Kahlem, P.; Acad. Sci U.S.A. 1996, 93, 14580-14585.
Etoh, Y.; Biochem, Biophys. Res Commun. 1986, 136, 51-56.
Hohenadi, C.; J. Biol. Chem. 1955, 270, 23415-23420.
Gross, M.; J. Biol. Chem. 1975, 250, 4648-4655.
Groenen, P.; Eur. J. Biochem. 1994, 220, 795-799.
Grootjans, J. J. Biol. Chem. 1995, 270, 22855-22858.
Owen et al. N. Engl. J. Med. 309:694-698, 1983.
OA for IL patent application 199357 dated: Mar. 20, 2011.
International Search Report for PCT/IB2009/052600.
International Search Report for PCT/IB2009/052605.
International Search Report for PCT/IB2009/052607.
EP Application 09766288.6 Office Action dated Jun. 6, 2012.
Acheson EM, Kheirabadi BS, Deguzman R, Dick EJ, Holcomb JB. Journal of Trauma-Injury Infection and Critical Care 2005, 59, 865-874.
Balakrishnan et al. (2005). Biomaterials. 26(32):6335-42.
Bertoni F et al. Transglutaminase reactivity with gelatine: perspective applications in tissue engineering; Biotechnol Lett (2006) 28:697-702.
Broderick EP, J Biomed Mater Res B Appl Biomater. Jan. 15, 2005;72(1):37-42.
Chen et al, "Enzyme-catalyzed gel formation of gelatin and chitosan: potential for in situ applications", Biomaterials vol. 24 (2003) pp. 2831-2841.
Chen et al, "Gelatin-Based Biomimetic Tissue Adhesive. Potential for Retinal Reattachment", Published online Nov. 8, 2005 in Wiley InterScience.
Chen et al., Biomacromolecules. 2003; 4 (6):1558-63.
Crescenzi et al, Biomacromolecules 2002, 3, 1384-1391.
Folk JE, Cole PW. Transglutaminase: mechanistic features of the active site as determined by kinetic and inhibitor studies. Biochim Biophys Acta. 1966; 122:244-64.
Garza J. L. et al. (1990). J. Trauma. 30:512-513.
Haug IJ, Draget KI, Smidsrød O. (2004). Food Hydrocolloids. 18:203-213.
HemCon™ bandage (HemCon, Portland, OR) document.
Holcomb, J. B., et al. (1997). Surgical Clinics of North America. 77:943-952).
Ito A, J Biosci & Bioeng. 2003; 95(2): 196-99.
Jackson, M., et al. (1996). J. of Surg. Res. 60:15-22.
Jackson, M., et al. (1997). Surg. Forum. XL, VIII:770-772.
Jakob H. et al. (1984). J. Vasc. Surg. 1:171-180.
Japanese Application 2011-514184 Office Action.
Kheirabadi BS et al. Journal of Trauma-Injury Infection and Critical Care 2005, 59, 25-34.
Kram H. B. et al. (1990). J. Trauma. 30:97-101.
Matthew T. L. et al. (1990). Ann. Thorac. Surg. 50:40-44.
McDermott et al, "Mechanical Properties of Biomimetic Tissue Adhesive Based on the Microbial Transglutaminase-Catalyzed Crosslinking of Gelatin", Biomacromolecules 2004, vol. 5, pp. 1270-1279.
Tucci MG. (2001). J. Bioactive & Comp. Polymers. 16(2): 145-157.
Nomura et al, "Improvement of Shark Type I Collagen with Microbial Transglutaminase in Urea", Biosci. Biotech. Biochem, vol. 65, 2001, pp. 982-985.
Ochsner M. G. et al. (1990). J. Trauma. 30:884-887.
Office action for corresponding EP application 07867783.8, issued Feb. 9, 2011.
Olsen et al, Deliv Rev. Nov. 28, 2003;55(12):1547-67.
Otani et al, "Effect of additives on gelation and tissue adhesion of gelatin D-poly(L-glutamic acid) mixture", Biomaterials vol. 19 (1998) pp. 2167 to 2173.
Pusateri AE, Holcomb JB, Kheirabadi BS, Alam HB, Wade CE, Ryan KL. Journal of Trauma-Injury Infection and Critical Care 2006, 60, 674-682.
Pusateri, 2004 J Biomed Mater Res B, 15; 70(1): 114-121.
QuikClot® ACS™ (Z-Medica, Wallington, CT) document.
Lerner R. et al. (1990). J. Surg. Res. 48:165-181.
Sabel M. et al. (2004). Eur. Spine J. 13 (1):597-101.
Spotnitz WD. Am J Surg 2001, 182, 8S-14S.
Weaver F. et al. (2002). Ann. Vasc. Surg. 16(3):286-93.
Werten MWT, et al. (2001). Protein Engineering. 14 (6): 447-454.
PCT Search Report for corresponding PCT application PCT/US2007/025726, transmitted on Dec. 14, 2009.
Yokoyama K et al. Protein Exp & Purif 26, 2002: p. 329-335 2002.
Rajagopalan et al. J Biologica Chem 236(4), 1961.
Akira et al, Activity and Stability of Microbial Transglutaminase Modified with a Water-Soluble Polymer, JapaneseJournal of Polymer Science and Technology (Kobunshi Ronbunshu), vol. 58, No. 2, pp. 73-77 (Feb. 2001).
Office action issued for corresponding European Application No. 11192607.7, mailed May 10, 2012.

(56) References Cited

OTHER PUBLICATIONS

Kozlov P V et al: "The structure and properties of solid gelatin and the principles of thier modification" Jun. 1, 1983, Polymer, Elsevier Science Publishers B.V, GB, pp. 651-666.
Notice of Opposition for corresponding EP application 07867783.8, mailed Dec. 3, 2013.
Office action issued for corresponding European Application No. 11192607.7, mailed Jan. 2, 2013.
Office action from corresponding Chinese application No. CN 201080057151.0, mailed Nov. 27, 2013 (originalChinese language document).
SAS_SAT 9_2 Users Guide, undated.
Office action issued for related EP 11768111.4 Mailed Feb. 27, 2014.
Translation of office action from corresponding Japanese application No. 2009-541417, mailed Dec. 3, 2013.
Translation of summary of office action from corresponding Chinese application No. CN 201080057151.0. mailed Nov. 2013.
William D. Spotnitz, M.D. Commercial fibrin sealants in surgical care. The American Journal of Surgery (2001),8S-14S, 182.
Xie Z-P et al: "A novel casting forming for cermics by gelatine and enzyme catalysis" Mar. 1, 2000 (200-03-01), Journal of the European Ceramic Society, Elsevier Science Publishers, Barking, Essex, GB, pp. 253-257, XP004185604.
Office action issued for corresponding Japanese Application No. 2011-267107, mailed Feb. 4, 2014—Translation.
Office action issued for related Chinese Application 201180044965.5 Mailed Feb. 7, 2014—Translation.
Office action issued for related Chinese Application 201180044965.5 Mailed Feb. 7, 2014.
De Carvalho & Grosso, "Characterization of gelatin based films modified with transglutaminase, glyoxal and formaldehyde", Food Hydrocolloids 18 (2004) 717-726.
Dong et al., ""Optimization of cross-linking parameters during production of transglutaminase-hardened spherical multinuclearmicrocapsules by complex coacervation"" Colloids and Surfaces B: Biointerfaces 63 (2008) 41-47.
Ajinomoto GRAS summary for transglutaminase, Jun. 1997.
Office Action of related JP2013265507 mailed Jan. 20, 2015.
Office Action of related JP2013265507 mailed Jan. 20, 2015 (Translated).
Abrams GW et al. The incidence of corneal abnormalities in the Silicone Study. Silicone Study Report 7. Arch Ophthalmol 1995;113:764-769.
Alio JL et al. A new acrylic tissue adhesive for conjunctival surgery: experimental study. Ophthalmic Res 2003, 35:306-312.
Bloom JN et al. A Light-activated surgical adhesive for sutureless ophthalmic surgery, Arch Ophthamol 2003; 121: 1591-1595.
Cooper et al. J. Thorac. Cardiovasc. Surg. 109106-116, 1995.
Cooper et al. J. Thorac. Cardiovasc. Surg. 1121319-1329, 1996.
Eidt et al. Am J Surg 1999;178:511-516.
Ghazi NG et al. Pathology and pathogenesis of retinal detachment. Eye 2002;16:411-421.
Grotenhuis Andre J. Healthcare Economics Costs of postoperative cerebrospinal fluid leakage: 1-year, retrospective analysis of 412 consecutive nontrauma cases, Surgical Neurology 64 (2005) 490-494.
Johanning JM et al. Femoral artery infections associated with percutaneous arterial closure devices, J Vasc Surg 2001;34:983-985.
Katloff et al. A Comparison of Median Sternotomy and Thoracoscopic Approaches, Chest 110:1399-1406,1996.
Ninan L et al. Adhesive strength of marine mussel extracts of procine skin. Biomaterials 2003;24:4091-4099.
Olivieri MP et al. Surface properties of mussel adhesive protein component films. Biomaterials 1992,13:1000-1008.
Shahidi M et al. Retinal topography and thickness mapping in atrophic age related macular degeneration. Br J Ophthalmol 2002;86:623-626.
Smith TP et al. Infectious complications resulting from use of hemostatic puncture closure devices, Am J Surg 2001;182:658-662.
Swanson et al. J Am. Coll Surg: 185:25-32, 1997.
Toursarkissian B et al. Changing Pattern of Access Site Complications with the Use of Percutaneous Closure Devices, Vasc Endovasc Surg 2001;35:203-206.
Velazquez AJ at el., New dendritic adhesives for sutureless ophthalmic surgical procedures: in viro studies of corneal laceration repair. Arch Ophthamol 2004;122:867-870.
Agricultural and Biological Chemistry, 1989 (53,10), 2619-2623.
De Joung et al. J. Agric.Food.Chem, 2001(49), 3389-3393.
Gan et al. Food Hydrocolloids 2009 (23), 1398-1405.
Hirose at al. Gelation of Bovine Serum Albumin by Glutathione, J Food Sci, 1990 (55,4) 915-917.
Kang et al. Effect of Disulfide Bond Reduction on Bovine Serum Albumin—Stabilized Emulsion Gel Formed by Microbial Transglutaminase, J Food Sci, 2003 (68,7), 2215-2220.
Lee et al. Agricultural and Biological Chemistry, vol. 55, No. 8 (1991) 2057-2062.
Tobitani et al, Heat-Induced Gelation of Globular Proteins. 1. Model for the Effects of Time and Temperature on the Gelation Time of BSA Gels, Macromolecules, 1997 (30,17), 4845-4854.
Alur HH et al. Transmucosal sustained-delivery of chlorpheniramine maleate in rabbits using a novel, natural mucoadhesive gum as an excipient in buccal tablets, Int. J. Pharm., 1999, 88(1), 1-10.
Babin H et al. Food Hydrocolloids 2001, 15, 271-276.
Bernkop-Schnurch A et al. Pharm. Res., 1999, 16, 6, 876-81.32.
Buchta C et al. Biochemical characterization of autologous fibrin sealants produced by CryoSeal and Vivostat in comparison to the homologous fibrin sealant product Tissucol/Tisseel, Biomaterials 2005, 26, 6233-41.27-30.
Burzio LA et al. Cross-Linking in Adhesive Quinoproteins: Studies with Model Decapeptides, Biochemistry 2000, 39, 11147-53.
Deacon MP et al. Structure and Mucoadhesion of Mussel Glue Protein in Dilute Solution, Biochemistry 1998, 37, 14108-12.
Ehrbar M et al. Enzymatic formation of modular cell-instructive fibrin analogs for tissue engineering, Biomaterials 2007, 28, 3856-66.
Fisher MT et al, PNAS 103, 2006: p. 13265-6.
Garcia Y et al. Assessment of cell viability in a three-dimensional enzymatically cross-linked collagen scaffold. J Mater Sci Mater Med. Oct. 2007;18(10):1991-2001.
Ghebremeskel et al 2006, International Journal of Pharmaceutics 328: 119-129.
Glickman M et al. Arch Surg 2002, 137, 326-31.
Gutowska A et al. Anat Rec 2001, 263, 342-349.
Haines-Butterick L et al. Controlling hydrogelation kinetics by peptide design for three-dimensional encapsulation and injectable delivery of cells, Proc Natl Acad Sci U S A 2007, 104, 7791-6.
Hussain I et al, Animal Feed science and Technology, 1996;62 (2), p. 121-129.
Ikura K et al. Biosci Biotechnol Biochem. 66(6), 2002, p. 1412-1414.
Iwata H et al. A novel surgical glue composed of gelatin and N-hydroxysuccinimide activated poly(L-glutamic acid): Part 1. Synthesis of activated poly(L-glutamic acid) and its gelation with gelatin; Biomaterials 1998, 19, 1869-76.
Jackson M. Fibrin sealants in surgical practice: An overview, Am J Surg 2001, 182, 1S-7S.
Juggi JS et al., In-Vivo Studies with a cation Exchange Resin Mixture in the Removal of Excessive Ammonium from the Extracorporeal Circulation System. ANZ J Surg 1968;38 (2) p. 194-201.
Langoth N et al. Development of buccal drug delivery systems based on a thiolated polymer, Int. J. Pharm., 2003, 252, 141-48.
Lehr C et al. Pharma Res., 1992, 9(4), 547-53.
Lim DW et al. In Situ Cross-Linking of Elastin-like Polypeptide Block Copolymers for Tissue Repair; Biomacromolecules 2008, 9, 222-30.
Ma et al. Enhanced biological stability of collagen porous scaffolds by using amino acids as novel cross-linking bridges; Biomaterials. 2004, 25(15): p. 2997-3004.

(56) References Cited

OTHER PUBLICATIONS

Mahoney MJ et al. Contrasting effects of collagen and bFGF-2 on neural cell function in degradable synthetic PEG hydrogels; J Biomed Mater Res A 2007, 81, 269-78.
McDowell et al. Rotational Echo Double Resonance Detection of Cross-links Formed in Mussel Byssus under High-Flow Stress; Biol Chem 1999, 274,20293-5.
Motoki M et al. Transglutaminase and its use for food processing; Trends in Food Science & Technology 1998, 9, 204-210.
Nakamura E et al. Role of glutamine and arginase in protection against ammonia-induced cell death in gastric epithelial cells, Am J of Phys. GI and Liver Phys, 2002; 46(6), p. G1264-G1275.
IUB Nomenclature Committee. "Units of enzyme activity. Recommendations 1978. Prepared by Karlson P, Bielka H, Horecker BL, Jakoby WB, Keil B, Liébecq C, et al." Eur J Biochem 97 (1979): 319-20.
Nemes, Zoltan, Lyuben N. Marekov, and Peter M. Steinert. "Involucrin Cross-linking by transglutaminase 1 Binding to Membranes Directs Residue Specificity." Journal of Biological Chemistry 274.16 (1999): 11013-11021.
Rubin, Andrew L, and Robert H. Rice. "Differential regulation by retinoic acid and calcium of transglutaminases in cultured neoplastic and normal human keratinocytes." Cancer research 46.5 (1986): 2356-2361.
Product-data-sheet-TG1, 2014.
Pasternack, Ralf, et al. "A fluorescent substrate of transglutaminase for detection and characterization of glutamine acceptor compounds." Analytical biochemistry 249.1 (1997): 54-60.
Johnson, Gail VW, et al. "Transglutaminase activity is increased in Alzheimer's disease brain." Brain research 751.2 (1997): 323-329.
Lichtenauer, Michael, et al. "Phosphate buffered saline containing calcium and magnesium elicits increased secretion of interleukin-1 receptor antagonist." Laboratory Medicine 40.5 (2009): 290-293.
D'Argenio, G., et al. "Differential expression of multiple transglutaminases in human colon: impaired keratinocyte transglutaminase expression in ulcerative colitis." Gut 54.4 (2005): 496-502.
TGase assay (Hydroxamate assay)—Ajinomoto Data Sheet, 2004.
McDermott, Martin K, et al. "Mechanical properties of biomimetic tissue adhesive based on the microbial transglutaminase-catalyzed crosslinking of gelatin." Biomacromolecules 5.4 (2004): 1270-1279.
"Kei-ichi Yokoyama et al., ""In vitro refolding process of urea-denatured microbialtransglutaminase without pro-peptide sequence,"" Protein Expression and Purificationvol. 26 (2002): 329-335."
"K. V. Rajagopalan et al., ""Competitive Inhibition of Enzyme Activity by Urea,"" TheJournal of Biological Chemistry vol. 236, No. 4 (Apr. 1961 ): 1 059-1065."
"Aurin M. Chase, Hildegard C. von Meier and Vincent J. Menna, ""New CompetitiveInhibition and Irreversible Inactivation of Yeast Invertase by Urea,"" Journal of Cellularand Comparative Physiology vol. 59, Issue 1 (1962): 1, accessed Jun. 22, 2016,doi: 10.1 002/jcp.1 030590102."

"Pauline M. Emerson and J. H. Wilkinson, ""Urea and oxalate inhibition of the serumlactate dehydrogenase,"" J Clin Pathol18 (1965) 803-807, accessed Jun. 21, 2016,doi: 1 0.1136/jcp.18.6.803."
"Seikoh Horiuchi, Masayasu Inoue and Yoshimasa Morino, ""Latent Active Site in RatKidneyγ-Giutamyl Transpeptidase: Refolding Process of the Large Subunit andCharacterization of the Renatured Enzyme,"" Eur. J. Biochem. 105 (1980): 93-102."
"Anders Peter et al., ""Semenogelin I and semenogelin II, the major gel-formingproteins in human semen, are substrates for transglutaminase,"" Eur. J. Biochem. 252(1998): 216-221."
"Martin L. Schwartz et al., ""The Effect of Fibrin-Stabilizing Factor on the SubunitStructure of Human Fibrin,"" The Journal of Clinical Investigation 50 (1971 ): 1506-1513, accessed Jun. 24, 2016, doi: 1 0.1172/JCI1 06636".
"Susan M. Dallabrida, Lisa A. Falls and David H. Farrell, ""Factor XII la supportsmicrovascular endothelial cell adhesion and inhibits capillary tube formation in fibrin,"" Blood Journal vol. 95, No. 8 (2000): 2586-2592".
"Charles S. Greenberg, Joseph V. Dobson and Charles C. Miraglia, ""Regulation ofPlasma Factor XIII Binding to Fibrin In Vitro,"" Blood Journal vol. 66, No. 5 (1985):1028-1034".
"Michitaka Naito, Hideki Nomura and Akihisa Iguchi, ""Migration of Cultured VascularSmooth Muscle Cells into Non-Crosslinked Fibrin Gels,"" Thrombosis Research vol. 84, No. 2 (1996): 129-136".
"Eiji Niwa et al., ""Contribution of SS Bonds to the Elasticity of Actomyosin Gel in whichCoexisting Transglutaminase was inactivated,"" Fisheries Science vol. 61, No. 3(1995): 438-440".
"Hiroshi Umakoshi et al., ""Characterization of Surface Properties of MicrobialTransglutaminase Using Aqueous Two-Phase Partitioning Method,"" SolventExtraction Research and Development, Japan vol. 15 (2008): 111-115".
"J. E. Folk and P. W. Cole, ""Identification of a Functional Cysteine Essential for theActivity of Guinea Pig Liver Transglutaminase,"" J. Bioi. Chem. vol. 241, No. 13(1966): 3238-3240."
"Kei-ichi Yokoyama et al., ""Structure of Folding Intermediates at pH 4.0 and NativeState of Microbial Transglutaminase,"" Bioscience, Biotechnology, and Biochemistryvol. 67, No. 2 (2003): 291-294".
Fernandez-Diaz, M. D., P. Montero, and M. C. Gomez-Guillen. "Gel properties of collagens from skins of cod (*Gadus morhua*) and hake (*Merluccius merluccius*) and their modification by the coenhancers magnesium sulphate, glycerol and transglutaminase." Food Chemistry 74.2 (2001): 161-167.
Kozlov, P. V., and G. I. Burdygina. "The structure and properties of solid gelatin and the principles of their modification." Polymer 24.6 (1983): 651-666.
Nomura, Yoshihiro, et al. "The physicochemical property of shark type I collagen gel and membrane." Journal of agricultural and food chemistry 48.6 (2000): 2028-2032.
Otani, Yuto, Yasuhiko Tabata, and Yoshito Ikada. "Effect of additives on gelation and tissue adhesion of gelatin-poly(L-glutamic acid) mixture." Biomaterials 19.23 (1998): 2167-2173.
Product-data-sheet-T009, 2014.
Totosaus, Alfonso, et al. "A review of physical and chemical protein-gel induction." International journal of food science & technology 37.6 (2002): 589-601.

* cited by examiner

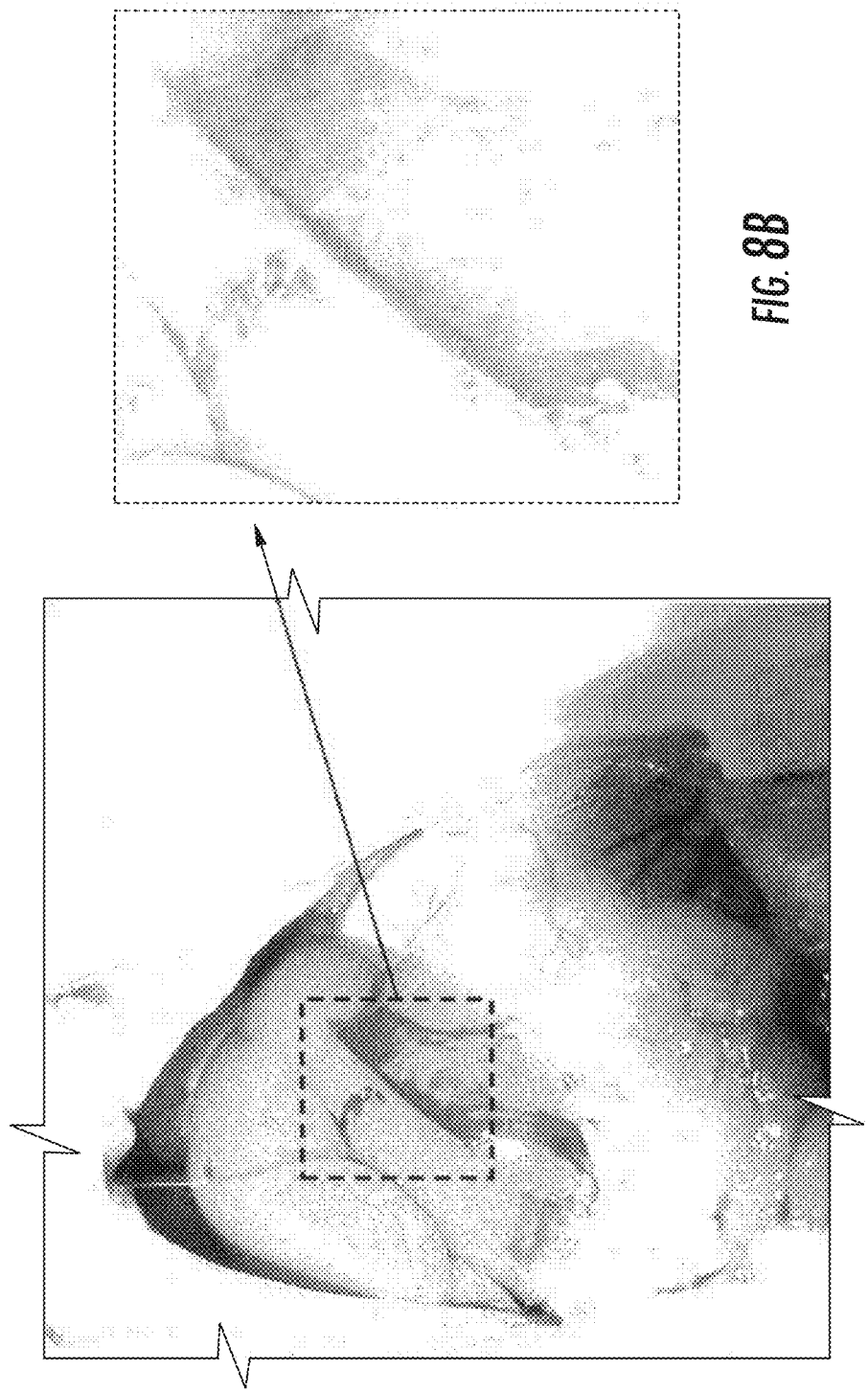

GELATIN-TRANSGLUTAMINASE HEMOSTATIC DRESSINGS AND SEALANTS

FIELD OF THE INVENTION

The present invention relates to hemostatic dressings, devices, and agents that contain resorbable or non-resorbable materials and/or coagulation proteins. The hemostatic devices are useful for the treatment of wounded tissue.

BACKGROUND OF THE INVENTION

The control of hemorrhage (bleeding) is a critical step in first aid and field trauma care. Unfortunately, the occurrence of excessive bleeding or fatal hemorrhage from an accessible site is not uncommon (J. M. Rocko et al. (1982). J. Trauma 22:635). Mortality data from the Vietnam War indicates that 10% of combat deaths were due to uncontrolled extremity hemorrhage. Up to one third of the deaths from exsanguination during the Vietnam War could have been prevented by the use of effective field hemorrhage control methods. (SAS/STAT Users Guide, 4th ed. (Cary, N. C.: SAS Institute Inc; 1990)).

Although civilian trauma mortality statistics do not provide exact numbers for pre-hospital deaths from extremity hemorrhage, case and anecdotal reports indicate similar occurrences (J. M. Rocko et al. (1982). J. Trauma 22:635). These data suggest that a substantial increase in survival can be affected by the prehospital use of a simple and effective method of hemorrhage control. Unfortunately, such a method has not been successfully demonstrated by use of commercially available hemostatic devices.

Separately, surgical wound closure is currently achieved by sutures and staples that facilitate healing by pulling tissues together. However, very often they fail to produce the adequate seal necessary to prevent fluid leakage. Thus, there is a large, unmet medical need for devices and methods to prevent leakage following surgery, including leaks that frequently occur along staple and suture lines. Such devices and methods are needed as an adjunct to sutures or staples to achieve hemostasis or other fluid-stasis in peripheral vascular reconstructions, dura reconstructions, thoracic, cardiovascular, lung, neurological, and gastrointestinal surgeries.

Most high-pressure hemostatic devices currently on the market are nominally, if at all adhesive. Good examples of such devices are the QuikClot® ACS™ (Z-Medica, Wallington, Conn.) and HemCon™ bandage (HemCon, Portland, Oreg.), the two hemostatic devices currently supplied to members of the US armed forces. The mineral zeolite crystals in the QuikClot sponge cause adsorption of the water molecules in the blood, thus concentrating the clotting factors and accelerating blood clotting. The chitosan mixture that makes up the HemCon bandage has a positive charge and attracts red blood cells, which have a negative charge. The red blood cells are drawn into the dressing, forming a seal over the wound, and stabilizing the wound surface.

The HemCon bandage product mentioned above was developed in an attempt to provide pre-hospital hemorrhage control and has already demonstrated limited success in the field. However, the chitosan network that makes up the HemCon bandage can be saturated with blood and fail quickly when faced with brisk blood flow or after 1-2 hours when confronted with moderate blood flow from a wound (B. S Kheirabadi et al. (2005). J. Trauma. 59:25-35; A. E. Pusateri et al. (2006). J. Trauma. 60:674-682). Also, the HemCon bandage patch is available only as a stiff patch that cannot fit easily into irregular wounds, further limiting its utility.

Other polysaccharide-based hemostatic devices that have been suggested for use in hemorrhage control are RDH™ (Acetyl Glucosamine), TraumaDEX™ (MPH), and Chito-skin™ (Chitosan & Gelatin). However, none of these types of bandages have been able to consistently demonstrate avoidance of failure in the face of significant blood flow. Other recently introduced hemostatic devices include Celox™ (Chitosan Crystals) and WoundStat™ (Trauma-Cure Inc., MD) (granular blend of smectite mineral and a super absorbent polymer). However, both of these products rapidly swell to fill wound sites, making them appropriate only for accelerating blood clotting in specific types of wounds and presenting a danger of reducing or even eliminating blood flow in surrounding blood vessels.

QuikClot ACS™, also mentioned above, has also demonstrated efficacy in staunching moderate levels of hemorrhage. However, the water adsorption mechanism of mineral zeolite cannot occur without the release of a large amount of heat. As such, application of the QuikClot ACS™ results in high temperatures and severe burns at the injury site, which damage surrounding tissue areas and make later medical care far more complicated (A. E. Pusateri et al. (2006). J. Trauma. 60:674-682). Clearly, a hemostatic solution without this significant side effect is more ideal. While QuikClot has developed a mineral mixture that releases less heat upon application, the efficacy of the cooler mixture is insufficient for serious trauma care. Furthermore, neither the original nor cooler mineral mixtures can stop brisk arterial bleeding.

All of the above-mentioned products rely on the natural clotting cascade to control fluid leakage from a wound site. As such, they are all only useful only for stopping blood flow and each only under conditions appropriate for that particular device. General wound site sealing, particularly of injured sites leaking non-blood fluids, are beyond the scope of these products.

SUMMARY OF THE INVENTION

There is a need for, and it would be useful to have, a non-toxic adhesive material which could be used for a wide variety of applications, including but not limited to surgical applications, control of hemorrhage and control of bleeding from a wound. There is also a need for, and it would be useful to have, a non-toxic adhesive material which could be used as part of a hemostatic bandage. There is also a need for, and it would be useful to have, a non-toxic adhesive material which could be used as a surgical sealant.

The present invention overcomes the drawbacks of the background art by providing an adhesive material which comprises a cross-linkable protein and a non-toxic material which induces cross-linking of the cross-linkable protein. Preferably, the cross-linkable protein includes gelatin and any gelatin variant or variant protein as described herein. Optionally and preferably, the non-toxic material comprises transglutaminase (TG), which may optionally comprise a microbial transglutaminase (mTG). According to some embodiments of the present invention, the adhesive material is provided in a bandage, which is preferably adapted for use as a hemostatic bandage. According to other embodiments, it is provided as a sealant, which is preferably adapted for use as a surgical sealant.

When acted upon by a transglutaminase, gelatin, which is a denatured form of the protein collagen, undergoes rapid crosslinking to form a vibrant gel. The gelation process that takes place is extremely similar to the natural late stage clotting cascade that fibrin undergoes when it comes into contact with Factor XIII and calcium. Furthermore, the resulting gel demonstrates adhesive capacity very similar to, if not greater than, that of fibrin glues. (M. K. McDermott, Biomacromolecules. 2004 July-August; 5(4):1270-9).

The present invention utilizes the similarities of gelatin-TG cross-linking to the fibrin clotting cascade to mimic the superior hemostatic performance of an advanced fibrin dressing. Replacing the fibrin-thrombin sandwich of a fibrin bandage with a gelatin-TG sandwich results in the creation of a novel, inexpensive, and stable dressing that can control hemorrhage without significant side effects. This new bandage maximizes the adhesive properties of the gelatin-TG mixture by allowing for the controlled application of a large amount of the mixture to a wound site in a way that prevents the spread of TG to areas not contacted by the bandage. As such, this synergistic technology represents an advance to both the field of advanced fibrin dressings and the field of gelatin-TG adhesion.

Unlike a clotted fibrin network, the gelatin-TG network has an additional benefit in that it can be dissolved specifically using a specified protease that is not otherwise physiologically reactive (T. Chen, Biomacromolecules. 2003 November-December; 4(6):1558-63). Thus, while a gelatin-mTG hemostatic sandwich dressing can replicate the performance of a fibrin-thrombin hemostatic sandwich dressing, it can also be removed as desired without complication.

Beyond its application as a hemostatic field-dressing for trauma care, the present invention of a gelatin-TG based hemostatic device has great potential in controlling brisk, arterial bleeding during surgery, bleeding after endo-vascular catherization, or leakage of other bodily fluids after injuries or doing surgery.

To date, though the gelling properties of cross-linked gelatin-TG and the adhesive capacity of gelatin-TG cross-linking have been separately explored, no efforts have been made to use both characteristics together to form a hemostatic or tissue sealing composition.

Adhesive use of the gelatin-TG compound was demonstrated in vivo in a rat retina model, where a drop of gelatin-TG mixture was used for retinal attachment (T. Chen, J Biomed Mater Res B Appl Biomater. 2006 May; 77(2):416-22).

Use of gelatin-TG gel as a scaffold for cell therapy was also tested (U.S. Pat. No. 5,834,232. Also Ito A, J Biosci & Bioeng. 2003; 95(2): 196-99. Also, Broderick E P, J Biomed Mater Res B Appl Biomater. 2005 Jan. 15; 72(1):37-42).

While these studies emphasized the safety of physiological use of the gelatin-TG mixture, they each only used one of the characteristics of gelatin-TG cross-linking, and failed to teach or suggest the hemostasis and tissue sealing advancement presented in the current invention.

Use of the gelatin-TG mixture for hemostasis or fluid-stasis also marks a significant advancement from a number of well-documented attempts to use transglutaminases, particularly tissue TG, independently as surgical adhesives (U.S. Pat. No. 5,736,132, U.S. 61/908,196, among many). Employing gelatin as a substrate for TG adds a mechanical scaffold to the TG activity that provides a number of advantages over the use of TG alone. TG together with gelatin can be applied more precisely than TG alone, can conform precisely to a wound site, and allows for controlled bioabsorbability.

The present invention overcomes the drawbacks of the background art. Prior attempted solutions used many forms of modified and unmodified gelatin networks for mild to moderate hemostasis. However, a method of forming, in situ, a strongly cross-linked gelatin network that can control brisk bleeding arterial hemorrhage or other significant bodily fluid leakages has been lacking. A method, such as gelatin-TG cross-linking that can form a strong gelatin network in vivo increases the mechanical strength of a gelatin matrix and makes it suitable for controlling high-pressure arterial bleeding and other bodily fluid leakages. Aside from the improved method of cross-linking, the present invention involves many other innovations that provide it with advantages over existing gelatin-based hemostatic materials. A non-limiting, illustrative, partial list is provided below:

1) In-situ cross-linking between gelatin chains and endogenous collagen of tissue ECM (extra cellular matrix) creates a strong, hemostatic barrier for fluids.
2) Gelatin and TG can more effectively affect hemostasis or fluid-stasis by being applied in lyophilized form and reconstituted by the blood or other body fluid.
3) A gelatin-TG mixture in lyophilized form has increased shelf life.
4) Gelatin and TG in layered, lyophilized form provided more rapid reconstitution, which is helpful for a high pressure fluid flow environment.
5) The addition of a mechanical backing to the basic gelatin-TG mixture increases the hemostatic or fluid control capacity of the mixture by slowing the fluid and allowing the gelatin-TG more time to cross-link and block the fluid leakage.

According to some preferred embodiments of the present invention, the gelatin-mTG mixture is partially cross-linked prior to application to a wound site or prior to lyophilization. In another embodiment, non-cross-linked gelatin or mTG is present together with partially cross-linked gelatin-mTG.

Hemostatic bandages which are adhesive in nature are known in the art, yet have many complications and drawbacks to their use. For example, the widespread hemostatic use of fibrinogen and thrombin was common in the last year of World War II, but was abandoned because of the transmission of hepatitis (D. B. Kendrick, Blood Program in WW II (Washington, D.C.: Office of the Surgeon General, Department of Army; 1989), 363-368).

Fibrinogen dressings were first used by trauma surgeons during World War I when Grey and his colleagues made prepolymerized fibrin sheets and powders. During World War II, fibrin glue was created with prepolymerized Styrofoam-like sheets of fibrin and fibrin films by the United States military and the American Red Cross. Fibrin based dressings show a significant difference in controlling bleeding time and reducing blood loss when compared to a control. (Jackson, M., et al. (1996). J. of Surg. Res. 60:15-22; and Jackson, M., et al. (1997). Surg. Forum. XL, VIII:770-772)

Despite the efficacy of fibrinogen dressings in controlling hemorrhage, the use of fibrinogen dressings was discontinued as blood and serum borne diseases such as hepatitis and HIV were often transmitted since the dressings comprised purified human or animal fibrinogen or other purified blood products. (Holcomb, J. B., et al. (1997). Surgical Clinics of North America. 77:943-952)

In the past few years, however, there has been a renewed interest in fibrin based products for treating wounds as plasma purification techniques have greatly reduced the risk of blood and serum borne diseases.

A hemostatic sandwich dressing has been described by the US Red Cross, which contains a layer of thrombin sandwiched between layers of fibrinogen (see, e.g., PCT/US99/

10952, U.S. Pat. Nos. 6,054,122, 6,762,336). That hemostatic dressing has demonstrated much success in treating potentially fatal trauma wounds (E. M. Acheson. (2005). J. Trauma. 59(4):865-74; discussion 874-5; B. S. Kheirabadi. (2005). J. Trauma. 59(1):25-34; discussion 34-5; A. E. Pusateri. (2004). J. Biomed. Mater. Res. B Appl. Biomater. 15; 70(1):114-21) In fact, in those porcine studies, the fibrin sandwich dressing greatly outperformed the HemCon and QuikClot products in treating potentially fatal trauma wounds, demonstrating a >75% survival rate after 2 hours, versus 0% survival when the standard army field bandage, HemCon bandage, or QuikClot powder was used.

Although such dressings can be used in methods for treating wounded tissue, such conventional sandwich dressings can become delaminated, whereby the edges of the layers of the dressing no longer adhere to each other. Such delamination can result in reduced interaction of the dressing components layers, with decreased effectiveness of the dressing in preventing hemorrhage.

An improved fibrin-based hemostatic sandwich dressing has been described which comprises a plurality of layers that contain resorbable materials and/or coagulation proteins. Specifically, the dressing (see PCT/US03/28100, U.S. Patent Application No. 60/155,234) includes a layer of thrombin sandwiched between a first and second layer of fibrinogen, wherein the layer of thrombin is not coextensive with the first and/or second layer of fibrinogen.

Despite the advances in fibrin wounds dressings, these bandages suffer from many drawbacks. The lyophilized fibrinogen used to make the bandage must be purified from human blood plasma. As this is a costly and delicate procedure, the resulting fibrinogen bandage is extremely expensive to produce and only has a very short shelf life at room temperature. The more fibrinogen that is added to the backing, the better the bandage works in stopping bleeding. However, the more fibrinogen added to the backing, the more costly the bandage. Additionally, high amounts of fibrinogen on the bandage backing may contribute to the fragility of the bandage, making it crumbly and difficult to work with. As a result of these limitations, no efficacious fibrin bandage is commercially available.

Thus, while an advanced fibrin dressing could control hemorrhage without significant side effects and fill the previously mentioned deficiency in active trauma care hemostasis, price and stability limitations present strong disadvantages to the use of this type of dressing.

Liquid fibrin sealants or glues have been used for many years as an operating room adjunct to hemorrhage control (J. L. Garza et al. (1990). J. Trauma. 30:512-513; H. B. Kram et al. (1990). J. Trauma. 30:97-101; M. G. Ochsner et al. (1990). J. Trauma. 30:884-887; T. L. Matthew et al. (1990). Ann Thorac. Surg. 50:40-44; H. Jakob et al. (1984). J. Vasc. Surg. 1:171-180). Also, single donor fibrin sealants have also been widely used clinically in various surgical situations. (W. D. Spotnitz. (1995). Thromb. Haemost. 74:482-485; R. Lerner et al. (1990). J. Surg. Res. 48:165-181)

While a number of absorbable surgical hemostats are currently used in the surgical arena, no existing product is sufficiently strong to provide the mechanical and biological support necessary to control severe hemorrhage or vigorous flow of other biological fluids.

Currently available hemostatic bandages such as collagen wound dressings (INSTAT™, Ethicon, Somerville, N.J., and AVITENE™, C R Bard, Murray Hill, N.J.) or dry fibrin thrombin wound dressings (TACHOCOMB™, Hafslund Nycomed Pharma, Linz, Austria) are restricted to use in surgical applications, and are not sufficiently resistant to dissolution in high blood flow. They also do not possess enough adhesive properties to serve any practical purpose in the stanching of severe blood flow. These currently available surgical hemostatic bandages are also delicate and thus prone to failure should they be damaged by bending or loading with pressure. They are also susceptible to dissolution in hemorrhagic bleeding. Such dissolution and collapse of these bandages may be catastrophic, because it can produce a loss of adhesion to the wound and allow bleeding to continue unabated.

Arterial bleeding is also not manageable with the application of oxidized cellulose (SURGICEL, Ethicon, Somerville, N.J.) or gelatin sponge (SURGIFOAM, Ethicon, Somerville, N.J.) absorbable hemostats. These products are intended to control low-pressure bleeding from bone and epidural venous oozing. Gelatin sponges are not appropriate for high-pressure, brisk flowing arterial bleeding because they do not form a tight bond with the source of bleeding and are thus easily dislodged. Oxidized cellulose is also not appropriate for controlling arterial bleeding because it swells and needs to be removed from the application site when hemostasis is achieved. When the blood flow is too high, too much swelling occurs before hemostasis can be achieved (M. Sabel et al. (2004). Eur. Spine J. 13 (1):597-101).

The most widely used tissue adhesives are generally unfit for use as hemostatic or internal fluid-stasis devices, for reasons generally related to mild toxicity and inability to be easily prepared and applied in the field. A good example of this is the cyanoacrylate family of topical skin adhesives, such as Dermabond™, Indermil™, Liquiband™ etc. The nature of cyanoacrylate's rapid activation when exposed to air renders cyanoacrylate-based products inappropriate for use in an active hemostatic field dressing and their inability to bind to wet surfaces renders them inappropriate for internal hemostatis or fluid-stasis usage.

Existing products that are intended for internal fluid-stasis usage also have significant problems. BioGlue™ (Cryolife Inc.) is a strong adhesive and sealant but contains albumin crosslinked by glutaraldehyde, a substance which is toxic and highly neurotoxic. This toxicity greatly limits its usage. Another sealant is CoSeal (Baxter), which is composed of polyethylene glycol (PEG). Though it is non-toxic, it has only weak adhesive strength, greatly limiting its applications.

Gelatin has been used in a variety of wound dressings. Since gelatin gels have a relatively low melting point, they are not very stable at body temperature. Therefore, it is imperative to stabilize these gels by establishing cross-links between the protein chains. In practice, this is usually obtained by treating the gelatin with glutaraldehyde or formaldehyde. Thus, cross-linked gelatin may be fabricated into dry sponges which are useful for inducing hemostasis in bleeding wounds. Commercially available examples of such sponges include Spongostan (Ferrosan, Denmark), Gelfoam (Upjohn, USA), and Surgifoam (Ethicon. Somerville, N.J.). A major disadvantage of these sponges is that the cross-linking agent used (formaldehyde or glutaraldehyde) is toxic for cells. The negative effect of glutaraldehyde cross-linking is exemplified, for instance, by the findings of de Vries et al (Abstract Book of the Second Annual Meeting of the WHS, Richmond, USA, p 51, 1992). These authors showed that glutaraldehyde cross-linked collagen lattices were toxic for cells, whereas the non cross-linked variety was not. Therefore, despite their beneficial hemostatic properties, these products are not very optimal as wound dressings for the treatment of problematic wounds. Consequently, a gelatin-based wound dressing which uses a different, less toxic, cross-linking technology would be very desirable.

Aside from potential toxicity, gelatin networks alone do not provide the mechanical properties necessary for controlling brisk bleeding. They are more appropriate for wound management applications that only require a small amount of fluid absorption. In one study, it was concluded that sheets of glutaraldehyde cross-linked gelatin are more appropriate as a dressing for sustained wound healing, particularly of dystrophic tissue which need longer time. Alternatively, they may be useful as a scaffold for cell attachment, where they can stimulate a poorly reactive microenvironment throughout prolonged in situ presence (M G Tucci. (2001). J. Bioactive & Comp. Polymers. 16(2): 145-157).

Gelatin networks cross-linked with polysaccharides have also been suggested for use in controlling bleeding. These hemostatic compounds are unhindered by the potential toxicity of glutaraldehyde cross-linked gelatin sponges. However, the gelatin-polysaccharide substances generally lack mechanical strength and are intended mainly to control small amounts of oozing fluid during surgery or to limit wound oozing over an extended, post-medical care period.

One example of a gelatin-polysaccharide compound is a gelatin-alginate wound dressing that is cross-linked in situ. Such a dressing has no adhesive function and is mainly used to hold in moisture on the wound site. The dressing swells to 90% of its initial size, which greatly reduces its mechanical strength (B Balakrishnan et al. (2005). Biomaterials. 26(32):6335-42).

Another, more widespread example, is a cross-linked gelatin-chitosan wound dressing (examples in U.S. Pat. Nos. 6,509,039, 4,572,906). While some have suggested the use of such dressings for trauma care (Chitoskin™), the hemostatic properties of this material are simply insufficient to control high-pressure bleeding. Also, the material swells significantly when confronted with high volumes of bodily fluids. Such dressings are more appropriate for treating chronic wounds and burns.

Yet another example is mentioned (U.S. Pat. No. 6,132,759) where solubilized gelatin is cross-linked with oxidized dextran. This material is suggested for the covering and long-term treatment of wounds since it demonstrated a high absorptive capacity and favorable controlled release properties for the delivery of therapeutic substances, particularly to wounds.

Currently no material involving cross-linked gelatin networks or networks of other materials cross-linked with gelatin has been able to independently provide hemostasis for brisk internal bleeding, even with the addition of thrombin. A study was done comparing the hemostatic capacity of FloSeal gelatin matrix (BioSurgery, Fremont, Calif.) and GelFoam gelatin matrix soaked in active thrombin solution. Neither enhanced hemostatic device was able to stop flow characterized bleed in more than ⅔ of patients after 5 minutes. Pulsatile arterial bleeding is far more brisk than flow bleeding and would most certainly present a problem for these thrombin-soaked matrices (F A Weaver et al. (2002). Ann Vasc. Surg. 16(3):286-93).

In any case, there remains a distinct deficiency in trauma care, in that there is no novel, active hemostatic field dressing available that can control hemorrhage without significant side effects. Similarly, there remains a distinct deficiency in surgical care, in that there is no non-toxic sealant available that is capable of withstanding brisk bleeding and able to seal wound sites leaking non-blood body fluids.

According to some embodiments of the present invention, there is provided a method of treating a wounded tissue, comprising applying to the tissue a composition comprising gelatin and a non-toxic cross-linking agent.

Optionally, the non-toxic cross-linking agent comprises transglutaminase. Preferably, the transglutaminase is included as part of a transglutaminase composition and the weight ratio of gelatin to transglutaminase composition is in a range of from about 1:1 to about 300:1. More preferably, the transglutaminase composition has a specific activity level of at least about 40 U/gm. Most preferably, the transglutaminase composition has a specific activity level of at least about 800 U/gm.

Optionally and preferably, activity of the transglutaminase in the gelatin-transglutaminase composition is from about 25 to about 400 U/g of gelatin. More preferably, the activity is from about 40 to about 200 U/g of gelatin.

Optionally, the transglutaminase comprises a plant, recombinant animal, or microbe derived transglutaminase other than blood derived Factor XIII. Preferably, the composition has a pH in a range of from about 5 to about 8.

Optionally, the gelatin is produced from animal origin, recombinant origin or a combination thereof. Preferably, the animal origin is selected from the group consisting of fish and mammals. More preferably, the mammal is selected from the group consisting of pigs and cows.

Optionally, the gelatin is of type A (Acid Treated) or of type B (Alkaline Treated). More preferably, gelatin comprises high molecular weight gelatin.

Optionally, wounded tissue is selected from the group consisting of surgically cut tissue, surgically repaired tissue, and traumatized tissue.

Optionally, the method further comprises reducing bleeding or leakage of other bodily fluids from the tissue. Optionally a bodily fluid is selected from the group consisting of cerebral spinal fluid, intestinal fluid, air, bile, and urine. Preferably, the method further comprises inducing hemostasis or stasis of other leaking bodily fluids in the tissue.

Optionally, the wound is bleeding or leaking another bodily fluid and treating the wounded tissue comprises applying the composition to the wound site to encourage in situ cross-linking between gelatin chains and the endogenous collagen of tissue extracellular matrix to create a barrier to fluid leakage or bleeding.

Optionally, the method further comprises forming a biomimetic clot.

Optionally, applying the composition comprises: Mixing the gelatin and the transglutaminase to form a mixture; and Applying the mixture to the tissue.

According to other embodiments of the present invention, there is provided a method for inducing hemostasis in a wound of a mammal, the method comprising applying to the wound a composition comprising gelatin and transglutaminase.

According to still other embodiments of the present invention, there is provided a method for inducing formation of a biomimetic clot at a site of a damaged blood vessel, comprising applying to the wound a composition comprising gelatin and transglutaminase.

According to still other embodiments of the present invention, there is provided a composition comprising a combination of gelatin and transglutaminase, wherein a ratio of an amount of the gelatin and an amount of the transglutaminase is selected to induce formation of a biomimetic clot in a mammal.

According to still other embodiments of the present invention, there is provided a composition comprising a combination of gelatin and non-toxic cross-linking agent, wherein a ratio of an amount of the gelatin and an amount of the non-toxic cross-linking agent is sufficient to reduce bleeding in a wound of a mammal.

Preferably, the non-toxic cross-linking agent comprises transglutaminase. More preferably, the transglutaminase is added as part of a transglutaminase composition and the weight ratio of gelatin to transglutaminase composition is in a range of from about 1:1 to about 300:1. More preferably, the ratio is in a range of from about 1:1 to about 100:1. Most preferably, the transglutaminase composition has a specific activity level of at least about 40 U/gm. Also most preferably, the transglutaminase composition has a specific activity level of at least about 80 U/gm. Also most preferably, the transglutaminase composition has a specific activity level of at least about 200, 400 or 800 U/gm.

Optionally activity of the transglutaminase in the gelatin-transglutaminase composition is from about 25 to about 400 U/g of gelatin. Preferably, activity is from about 40 to about 200 U/g of gelatin.

Optionally, the transglutaminase comprises a plant, recombinant, animal, or microbe derived transglutaminase other than blood derived Factor XIII. Preferably, the composition further comprises a stabilizer or filler. Also preferably, the composition has a pH in a range of from about 5 to about 8.

Optionally, gelatin is produced from animal origin, recombinant origin or a combination thereof. Preferably, the animal origin is selected from the group consisting of fish and mammals. More preferably, the mammal is selected from the group consisting of pigs and cows. Most preferably, the gelatin comprises pig skins or pig bones, or a combination thereof. Also most preferably, the gelatin is of type A (Acid Treated) or of type B (Alkaline Treated). Also most preferably, the gelatin comprises high molecular weight gelatin.

Optionally, the gelatin has a bloom of at least about 250. Preferably, the fish comprises a cold water species of fish.

Optionally, recombinant gelatin is produced using bacterial, yeast, animal, insect, or plant systems or any type of cell culture.

Optionally, gelatin is purified to remove salts.

Optionally, gelatin has at least one adjusted, tailored or predetermined characteristic. Optionally, the gelatin does not undergo thermoreversible gelation.

According to still other embodiments of the present invention, there is provided a hemostatic or body fluid sealing agent comprising a combination of gelatin and a non-toxic cross-linking agent. Optionally, the non-toxic cross-linking agent comprises transglutaminase. Preferably, the combination comprises aggregated gelatin and transglutaminase.

As described herein, a method or composition in which the transglutaminase may optionally be extracted from one or more of *Streptoverticillium Baldaccii*, a *Streptomyces Hygroscopicus* strain, or *Escherichia Coli*.

According to still other embodiments of the present invention, there is provided a method of inducing hemostasis in and/or sealing a wounded tissue, comprising applying to the tissue a composition comprising a cross-linking protein substrate and a non-toxic cross-linking agent. Optionally, the non-toxic cross-linking agent comprises transglutaminase. Preferably, the substrate comprises one or more synthesized polymer sequences featuring a transglutaminase cross-linking site. More preferably, the substrate comprises a modified polypeptide comprising at least one transglutaminase cross-linking site.

According to still other embodiments of the present invention, there is provided a composition for inducing hemostasis and/or sealing a wound, comprising a mixture of gelatin and transglutaminase, wherein the mixture is modified such that the gelatin forms a solution with transglutaminase at a temperature lower than the natural sol-gel transition temperature of standard animal gelatin.

Optionally, the gelatin has been modified to have a reduced sol-gel transition temperature. Preferably the composition further comprises an additive to increase solubility of the gelatin in the mixture. More preferably the composition further comprises an additive to reduce the sol-gel transition temperature of the gelatin. Most preferably, the composition further comprises a plasticizer. Optionally and most preferably, the plasticizer is selected from the group consisting of a polyhydric alcohol, glycerine, glycerol, xylitol, sucrose, sorbitol, triethanolamine, resorcin, thiodiglycol, sodium salt of toluenesulphoacid, butylene glycol, urea nitrate, thiourea, urea, glutamic acid, aspargic acid, valine, glycine, KSCN, KI, and LiBr.

Optionally, a concentration ratio range for glycerol is from about 0.5:1 to about 5:1 Glycerol:Gelatin, weight per weight. Preferably, the concentration ratio range is from about 1:1 to about 2:1 Glycerol:Gelatin, weight per weight. Optionally, a concentration ratio range for sorbitol is from about 0.5:1 to about 5:1 Sorbitol:Gelatin weight per weight. Preferably, the concentration ratio range is from about 1:1 to about 3:1 Sorbitol:Gelatin, weight per weight.

Optionally, a concentration ratio range for urea is from about 1:2 to about 2:2 urea:gelatin, weight per weight.

Optionally the composition further comprises an adjusting agent selected from the group consisting of a pH adjusting agent and an ion concentration adjusting agent. Preferably, the pH adjusting agent provides a pH in a range of from about 1.5 to about 5.0 or from about 7.0 to about 9.0.

Optionally the composition further comprises a salt.

Optionally, the composition further comprises a trehalose carbohydrate, mannitol carbohydrate, or other carbohydrate for stabilization for spray drying, lyophilization, or other protein drying.

Optionally the composition further comprises a denaturant. Preferably, the denaturant is selected from the group consisting of Guanidine Hydrochloride and Urea. More preferably a concentration ratio range is from about 1:2 to about 2:2 GuHCl:gelatin, weight per weight. Also more preferably, a concentration ratio range is from about 0.5:1 to about 1:1 urea: gelatin, weight per weight.

Optionally the composition further comprises a reducing agent. Preferably, the reducing agent is selected from the group consisting of magnesium chloride and hydroquinone. More preferably, the hydroquinone is present in solution of the mixture at a concentration of from about 0.2 to about 0.5 M. Most preferably, the concentration is from about 0.3 to about 0.4 M.

Optionally, the magnesium chloride is present in solution of the mixture at a concentration of from about 2 to about 4 M. Preferably the concentration is from about 2.5 to about 3.5M.

Optionally the composition further comprises an exothermic agent. Preferably, the exothermic agent comprises one or more of calcium chloride, other calcium salts, magnesium chloride, metallic oxides/zeolites, or a combination thereof. More preferably the calcium chloride is present in an amount of from about 0.2 to about 0.7 g of Calcium Chloride per mL of the mixture in solution for each degree Celsius increase in temperature above the ambient temperature.

Optionally the composition further comprises a gelatin specific protease.

Optionally the composition further comprises a protease inhibitor.

Optionally the composition further comprises an additional hemostatic agent. Preferably the additional hemostatic agent further comprises one or more of albumin, collagen, fibrin, thrombin, chitosan, ferric sulfate, or other metal sulfates.

According to other embodiments of the present invention there is provided a hemostatic or sealing dressing which comprises: (i) a first gelatin layer; (ii) a transglutaminase layer adjacent to the first gelatin layer; and (iii) a second gelatin layer adjacent to the transglutaminase layer, wherein the transglutaminase layer is coextensive or noncoextensive with the first gelatin layer and/or the second gelatin layer.

According to other embodiments of the present invention there is provided a hemostatic or sealing dressing which comprises: (i) a resorbable or non-resorbable material layer; (ii) a first gelatin layer adjacent to the material layer; (iii) a transglutaminase layer adjacent to the first gelatin layer; and (iv) a second gelatin layer adjacent to the transglutaminase layer, wherein the transglutaminase layer is coextensive or noncoextensive with the first gelatin layer and/or the second gelatin layer.

According to other embodiments of the present invention there is provided a hemostatic or sealing dressing which comprises: (i) a gelatin layer; (ii) a transglutaminase layer adjacent to the gelatin layer; wherein the transglutaminase layer is coextensive or noncoextensive with the gelatin layer.

According to other embodiments of the present invention there is provided a hemostatic or sealing dressing which comprises: (i) a resorbable or non-resorbable material layer; (ii) a gelatin layer adjacent to the material layer; (iii) a transglutaminase layer adjacent to the gelatin layer; wherein the transglutaminase layer is coextensive or noncoextensive with the gelatin layer.

According to other embodiments of the present invention there is provided a hemostatic or sealing dressing which comprises: (i) a gelatin layer; (ii) a resorbable or non-resorbable material layer adjacent to the first gelatin layer; (iii) a transglutaminase layer adjacent to the material layer; wherein the transglutaminase layer is coextensive or noncoextensive with the gelatin layer.

Optionally, the dressing further comprises a backing material.

According to other embodiments of the present invention there is provided a hemostatic or sealing device which comprises: (i) a resorbable or non-resorbable matrix; (ii) gelatin; (iii) a transglutaminase; wherein the gelatin and transglutaminase are incorporated within the matrix.

According to other embodiments of the present invention there is provided a hemostatic or sealing device which comprises: (i) a porous resorbable or non-resorbable matrix; (ii) gelatin; (iii) a transglutaminase; wherein the gelatin and transglutaminase are adhered to the matrix.

According to other embodiments of the present invention there is provided a medical device for insertion into a body of a human or lower mammal, comprising a hemostatic or sealing agent or composition as described herein. Preferably the device comprises a vascular catheter.

According to other embodiments of the present invention there is provided a medical device for topical application on the body of a human or lower mammal, comprising a hemostatic or sealing agent or composition as described herein. Optionally the device comprises a pressurized spray or foam.

It is to be understood that both the foregoing general description and the following detailed description are exemplary and explanatory only and are intended to provide further explanation of the invention as claimed.

Unless defined otherwise, all technical and scientific terms used herein have the same meaning as is commonly understood by one of skill in the art to which this invention belongs. All patents, patent applications, and publications mentioned herein are incorporated herein by reference.

As used herein, a transglutaminase layer that is said to be "noncoextensive" with a gelatin layer is one in which the spatial boundaries of the transglutaminase layer in two dimensions are smaller than the spatial boundaries of one or both gelatin layers such that the transglutaminase layer is coextensive with only about 5% to about 95% of the surface area of the first gelatin layer of the hemostatic dressing and/or coextensive with only about 5% to about 95% of the surface layer of the second gelatin layer of the hemostatic dressing, independently. For example, the transglutaminase layer can be coextensive with about 10, 20, 30, 40, 50, 60, 70, 75, 80, or 90% of the surface area of each of the first and second gelatin layers, independently. A transglutaminase layer that is "coextensive" with a gelatin layer provides full coverage of the gelatin layer and is coextensive with 100% of the surface area of the gelatin layer. A transglutaminase layer can be noncoextensive with the first gelatin layer and yet be coextensive with the second gelatin layer, or vice versa, e.g., by employing gelatin layers having different total surface areas or shapes.

"Patient" as used herein refers to human or animal individuals in need of medical care and/or treatment.

"Wound" as used herein refers to any damage to any tissue of a patient that results in the loss of blood from the circulatory system or the loss of any other bodily fluid from its physiological pathway. The tissue can be an internal tissue, such as an organ or blood vessel, or an external tissue, such as the skin. The loss of blood or bodily fluid can be internal, such as from a ruptured organ, or external, such as from a laceration. A wound can be in a soft tissue, such as an organ, or in hard tissue, such as bone. The damage may have been caused by any agent or source, including traumatic injury, infection or surgical intervention. The damage can be life-threatening or non-life-threatening.

"Resorbable material" as used herein refers to a material that is broken down spontaneously and/or by the mammalian body into components which are consumed or eliminated in such a manner as not to interfere significantly with wound healing and/or tissue regeneration, and without causing any significant metabolic disturbance.

"Stability" as used herein refers to the retention of those characteristics of a material that determine activity and/or function.

"Binding agent" as used herein refers to a compound or mixture of compounds that improves the adherence of one layer of the hemostatic dressing to one or more different layers and/or the adherence of the components of a given layer to other components of that layer.

"Solubilizing agent" as used herein refers to a compound or mixture of compounds that improves the dissolution of a protein or proteins in a (preferably) aqueous solvent.

"Filler" as used herein refers to a compound or mixture of compounds that provide bulk and/or porosity to one or more layers of the hemostatic dressings.

"Release agent" as used herein refers to a compound or mixture of compounds that facilitates removal of an hemostatic dressing from a manufacturing mold.

"Foaming agent" as used herein refers to a compound or mixture of compounds that produces gas when hydrated under suitable conditions.

"TG" refers to transglutaminase of any type; "mTG" may also refer to microbial transglutaminase and/or to any type of transglutaminase, depending upon the context (in the specific experimental Examples below, the term refers to microbial transglutaminase).

The term "mammal", particularly with regard to method of treatment and/or use or application of a device and/or composition, refers to both humans and lower mammals, unless otherwise specified.

As used herein, "about" means plus or minus approximately ten percent of the indicated value.

Other features and advantages of the invention will be apparent from the following detailed description, and from the claims.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 8 is a photograph showing the formation of the gel and also induction of hemostasis (FIG. 8A shows the entire area while FIG. 8B shows a portion of the area, magnified for further details);

FIG. 9A shows lack of clot formation after application of control solution, while

DETAILED DESCRIPTION OF THE INVENTION

Figure 1:
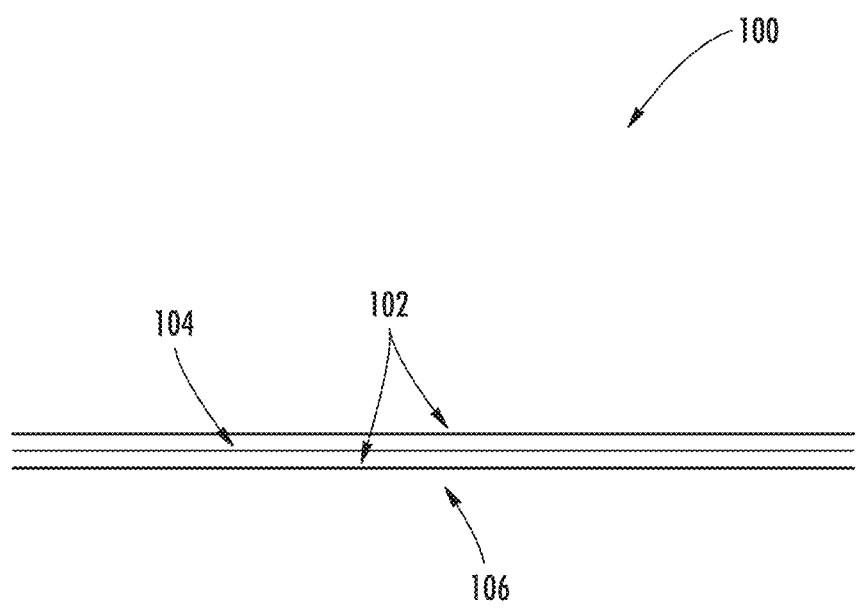
FIG. 1 is a schematic block diagram of an exemplary bandage according to the present invention.

The present invention is of an adhesive material which comprises a cross-linkable protein and a non-toxic material which induces cross-linking of the cross-linkable protein. Preferably, the cross-linkable protein includes gelatin and any gelatin variant or variant protein as described herein. Optionally and preferably, the non-toxic material comprises transglutaminase (TG), which may optionally comprise any type of calcium dependent or independent transglutaminase (mTG), which may for example optionally be a microbial transglutaminase. According to some embodiments of the present invention, the adhesive material is provided in a bandage, which is preferably adapted for use as a hemostatic bandage. Various embodiments of the present invention are described in greater detail below, under section headings which are provided for the sake of clarity only and without any intention of being limiting in any way.

Gelatin and Transglutaminase

According to preferred embodiments of the present invention, there is provided a composition for hemostasis and tissue sealing in which the cross-linking material comprises transglutaminase and the cross-linkable protein comprises gelatin.

According to a preferred embodiment, transglutaminase is present in a composition having a specific activity level of at least about 100 U/gm, although optionally lower activity levels may also be used, for example by optionally adjusting the above described ratios. Such optionally lower activity levels of the composition preferably comprise at least about 20 U/gm, more preferably at least about 40 U/gm, even more preferably at least about 60 U/gm and most preferably at least about 80 U/gm.

The transglutaminase, whether alone or as part of a composition, is preferably added to gelatin in an amount such that the resulting transglutaminase activity in the mixture is preferably from about 25 to about 100 U/g of gelatin and more preferably from about 40 to about 60 U/g of gelatin.

Suitable gelatin and transglutaminase can be obtained by any of the methods known and available to those skilled in the art. Gelatin may optionally comprise any type of gelatin which comprises protein that is known in the art, preferably including but not limited to gelatin obtained by partial hydrolysis of animal tissue and/or collagen obtained from animal tissue, including but not limited to animal skin, connective tissue (including but not limited to ligaments, cartilage and the like), antlers or horns and the like, and/or bones, and/or fish scales and/or bones or other components; and/or a recombinant gelatin produced using bacterial, yeast, animal, insect, or plant systems or any type of cell culture.

According to preferred embodiments of the present invention, gelatin from animal origins preferably comprises gelatin from mammalian origins and more preferably comprises one or more of pork skins, pork and cattle bones, or split cattle hides, or any other pig or bovine source. More preferably, such gelatin comprises porcine gelatin since it has a lower rate of anaphylaxis. Gelatin from animal origins may optionally be of type A (Acid Treated) or of type B (Alkaline Treated), though it is preferably type A.

Preferably, gelatin from animal origins comprises gelatin obtained during the first extraction, which is generally performed at lower temperatures (50-60° C., although this exact temperature range is not necessarily a limitation). Gelatin produced in this manner will be in the range of 250-300 bloom and has a high molecular weight of at least about 95-100 kDa. Preferably, 300 bloom gelatin is used.

A non-limiting example of a producer of such gelatins is PB Gelatins (Tessenderlo Group, Belgium).

According to some embodiments of the present invention, gelatin from animal origins optionally comprises gelatin from fish. Optionally any type of fish may be used, preferably a cold water variety of fish such as carp, cod, or pike, or tuna. The pH of this gelatin (measured in a 10% solution) preferably ranges from 4-6.

Cold water fish gelatin forms a solution in water at 10° C. and thus all cold water fish gelatin are considered to be 0 bloom. For the current invention, a high molecular weight cold water fish gelatin is preferably used, more preferably including a molecular weight of at least about 95-100 kDa. This is equivalent to the molecular weight of a 250-300 bloom animal gelatin. Cold water fish gelatin undergoes thermoreversible gelation at much lower temperatures than animal gelatin as a result of its lower levels of proline and hydroxyproline. Per 1000 amino acid residues, cold water fish gelatin has 100-130 proline and 50-75 hydroxyproline groups as compared to 135-145 proline and 90-100 hydroxyproline in animal gelatins (Haug I J, Draget K I, Smidsrød O. (2004). Food Hydrocolloids. 18:203-213).

A non-limiting example of a producer of such a gelatin is Norland Products (Cranbury, N.J.).

In a preferred embodiment of the invention, the gelatin is purified to remove salts. This can be accomplished according to previously described techniques. One such technique involves forming a 20% w/v solution of gelatin in water and heating it to 60° C. under stirring. The mixture is then let to stand still overnight. The gel obtained is dialysed against repeated changes of deionized water to eliminate salts, stirred and heated to 50° C. to disaggregate the physical network. The final solution was filtered and freeze-dried. (Crescenzi V, Francescangeli A, Taglienti A. (2002). Biomacromolecules. 3:1384-1391). Alternatively, the gelatin can be desalted by size exclusion column.

According to some embodiments of the present invention, a recombinant gelatin is used. Recombinant gelatins are currently commercially produced by FibroGen (San Francisco, Calif.). The currently preferred method is using a recombinant yeast system (*Pichia Pastoris*) to express specified fragments of Type I, alpha1 human sequence collagen.

In an optional but preferred embodiment of the present invention, recombinant gelatins are fully synthetic molecules, containing no contaminating components from humans or any animals. By "synthetic" it is meant that the gelatin is preferably produced according to a method selected from chemical synthesis, cell free protein synthesis, cell tissue culture, any type of bacterial, insect or yeast culture, or in plants. The use of synthetic gelatins eliminates many of the variables and drawbacks associated with tissue-derived materials, including provoking unwanted immune responses. For example, fish gelatins demonstrate high allergenicity and animal gelatins demonstrate low-moderate allergencity, while recombinant gelatins can have zero allergenicity. In human safety studies, no adverse events related to recombinant gelatin were found.

Methods of creating recombinant gelatins and the benefits of their use are fully described in U.S. Pat. Nos. 6,413,742 and 6,992,172, which are hereby incorporated by reference as if fully set forth herein.

Recombinant gelatins can be produced to be highly (99%) purified. Recombinant gelatin production allows for the optional production of gelatins with at least one defined and predetermined characteristic, including but not limited to defined molecular weights, pI (isoelectric point), guaranteed lot-to-lot reproducibility, and the ability to tailor the molecule to match a specific application.

An example of tailoring a molecule to match a specific application has been previously described wherein a gelatin was created to be highly hydrophilic (Werten M W T, et al. (2001). Protein Engineering. 14 (6): 447-454). Optionally and preferably a gelatin according to the present invention comprises a gelatin having at least one adjusted, tailored or predetermined characteristic.

Non-limiting examples of other types of characteristics which may optionally be so tailored according to the present invention include undergoing or not undergoing thermoreversible gelation. Recombinant gelatins can be created to undergo thermoreversible gelation or not undergo thermoreversible gelation. A gelatin that has one or more beneficial characteristics of natural animal gelatin but does not undergo thermoreversible gelation has tremendous amount of utility in enabling the cross-linking of gelatin by other means at temperatures at which it would normally undergo thermoreversible gelation. Such a gelatin is also encompassed by some embodiments of the present invention.

Animal (bovine, porcine and so forth) gelatin, warm water fish gelatin, and recombinant gelatin (gelling type) can undergo thermoreversible gelation somewhere between 35-40 degrees, particularly at high molecular weights and/or high concentrations (>20%) and/or with modification(s) and/or one or more additional materials (see below for a description). At room temperature, they are in gel form and cannot easily mix with mTG. Various modifications of a composition according to some embodiments of the present invention are described below to maintain the gelatin solutions in liquid form at room temperature.

Cold water fish gelatin and recombinant gelatin (non-gelling type) do not form thermoreversible gels at room temperature, even without further modification and/or the presence of one or more additional materials. They have transition points far below room temperature. At room temperature, they stay in solution and can react with mTG without further modification.

According to preferred embodiments of the present invention with regard to recombinant gelatin, a suitable in vitro culturing system is used to produce the recombinant gelatin. In addition to the use of recombinant methylotrophic yeast systems for the production of recombinant gelatin, other organisms have been used.

Recombinant, gelatin-like proteins have been expressed in *Escherichia coli* though expression levels usually obtained in *E. coli* are rather low and purification of the intracellularly produced protein can be difficult. *Bacillus brevis* has been used for the expression of gelatin-like proteins wherein sequence stretches were selected from natural collagen genes and polymerized to form semi-synthetic gelatin (Werten M W T, et al. Secreted production of a custom-designed, highly hydrophilic gelatin in *Pichia pastoris*. Protein Engineering, Vol. 14, No. 6, 447-454, June 2001).

Additional successful efforts at producing recombinant gelatin have included the production of recombinant gelatin using mammalian and insect cells. Collagen and gelatin have also been expressed in transgenic tobacco plants, transgenic mice. A transgenic silkworm system has been used to produce a fusion protein containing a collagenous sequence. These systems lack sufficient endogenous prolyl hydroxylase activity to produce fully hydroxylated collagen, which can be overcome by over-expression of prolyl hydroxylase (Olsen D, et al. Recombinant collagen and gelatin for drug delivery. Adv Drug Deliv Rev. 2003 November 28; 55(12):1547-67). Plant based systems may also optionally be used; for example a collaboration between Iowa State University and Fibrogen is developing the expression of gelatin in transgenic corn.

The gelatin employed in the hemostatic dressing can be a gelatin complex or any gelatin, or a derivative or metabolite thereof, or a gelatin produced according to a single process or a plurality of processes. For example, the gelatin may optionally comprise gelatin type A or gelatin type B, or a combination thereof.

The transglutaminase may optionally comprise any plant, animal, or microbe derived transglutaminase, preferably other than blood derived Factor XIII. Preferably, microbial transglutaminase derived from *Streptoverticillium mobaraensis* is used.

The transglutaminase may optionally be in a composition comprising at least one other substance, such as a stabilizer or filler for example. Non-limiting examples of such materials include maltodextrin, hydrolyzed skim milk protein or any other protein substance, sodium chloride, safflower oil, trisodium phosphate, sodium caseinate or lactose, or a combination thereof.

Although the optimal pH for activity of crude transglutaminase is 6.0, it also functions with high activity in the range of pH 5.0 to pH 8.0. Therefore, a composition according to the present invention for hemostasis preferably has a pH value in a range of from about 5 to about 8.

Transglutaminase features a negative temperature coefficient. Over the temperature range of the transglutaminase activity, it takes a shorter time to react at higher temperatures and longer amount of time to start functioning at lower temperatures. The following table shows different reaction times at different temperatures comparing the same reaction grade as the reaction at 50° C., pH 6.0 that occurs in 10 minutes:

TABLE 1 reaction temperature of transglutaminase

| Temperature | 5° C. | 15° C. | 20° C. | 30° C. | 40° C. |
|---|---|---|---|---|---|
| Time (minutes) | 240 | 105 | 70 | 35 | 20 |

Non-limiting examples of commercially available transglutaminase products include those produced by Ajinomoto Co. (Kawasaki, Japan). A preferred example of such a product from this company is the Activa TG-TI (In Europe: Activa WM)—Ingredients: mTG and maltodextrin; Activity: 81-135 U/g of Activa. Other non-limiting examples of suitable products from this company include Activa TG-FP (ingredients: hydrolyzed skim milk protein, mTG; activity: 34-65 U/g of Activa TG-FP); Activa TG-GS (ingredients: sodium chloride, gelatin, trisodium phosphate, maltodextrin, mTG, and safflower oil (processing aid); activity: 47-82 U/g of Activa TG-GS); Active TG-RM (In Europe: Activa EB)—ingredients: sodium caseinate, maltodextrin, and mTG; activity: 34-65 U/g of Activa; Activa MP (ingredients: mTG, Lactose and Maltodextrin; activity: 78-126 U/g of Activa).

Other non-limiting examples of commercially available transglutaminase products include those produced by Yiming Biological Products Co. (Jiangsu, China). A preferred example of such a product from this company is the TG-B (ingredients: 1% mTG, 99% co-protein; activity: 80-130 U/g of TG-B). Other non-limiting examples of suitable products from this company include TG-A (ingredients: 0.5% mTG, 99.5% co-protein; activity: 40-65 U/g of TG-A).

For both examples, preferred transglutaminase products are those with the highest specific activity and simplest co-ingredients, as they are believed (without wishing to be limited by a single hypothesis) to have the best reactivity upon application and a lower potential for undesired side effects.

In another embodiment, a transglutaminase may optionally be extracted from *Streptoverticillium Baldaccii* or a *Streptomyces Hygroscopicus* strain to produce enzyme variants that have been shown to function optimally at lower temperatures (approximately 37° C. and 37° C.-45° C., respectively) (Negus S S. A Novel Microbial Transglutaminase Derived From *Streptoverticillium Baldaccii*. PhD Thesis. School of Biomolecular and Biomedical Science. Griffith University, Queensland, Australia and Cui L et al. Purification and characterization of transglutaminase from a newly isolated *Streptomyces hygroscopicus*. 2007: 105(2). p. 612-618.). Higher specific activity at lower temperatures is desirable for achieving faster and stronger cross linking of the gelatin under ambient conditions.

According to some embodiments, transglutaminase can be used in the form of any of the above described compositions, optionally including any of the commercially available mixtures that include transglutaminase.

In another embodiment, any of the above transglutaminase mixtures may optionally be purified by means of gel filtration, cation-exchange chromatography, hollow fiber filtration, or tangential flow filtration to remove their carrier proteins and/or carbohydrates. Some of these methods have been previously described (Bertoni F, Barbani N, Giusti P, Ciardelli G. Transglutaminase reactivity with gelatine: perspective applications in tissue engineering Biotechnol Lett (2006) 28:697-702) (Broderick E P, et al. Enzymatic Stabilization of Gelatin-Based Scaffolds J Biomed Mater Res 72B: 37-42, 2005). The filter pore size used for filtration is preferably approximately 10 kDA.

Regardless, the activity of transglutaminase is preferably measured prior to use and/or manufacture of a composition according to the present invention with a transglutaminase reactivity assay. Such an assay may optionally include but is not limited to the Hydroxamate Method, Nessler's Assay, a Colorimetric Assay, or any other assay of transglutaminase activity (see for example Folk J E, Cole P W. Transglutaminase: mechanistic features of the active site as determined by kinetic and inhibitor studies. Biochim Biophys Acta. 1966; 122:244-64; or the Nessler Assay as described in: Bertoni F, Barbani N, Giusti P, Ciardelli G. Transglutaminase reactivity with gelatine: perspective applications in tissue engineering Biotechnol Lett (2006) 28:697-702).

In general, the purity and/or quality of the gelatin and/or the transglutaminase for use in the hemostatic composition will be of an appropriate purity known to one of ordinary skill in the relevant art to lead to efficacy and stability of the protein.

Proteins for Cross-Linking Substrates Other than Gelatin

As noted above, the cross-linkable protein preferably comprises gelatin but may also, additionally or alternatively, comprise another type of protein. According to some embodiments of the present invention, the protein is also a substrate for transglutaminase, and preferably features appropriate transglutaminase-specific polypeptide and polymer sequences. These proteins may optionally include but are not limited to synthesized polymer sequences that independently have the properties to form a bioadhesive or polymers that have been more preferably modified with transglutaminase-specific substrates that enhance the ability of the material to be cross-linked by transglutaminase. Non-limiting examples of each of these types of materials are described below.

Synthesized polypeptide and polymer sequences with an appropriate transglutaminase target for cross-linking have been developed that have transition points preferably from about 20 to about 40° C. Preferred physical characteristics include but are not limited to the ability to bind tissue and the ability to form fibers. Like gelling type gelatins (described above), these polypeptides may optionally be used in compositions that also feature one or more substances that lower their transition point.

Non-limiting examples of such peptides are described in U.S. Pat. Nos. 5,428,014 and 5,939,385, both filed by ZymoGenetics Inc, both of which are hereby incorporated by reference as if fully set forth herein. U.S. Pat. No. 5,428,014 describes biocompatible, bioadhesive, transglutaminase cross-linkable polypeptides wherein transglutaminase is known to catalyze an acyl-transfer reaction between the γ-carboxamide group of protein-bound glutaminyl residues and the ε-amino group of Lys residues, resulting in the formation of ε-(γ-glutamyl)lysine isopeptide bonds.

For example, polypeptides having 13-120 amino acid residues are described, comprising a segment of the formula S1-Y-S2, wherein: S1 is Thr-Ile-Gly-Glu-Gly-Gln; Y is a spacer peptide of 1-7 amino acids or not present; and S2 is Xaa-Lys-Xaa-Ala-Gly-Asp-Val. Optionally, the spacer peptide Y is Gln-His-His-Leu-Gly, Gln-His-His-Leu-Gly-Gly or His-His-Leu-Gly-Gly. Also optionally, Xaa, amino acid 1, of S2 is Ala or Ser. Optionally, the spacer peptide comprises His-His-Leu-Gly. Optionally and preferably, at least one of Y and S2 are free of Gln residues. Optionally, the carboxyl terminal amino acid residue of the polypeptide is Pro or Gly. Specific non-limiting examples of the polypeptides include the following: Thr-Ile-Gly-Glu-Gly-Gln-Gln-His-His-Leu-Gly-Gly-Ala-Lys-Gln-Ala-Gly-Asp-Val, Thr-Ile-Gly-Glu-Gly-Gln-Gln-His-His-Leu-Gly-Ala-Lys-Gln-Ala-Gly-Asp-Val, Thr-Ile-Gly-Glu-Gly-Gln-His-His-Leu-Gly-Gly-Ala-Lys-Gln-Ala-Gly-Asp-Val, or Leu-Ser-Gln-Ser-Lys-Val-Gly. The patent also describes high molecular weight, biocompatible, bioadhesive, transglutaminase-cross-linkable copolymers and homopolymers involving these peptides.

U.S. Pat. No. 5,939,385 describes biocompatible, bioadhesive transglutaminase cross-linkable polypeptides. These polypeptides preferably have about 9-120 amino acid residues comprising a segment of the formula S1-Y-S2, wherein: S1 is selected from the group consisting of Ile-Gly-Glu-Gly-Gln, Gly-Glu-Gly-Gln, Glu-Gly-Gln, and Gly-Gln; Y is His-His-Leu-Gly-Gly or His-His-Leu-Gly; and S2 is selected from the group consisting of Ala-Lys-Gln-Ala-Gly-Asp, Ala-Lys-Gln-Ala-Gly, Ala-Lys-Gln-Ala, Ala-Lys-Gln, Ala-Lys-Ala-Gly-Asp-Val, Ala-Lys-Ala and Ala-Lys, wherein said polypeptide has an amino-terminus and a carboxy-terminus and is cross-linkable by a transglutaminase. A preferred polypeptide is Gly-Gln-His-His-Leu-Gly-Gly-Ala-Lys-Gln. Also preferred is a polypeptide wherein the polypeptide is flanked on either or both the amino-terminus and the carboxy-terminus by an elastomeric polypeptide. It further provides an elastomeric polypeptide wherein the elastomeric polypeptide is a pentapeptide or a tetrapeptide, particularly a flanked polypeptide wherein the flanking elastomeric polypeptide is Val-Pro-Gly-Val-Gly, Ala-Pro-Gly-Val-Gly, Gly-Val-Gly-Val-Pro, Val-Pro-Gly-Gly or any portion thereof, preferably such that the amino-terminus of the flanked polypeptide is Val and the carboxy-terminus of the flanked polypeptide is Gly. The patent also describes high molecular weight, biocompatible, bioadhesive, transglutaminase-cross-linkable copolymers and homopolymers involving these peptides.

These patents recognize the utility of the described peptides and polymers for use as tissue adhesives, in wound closure, and in various other medical applications. However, both patents note that the desired transition points of these peptides and polymer are 20-40° C. and recognize the need to lower the transition point so that the peptide/polymer will be able to react with transglutaminase in a wound site. Both patents state: "The transition temperature of the polymer can be adjusted by the number of polypeptides polypeptide monomers capable of being cross-linked by a transglutaminase. As will be appreciated by one skilled in the art, for clinical applications, reduction of the transition temperature at the time of application will facilitate the rapid solidification of the matrix at the wound site."

Naturally, in order to ensure the maximal cohesive and adhesive strength of a cross-linked polymer intended for use as a bioadhesive, it is frequently not possible to remove cross-linkable monomers. In fact, to maximize the cohesive and adhesive strengths of such adhesives, it is generally preferable to add more cross-linkable monomer substrates. Thus, the bioadhesive potential of the polymers described in these patents is significantly limited by the transition temperature of the polymer solution.

Preferred embodiments of the present invention significantly advance the utility of these polypeptides or polymers for use in hemostatic, tissue adhesive, and tissue sealant applications. For example, optional embodiments are described below for lowering the transition point of polymers that gel at room temperature. These strategies can be utilized in lowering the transition point of the peptide sequences and polymers described in these patents.

Also as described in greater detail below, preferably the amount of these polymers differs for embodiments of the present invention, as opposed to the original uses described in the above patents (which neither teach nor suggest any of the uses described herein for the present invention). For example, the polymer concentration ranges taught in these patents for use in a tissue adhesive kit are 5 to 100 mg/ml and preferably 35 to 50 mg/ml. Some embodiments of the present invention comprise higher polymer concentrations, for example in the range of 150-250 mg/ml. Higher transglutaminase concentrations are also preferred for some embodiments of the present invention.

Other synthetic substrates may also optionally be provided according to some embodiments of the present invention. Preferably short transglutaminase substrates are synthesized and then connected and/or bound to large polymer molecules. The transglutaminase substrates are generally very short (<20 amino acid residues). The solubility and transition point of such substrates is dependent on the polymer to which the substrate is attached. For example, if the substrate is attached to gelling gelatin, then a solution of this newly synthesize molecule would require the addition of another substance to stay in liquid form at room temperature.

A non-limiting example of this type of material is described in U.S. Pat. No. 7,208,171, which is hereby incorporated by reference as if fully set forth herein, which describes the rational design of transglutaminase substrate peptides. The design strategy was based on maximizing the number of available acyl acceptor lysine-peptide substrates and acyl donor glutaminyl-peptide substrates available for transglutaminase cross-linking. Beyond this, the Lys and Glu substrate peptides were designed to possess basic features of known biomacromolecular and synthetic peptide substrates of transglutaminase. For example, the Glu substrate peptides contained 2-5 contiguous Glu residues, based on evidence that peptides become better transglutaminase substrates with increasing length of Glu repeats (Gorman, J. J.; Folk, J. E. J. Biol. Chem. 1980, 255, 419-427. & Kahlem, P.; Terre, C.; Green, H.; Djian, P. Proc. Natl. Acad. Sci. U.S.A. 1996, 93, 14580-14585.) and that proteins containing two or more adjacent Glu residues are known to be good substrates. (Etoh, Y.; Simon, M.; Green, H. Biochem. Biophys. Res. Commun 1986, 136, 51-56. & Hohenadl, C.; Mann, K.; Mayer, U.; Timpl, R.; Paulsson, R.; Aeschlimann, D. J. Biol. Chem. 1995, 270, 23415-23420.) A Leu residue was placed adjacent to the Glu near the C-terminus in several peptides, because this has been shown to result in a significant increase in Glu specificity. (Gross, M.; Whetzel, N. K.; Folk, J. E. J. Biol. Chem. 1975, 250, 4648-4655.) Regarding the Lys substrate peptides, it has been shown that the composition and sequence of the amino acids adjacent to lysine residues in peptide and protein substrates can have an effect on the amine specificity. (Groenen, P.; Smulders, R.; Peters, R. F. R.; Grootjans, J. J.; Vandenijssel, P.; Bloemendal, H.; Dejong, W. W. Eur. J. Biochem. 1994, 220, 795-799. & Grootjans, J. J.; Groenen, P.; Dejong, W. W. J. Biol. Chem. 1995, 270, 22855-22858.). Finally, in all peptides a Gly residue was added on the C-terminal side to act as a spacer between the peptide and the polymer in the peptide-polymer conjugates, so that the peptide in the conjugate may be more accessible to enzyme.

Transglutaminase specificity assays of the peptides described in this patent demonstrated that they successfully created acyl acceptor and acyl donor substrates with high transglutaminase binding specificity. It is suggested in the patent that these substrates can be covalently conjugated to PEG, dendrimers, chitosan, gelatin, soluble collagens, hyaluronic acid, alginates, and albumins. The patent goes on to suggest that such polymer-peptide conjugates in solution or liquid form could be used a surgical sealants and/or medical adhesives.

Although this patent describes highly specific transglutaminase-cross-linkable peptide substrates, it does not teach or suggest the advanced application methods or material modifications described as part of the present invention, nor does it teach or suggest the compositions of the present invention. The taught substrates of the patent however, may optionally be useful in enhancing a bioadhesive created through transglutaminase cross-linking or in creating such a bioadhesive from an otherwise non-transglutaminase-specific polymer. These substrates would need to be combined with one or more other proteins or scaffolds as described herein to be useful for the present invention.

Cross-Linking Materials Other than Transglutaminase

As noted above, the cross-linking material preferably comprises transglutaminase but may also, additionally or alternatively, comprise another type of cross-linking material.

Non-limiting examples of such cross-linking agents include carbodiimides such as N,N-(3-(dimethylamino)propyl)-N-ethyl carbodiimide (EDC), N-hydroxysuccinimide (NHS) with EDC, or carbodiimides used together with poly(L-glutamic acid) (PLGA) and polyacrylic acid. In another embodiment, such cross-linking agents can include Tyrosinase or Tyrosinase with chitosan. In another embodiment, cross-linking (polymerization) is photo-initiated with ultraviolet light or γ-rays. In another embodiment, cross-linking agents can include alkylene, citric acid (carbonic acid), or Nano-hydroxyapataite (n-HA)+poly(vinyl alcohol) (PVA).

In another embodiment, a cross-linking agent is a plant-derived polyphenol such as (i.e. hydroxylated cinnamic acids, such as caffeic acid (3,4-dihydroxycinnamic acid), chlorogenic acid (its quinic acid ester), caftaric acid (its tartaric acid ester), and flavonoids (i.e. as quercetin and rutin). In another embodiment, the additional cross-linking agent is an oxidized mono or disaccharide, oxo-lactose, or a dialdehyde based on a sugar moiety (galacto-hexodialdose) (GALA). In another embodiment, Genipin or other iridoid glycoside derivative, or Secoiridoids, preferable oleuropein, comprises the cross-linking agent. In another embodiment, the cross-linking agent is a thiol-reactive poly(ethylene glycol). In another embodiment, the cross-linking agent is dextran, oxidized dextran, dextran dialdehyde. In another embodiment, the cross-linking agent is a multi-copper oxidase such as laccase or bilirubin oxidase.

Illustrative Compositions

The above described cross-linking substrates and cross-linking materials may optionally be combined with one or more additional materials to form various compositions according to the present invention. According to some embodiments, the adhesive material optionally and preferably comprises: (i) gelatin; (ii) a transglutaminase; wherein the gelatin and transglutaminase are formed into particles either separately or together. More preferably, the gelatin and transglutaminase are provided in sufficient quantities to be useful as a sealing, hemostatic agent.

Various amounts of each and their ratios were previously described. The transglutaminase content may optionally be increased to increase the rate of reaction or decreased to enhance safety. According to some embodiments of the present invention, a 15-30% solution of gelatin is preferably applied, followed by a 15-30% solution of transglutaminase.

In addition, one or more supplements can also be contained in the hemostatic product, e.g., drugs such as growth factors, polyclonal and monoclonal antibodies and other compounds. Illustrative examples of such supplements include, but are not limited to: antibiotics, such as tetracycline and ciprofloxacin, amoxicillin, and metronidazole; anticoagulants, such as activated protein C, heparin, prostracyclin (PGI2), prostaglandins, leukotrienes, antitransglutaminase III, ADPase, and plasminogen activator; steroids, such as dexamethasone, inhibitors of prostacyclin, prostaglandins, leukotrienes and/or kinins to inhibit inflammation; cardiovascular drugs, such as calcium channel blockers, vasodilators and vasoconstrictors; chemoattractants; local anesthetics such as bupivacaine; and antiproliferative/anti-tumor drugs such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as alpha- or beta- or gamma-Interferon, alpha- or beta-tumor necrosis factor, and interleukins; colony stimulating factors; erythropoietin; antifungals, such as diflucan, ketaconizole and nystatin; antiparasitic agents, such as pentamidine; anti-inflammatory agents, such as alpha-1-anti-trypsin and alpha-1-antichymotrypsin; anesthetics, such as bupivacaine; analgesics; antiseptics; and hormones. Other illustrative supplements include, but are not limited to: vitamins and other nutritional supplements; glycoproteins; fibronectin; peptides and proteins; carbohydrates (both simple and/or complex); proteoglycans; antiangiogenins; antigens; lipids or liposomes; and oligonucleotides (sense and/or antisense DNA and/or RNA).

According to some preferred embodiments of the present invention, there is provided a composition which features gelatin that undergoes thermoreversible cross-linking (as described above, some but not all types of gelatin undergo thermoreversible cross-linking without modification and/or the use of one or more additional materials). Thermoreversible gelation of animal gelatin occurs when a gelatin solution is cooled below approximately body temperature (37° C.). In gelatin-mTG mixtures at room temperature, this gelation traps the mTG in a thermoreversible gel and prevents it from reacting with the gelatin to form an irreversible sealing gel. As operating room temperature is generally maintained at 22° C., thermoreversible gelation of a gelatin solution will occur rather rapidly in a clinical setting if it is not continuously heated. This presents a problem in the application of a gelatin-mTG mixture for hemostasis since the gelatin solution has to be heated prior to its mixture with mTG. Having to heat the gelatin immediately prior to application is undesirable from both a logistical and safety standpoint as a heating element would need to be added to the sensitive operating room environment for example; in emergency situations and/or urgent medical care situations outside of operating rooms, such a requirement for heating is even more problematic.

Aside from its hindrance to tissue adhesion and hemostasis, the inability of gelatin to form a solution at room temperature and mix with microbial transglutaminase also presents difficulties for other potential applications of the gelatin-mTG mixture. For example, while gelatin-mTG gels have been used as scaffolds for cell encapsulation in tissue engineering, extreme care has had to be taken to ensure that the gelatin solution had sufficiently cooled prior to encapsulation of the cells. Furthermore, implantation of encapsulated cells is quite complicated as thermoreversible gelation of the gelatin occurs before the gelatin-mTG mixture can be safely implanted in the body. A similar problem exists with regard to local drug delivery wherein the efficacy of certain drugs could be harmed by coming into contact with heated gelatin and implantation of a gelatin-mTG gel that incorporates a certain drug could be hindered by the thermoreversible gelation of gelatin.

Fortunately, cross-linking of gelatin by mTG occurs by linking the Lys and Gln amino groups (Chen et al. Biomacromolecules, Vol. 4, No. 6, 2003) whereas the amino acid groups in gelatin that are responsible for its thermoreversible gelation are Pro & Hyp (Haug et al. Food Hydrocolloids 18 (2004) 203-213). Thus, the potential exists for reducing the proclivity of gelatin for thermoreversible gelation without harming its ability to form cross-linked gels through mTG cross-linking. In other words, the solubility of the gelatin used in a gelatin-mTG mixture can be increased and its melting point lowered to allow it to form a room temperature solution with mTG without negatively affecting the cross-linked gelatin-mTG gel that is formed.

According to some embodiments of the present invention, there are provided compositions of matter of a gelatin-mTG mixture wherein the mixture is modified by one of a number of methods to increase the solubility of the gelatin and allow the gelatin to form a solution with the mTG at temperatures lower than the natural melting point of standard animal gelatin. These compositions include (i) gelatin-mTG mixtures made using standard gelatin that has been modified to reduce its melting point; (ii) gelatin-mTG mixtures that include additives that increase the solubility of gelatin in the gelatin-mTG solution itself; (iii) gelatin-mTG mixtures made using commercially available gelatin products treated to have lower transition temperatures; and (iv) gelatin-mTG mixtures that form a solution under specific, carefully controlled environmental conditions (temperature, pH, ionic concentration, etc) that lower the melting point of the gelatin.

These novel compositions greatly increase the utility of gelatin-mTG gels and enable a wide variety of applications, particularly in the medical field, that can utilize gelatin-mTG gels that can be formed by mixing gelatin at mTG at room temperature. In addition, in many cases, the gelatin and gelatin-mTG solutions formed using gelatin solutions that contain lower melting point gelatin will have the additional benefit of lowering the initial viscosity of the solution, allowing the mTG more freedom of movement and increasing the speed at which the gelatin-mTG reaction occurs.

According to some embodiments of the present invention there are also provided additional enhancements to the gelatin-mTG mixture that have the potential to improve the properties of a gelatin-mTG based product. For example, the present invention also features methods of further stabilizing the mTG in the gelatin-mTG mixture to increase its shelf life.

In another embodiment of the invention, a plasticizer is incorporated into the gelatin-mTG solution. Plasticizers have been shown to lower the melting point of gelatin, allowing it to form a solution at lower temperatures without undergoing thermoreversible gelation. One or more plasticizers are preferentially added to gelatin granules or to a gelatin solution to lower its melting point prior to the mixture of the gelatin solution with mTG or mTG solution. In a situation where the gelatin and mTG solutions are lyophilized, one or more plasticizers are added to the gelatin solution prior to its lyophilization. In an alternate embodiment, as described above, one or more plasticizers is added to the gelatin solution, allowing for the addition of mTG at a lower temperature, at which mTG is not highly reactive. The gelatin-mTG-plasticizer solution can then be lyophilized or otherwise dried in an already mixed form.

In a preferred embodiment, a polyhydric alchohol, or polyol, is used as the plasticizer. Such polyols include glycerine, glycerol, xylitol, sucrose, and sorbitol. Sorbitol makes gelatin-mTG gels more elastic and sticky. Glycerol makes gelatin-mTG gels stiffer and accelerates mTG cross-linking of gelatin. A preferred concentration ratio range for glycerol is preferably from about 0.5:1 to about 5:1 Glycerol:Gelatin, more preferably from about 1:1 to about 2:1 Glycerol:Gelatin, weight per weight. A preferred concentration ratio range for sorbitol is preferably from about 0.5:1 to about 5:1 Sorbitol:Gelatin, more preferably from about 1:1 to about 3:1 Sorbitol:Gelatin, weight per weight.

Polyhydric alcohols have higher boiling points when compared to similar sized monohydric alcohols. The water solubilities of polyhydric alcohols are higher when compared to similar sized monohydric alcohols since there are more hydroxyl groups for water molecules to be attracted to. In the food industry, polyhydric alcohols such as glycerine are used to increase the water solubility of gelatin as described in U.S. Pat. No. 2,558,065, hereby incorporated by reference as if fully set forth herein, where a polyhydric alchohol such as glycerine is poured over gelatin granules, and U.S. Pat. No. 3,939,001, hereby incorporated by reference as if fully set forth herein, where gelatin is allowed to absorb the polyhydric alchohol for a period of time sufficient for the gelatin granules to become swollen but prior to dissolution. These techniques and the variations of these techniques described in those patents are to be considered preferential embodiments of the polyol usage described as part of the current invention.

The effects of different concentrations of the plasticizers glycerol, xylitol, sorbitol, sucrose, and trehalose on lowering the transition points of gelatin are well documented (D'Cruz N M, Bell L N. Thermal Unfolding of Gelatin in Solids as Affected by the Glass Transition. J Food Science 2005: 70(2), Kozlov P V, Burdygina G I. The structure and properties of solid gelatin and the principles of their modification. Polymer, 1983 (24): p. 651-666).

While the effect of polyhydric alcohols on the melting point of gelatin has been well documented, they have never been used, prior to the current invention, with gelatin or a gelatin solution prior to its mixture with mTG or with a gelatin-mTG solution.

In an embodiment of the addition of polyol plasticizers, a preferred range for the weight ratio of plasticizer to gelatin is preferably from about 0.5:1 to about 1:1, plasticizer: gelatin.

In another embodiment of using gelatin plasticizers to lower the melting point of gelatin in solution, the type of plasticizer used can include triethanolamine, resorcin, thiodiglycol, sodium salt of toluenesulphoacid, butylene glycol, urea nitrate, thiourea, urea, glutamic acid, aspargic acid, valine, glycine, KSCN, KI, and LiBr.

The addition of urea to gelatin solution has been previously explored and demonstrated the ability to prevent high molecular weight gelatin (99 kDa) from forming a thermoreversible gel at 25° C. (Otani Y, Tabata Y, &a& Y. Effect of additives on gelation and tissue adhesion of gelatin-poly(L-glutamic acid) mixture. Biomaterials 19 (1998) 2167-2173)

In a preferred embodiment of using urea to prevent thermoreversible gelation in gelatin or gelatin-mTG solution at temperatures below their natural melting points, urea is added to the solutions at a urea:gelatin ratio between 0.25-2.0, weight per weight. Even more preferentially, urea is added to the solutions at a urea:gelatin ratio of from about 1:2 to about 2:2, weight per weight.

In another embodiment of the present invention, the pH level and ion concentration of an aqueous solvent are modified to increase the solubility of gelatin dissolved in the solvent. The further the product pH is from the isoionic pH the better will be the solubility of the gelatin. A preferred aqueous solvent used in this technique is phosphate buffered saline (PBS). Other suitable buffers include borate, phosphate, HEPES (N-[2-Hydroxyethyl]piperazine-N'-[2-ethanesulfonic sacid]) and the like.

Generally, in compositions that are to be used within living organisms, it is preferred to dissolve gelatin in an aqueous solvent buffered at pH 5.5-9.0 and of low to moderate ionic strength (equivalent to about 1 to 1000 mM NaCl, preferably 100 to 150 mM NaCl) More preferably, the pH of the solution is about 6.0-8.0, more preferably about 7.4. Though gelatin is soluble at these pH and ion concentrations, its solubility can be increased by increasing the disparity between the solution pH and the isoionic pH of gelatin.

One or more salts may also optionally be added to lower the transition temperature of gelatin. Preferably the salts are added at a suitable concentration range for reducing the transition temperature, more preferably below room temperature. For example, the following salts at the indicated concentration ranges were found to reduce the transition point of gelatin below room temperature: Sodium Bromide (1-2 M), Sodium Nitrate(1-2 M), Sodium Thiocyanate (0.5-1.5 M), Sodium Iodide(0.5-1.5 M), Sodium Benzenesulfonate(0.5-1.5 M), Sodium Salicylate(0.25-1 M), Sodium Dichloroacetate (1-2 M), Sodium Trichloroacetate(0.5-1.5 M), Sodium Dibromoacetate(0.5-1.5 M), Sodium Tribromoacetate(0.25-1 M), Sodium Diiodoacetate (0.5-1.5 M), Sodium Acetyltryptophan (0.5-1.5 M), Sodium Acetylenedicarboxylate (1-2 M), Lithium Salicylate(1-2 M), Lithium Diiodosalicylate(0.2-1 M) (see for example Bello J, Riese H C A, Vinograd J R. Mechanism of Gelation of Gelatin. Influence of Certain Electrolytes on the Melting Points of Gels of Gelatin and Chemically Modified Gelatins. Am Chem Soc. September 1956 (60). P. 1299-1306).

Optionally and preferably, one or more acidic substances are added to the composition to decrease the pH. Lowering the pH of the gelatin solution reduces its transition point. In general, reducing the gelatin transition point is useful to reconstitute the gelatin in the body at 37 degrees. For some preferred types of gelatin used herein, as for example from mammalian sources, lowering the pH provides better results for the gelatin transition point. However, for some types of gelatin, raising the pH may optionally provide better results.

In another embodiment of increasing the pH disparity between the gelatin solution and the isoionic point of gelatin, the gelatin itself is modified. This can be accomplished by treating it prior to dissolving it in solution to create an electrostatically charged gelatin, as in U.S. Pat. No. 6,863,783, hereby incorporated by reference as if fully set forth herein, or by controlling the isoelectric point of gelatin, as in U.S. Pat. No. 2,398,004, hereby incorporated by reference as if fully set forth herein.

If the pH of the gelatin solution is raised, instead of lowered, then the pH of the solution will be closer to the isoionic point of gelatin and the transition point will be raised. This modification could optionally be used to maintain non-cross-linked gelatin as a thermoreversible gel after implantation in the body.

In another embodiment of the current invention, the gelatin, mTG, or both substances have undergone drying after being mixed with a trehalose carbohydrate or other carbohydrate to stabilize the protein or enzyme in its active form, enabling it to be reconstituted with ease. Various embodiments of drying are lyophilization, spray drying, drum drying, air drying, heated drying, vacuum drying, or any other method of drying a gelatin-trehalose or gelatin-mTG-trehalose solution.

The superior stabilizing ability of trehalose in air drying and freeze drying has been well documented. It has been shown that dried materials undergo quicker reconstitution when drying is performed after trehalose has been added to a particular material or solution (Crowe L M, Reid D S, Crowe J H. Is Trehalose Special for Preserving Dry Biomaterials? Biophysical Journal 1996 (71): 2087-2093).

The drying of protein solutions incorporating trehalose at ambient temperature and atmospheric pressure has been fully described in U.S. Pat. No. 4,891,319. In the examples described therein, the function of the dried proteins was preserved.

In the specific case of gelatin, the incorporation of trehalose into the gelatin solution has the additional benefit of increasing the strength of gelatin gels. (Norie N, Kazuhiro M, Masami N, Yusuke O, Takashi O, Keiko N. Factors Affecting the Gelation of a Gelatin Solution in the Presence of Sugar. Journal of Home Economics of Japan. 55(2): p. 159-166 (2004))

Furthermore, the gelatin-mTG cross-linking reaction bears many similarities to the cross-linking reaction of natural blood factors. Trehalose drying to stabilize blood factors has recently been demonstrated (U.S. Pat. Nos. 6,649,386 and 7,220,836) and is in the process of being used commercially to prepare products with blood proteins that can be easily reconstituted (ProFibrix™, Leiderdorp).

In another embodiment of the current invention, gelatin is dried in the presence of a sugar. This can include the spray-atomizing of gelatins on different supports such as sugar, maltodextrins, or starches.

In an optional embodiment of the current invention, a commercial gelatin product called Cryogel™ produced by PB Gelatins (Tessenderlo Group, Belgium) is used. Cryogel is soluble at temperatures 5-6° C. less than equivalent untreated gelatin. The precise treatment process used in the production of Cryogel is proprietary.

In yet another embodiment of the present invention, the composition may optionally feature one or more additional substances. For example, the composition may optionally comprise a denaturant, including but not limited to one or more of Guanidine Hydrochloride, or Urea. The composition may also optionally, alternatively or additionally, comprise a reducing agent, including but not limited to one or more of magnesium chloride or hydroquinone. The composition may also optionally, alternatively or additionally, comprise a substance such as isopropanol for increasing hydrogen bond formation. The composition may also optionally, alternatively or additionally, comprise a protic polar solvent, preferably being capable of structurally interacting with proteins and preventing helix formation in gelatin, such as DMSO (dimethylsulfoxide). The composition may also optionally, alternatively or additionally, comprise a desiccant which is exothermic upon entering solution, such as calcium chloride for example.

According to some embodiments, the present invention also features a gelatin specific protease which comprises an enzyme or enzyme mixture that can rapidly breakdown gelatin molecule strands but does not adversely affect the natural fibrin-based clotting networks.

A gelatin-specific protease could optionally be used to remove the bandage/dressing/absorbable hemostat/sealant from a wound site without damaging the natural endogenous fibrin clot and causing rebleeding. This feature is an additional benefit of the present invention as compared to existing products, and solves the technical problem that hemostatic dressings which are sufficiently adhesive to adhere well to a wound site and stop bleeding cannot be removed without removing or destroying the fibrin clot. Although at least some embodiments of a bandage according to the present invention are reabsorbable, there may be a need to remove it from a wound if the doctor wants to operate on a wound site, or put a bandage in a different place.

An exemplary non-limiting protease is proteinase K (Chen, et al. Biomacromolecules 2003, 4, 1558-1563). However, other proteases, particularly quicker acting enzymes, may be used alternatively.

According to other embodiments, one or more protease inhibitors are optionally added, including but not limited to aprotinin, transexamic acid, alpha-2 plasmin inhibitor, alpha-1 antitrypsin, or the Pittsburgh mutant of alpha-1-antitrypsin (Arg-358 alpha-1-antitrypsin; see Owen et al. N. Engl. J. Med. 309: 694-698, 1983 and U.S. Pat. No. 4,711,848, which is hereby incorporated by reference as if fully set forth herein). Within a preferred embodiment, aprotinin is included in an amount sufficient to provide a final working concentration of 1500-20,000 KIU/mL.

According to other embodiments, the hemostatic material of the present invention may further comprise an additional hemostatic substance, in addition to gelatin and TG. Such a substance can be biological or synthetic in nature and can include but is not limited to one or more known hemostatic agents such as albumin, collagen, fibrin, thrombin, chitosan, ferric sulfate, or other metal sulfates.

According to still other embodiments, the hemostatic material of the present invention may further comprise an accelerant for accelerating the rate of cross-linking upon combining the cross-linking material, such as transglutaminase for example, and gelatin. Such an accelerant may optionally comprise calcium for example.

Calcium is a preferred component of the transglutaminase/gelatin cross-linking reaction. Various studies have demonstrated that varying calcium concentrations and/or the addition of calcium-mobilizing drugs (including but not limited to maitotoxin (MTX)) can speed up the transglutaminase clotting reaction. Therefore, according to embodiments of the present invention, calcium and/or calcium-mobilizing drugs are included, although alternatively no calcium and/or calcium-mobilizing drug is used. These modifications for using calcium are useful with calcium-dependant transglutaminases but not with calcium-independent transglutaminases.

According to still other embodiments, the hemostatic material of the present invention may further comprise a material for inducing an exothermic reaction, preferably upon combining the cross-linking material, such as transglutaminase for example, and gelatin. The induction of an exothermic reaction may optionally and preferably support cross-linking even under conditions of an ambient environment, wherein "ambient" may optionally be defined as any environment having a temperature of less than about 30° C. Such an exothermic agent may optionally comprise one or more of calcium, chlorine containing molecules (such as calcium chloride or magnesium chloride), or metallic oxides/zeolites for example, or a combination thereof.

Composition Preparation

Compositions as described herein may optionally be prepared according to one or more different methods of various embodiments of the present invention. In one embodiment of the invention, gelatin in the gelatin-mTG mixture is subjected to very specific drying methods that involve the use of heat prior to its mixture with the mTG. These drying methods increase the solubility of gelatin by lowering its melting point, preferably below operating room temperatures. The drying methods can increase the solubility of gelatin without any additives and without altering the environmental conditions under which gelatin or gelatin-mTG solutions are formed. Nonetheless, the addition of certain additives, such as plasticizers or stabilizers, or the manipulation of certain environmental factors, such as temperature, ion concentration, and osmotic pressure, of the gelatin or gelatin-mTG solutions may be used to further enhance the properties of a gelatin-mTG mixture that already incorporates gelatin dried using a technique that reduces its melting point.

In a preferred embodiment of heat-dependant gelatin drying to prepare a gelatin that can form a solution with mTG at reduced temperatures, a pure gelatin solution having a water content of at least 35% is sprayed at a temperature in excess of the gelation and solidification temperature on an excess of finely divided solid gelatin particles which contain less than 8% of water. The particles are then dried in a fluid bed to a water content of from 8 to 13%. This process, as well as variations of this process that are also encompassed within the scope of the present invention, are described in detail in U.S. Pat. No. 4,889,920, hereby incorporated by reference as if fully set forth herein.

In another preferred embodiment of heat-dependant gelatin drying to prepare a gelatin that can form a solution with mTG at reduced temperatures, a gelatin, having a water content of more than 8% by weight based on the total weight of the gelatin and water, is subjected to microwave heating to remove at least 35% of said water content to obtain a treated gelatin having a water content of not more than 16% of weight based on the total weight of the gelatin and water. This process, as well as variations of this process that should also be considered part of the current invention, are described in detail in U.S. Pat. No. 4,224,348, hereby incorporated by reference as if fully set forth herein.

In another embodiment of heat-dependant gelatin drying to prepare a gelatin that can form a solution with mTG at reduced temperatures, gelatin is dried at 100° C. under reduced pressure as described in U.S. Pat. No. 2,803,548, hereby incorporated by reference as if fully set forth herein. This process alters the gelatin strands themselves, rendering them incapable of being thermoreversibly gelled. Though mTG cross-linking of gelatin is not dependant on gelatin's ability to form a thermoreversible gel, this drying process results in a weakening of the gelatin strands, and thus of any gel created using such gelatin in gelatin-mTG cross-linking.

In another embodiment of the invention, gelatin in the gelatin-mTG mixture is subjected to very specific drying methods that involve the use of lyophilization prior to its mixture with the mTG. These drying methods increase the solubility of gelatin by lowering its melting point, preferably below operating room temperatures. The drying methods can increase gelatin's solubility without any additives and without altering the environmental conditions under which gelatin or gelatin-mTG solutions are formed. Nonetheless, the addition of certain additives, such as plasticizers or stabilizers, or the manipulation of certain environmental factors, such as temperature, ion concentration, and osmotic pressure, of the gelatin or gelatin-mTG solutions may be used to further enhance the properties of a gelatin-mTG mixture that already incorporates gelatin dried using a lyophilization technique that reduces its melting point.

In a preferred embodiment of lyophilizing gelatin drying to prepare a gelatin that can form a solution with mTG at reduced temperatures, a gelatin dissolved in water at a concentration of 0.1-2% by weight is freeze-dried under reduced pressure. This process, as well as variations of this process that should also be considered part of the current invention, are described in detail in U.S. Pat. No. 2,166,074, hereby incorporated by reference as if fully set forth herein.

In another embodiment of the invention, the gelatin-mTG mixture is subjected to lyophilization once the gelatin and mTG have already been mixed in solution. This lowers the melting point of gelatin while resulting in an evenly mixed, lyophilized gelatin-mTG mixture where the gelatin in dry form is in contact with the mTG in dry form. In this embodiment, the gelatin and mTG are simultaneously reconstituted from lyophilized state and immediately form a solution at the site of reconstitution. This technique can preferentially be used with gelatin or a gelatin mixture that already has a lower melting point than standard gelatin since the activity of mTG decreases exponentially at lower temperatures (below about 37° C.).

Thus, a solution consisting of reduced-melting point gelatin and mTG can be formed at a low temperature without rapid cross-linking and gelation occurring. This solution can then be lyophilized, resulting in a dried mixture of homogenously distributed gelatin and mTG. Such a mixture can be rapidly reconstituted to form a gel when put in contact with a warmer solvent. Such a technique could preferentially be used in a wound dressing, where bodily fluids at their natural temperature of 37° C. can reconstitute the gelatin and mTG.

Preferably, according to some embodiments of the present invention, there is provided a gelatin-mTG particle mixture for hemostatic or tissue sealant purposes wherein the gelatin and mTG are spray dried together to create a well dispersed powder containing gelatin and mTG in concentration appropriate for the hemostatic or tissue sealant applications.

In another embodiment of the current invention, the gelatin used as part of the gelatin-mTG mixture has been hydrolyzed, partially hydrolyzed, or some percentage of a gelatin mixture has been hydrolyzed or partially hydrolyzed in order to increase its solubility. An example of such a technique has successfully been demonstrated in a process involving the coating of standard gelatin granules with a film of hydrolyzed gelatin (U.S. Pat. No. 4,729,897, hereby incorporated by reference as if fully set forth herein). This embodiment can include the use of gelatin that has been hydrolyzed or partially hydrolyzed in the presence of a plasticizer, which can include a polyhydric alcohol, a carbohydrate, or other plasticizer as described above.

In another embodiment of the current invention, a solution containing pre-mixed mTG and gelatin, or other protein hydrolysates, is freeze dried to increase the stability of the compound. This technique, as used in preparing a composition used for food processing, is described in U.S. Pat. No. 6,030,821, hereby incorporated by reference as if fully set forth herein.

In another embodiment of the current invention, the gelatin used as part of the gelatin-mTG mixture is spray dried after being mixed with acid to form a dilutely acidic gelatin solution wherein the acid is kept at 5-20% of the level of gelatin, allowing fine droplets to form for enhanced drying. This process is described in Canadian Patent 896, 965, hereby incorporated by reference as if fully set forth herein.

In another embodiment of the current invention, one or more of the above-described techniques for enhancing a product containing gelatin and mTG are used in unison or in series. This can preferentially include using two or more plasticizers together in a gelatin or gelatin-mTG solution, using one or more plasticizers in a gelatin or gelatin-mTG solution prior to drying it using one of the described drying methods. It can also include drying the gelatin or gelatin-mTG using one drying technique, dissolving the dried gelatin or gelatin-mTG in solution, and then re-drying the gelatin or gelatin-mTG.

These methods could also optionally be used for composition which undergoes thermoreversible gelation, preferably including for compositions comprising various combinations of non gelatin proteins and also optionally other cross-linkers (other than transglutaminase) for example.

Bandages

An exemplary embodiment of the present invention is directed to a hemostatic dressing, e.g., for treating wounded tissue in a patient, which comprises gelatin and transglutaminase, preferably separated until their interaction is required or desired for the activity of the bandage. The bandage may optionally feature a non-absorbent backing, such as a plastic backing. The bandage may also optionally feature a resorbable material layer.

Another embodiment of the present invention is directed to a hemostatic dressing for treating wounded tissue in a patient which optionally and preferably comprises: (i) a gelatin layer; (ii) a transglutaminase layer adjacent to said gelatin layer; wherein the transglutaminase layer is coextensive or noncoextensive with the gelatin layer.

Another embodiment of the present invention is directed to a hemostatic dressing for treating wounded tissue in a patient which optionally and preferably comprises: (i) a resorbable or non-resorbable material layer; (ii) a gelatin layer adjacent to said material layer; (iii) a transglutaminase layer adjacent to said gelatin layer; wherein the transglutaminase layer is coextensive or noncoextensive with the gelatin layer.

Another embodiment of the present invention is directed to a hemostatic dressing for treating wounded tissue in a patient which comprises: (i) a first gelatin layer; (ii) a resorbable material layer adjacent to the first gelatin layer; (iii) a transglutaminase layer adjacent to the resorbable material layer; and (iv) a second gelatin layer adjacent to the transglutaminase layer, wherein the transglutaminase layer is noncoextensive with the first and/or second gelatin layers.

According to some embodiments, the present invention provides a hemostatic dressing (e.g., a bandage) that includes a layer of transglutaminase sandwiched between a first and a second layer of gelatin, wherein the transglutaminase layer may be coextensive or noncoextensive with the first and/or second gelatin layer. Such a hemostatic dressing is useful for treating wounds. The noncoextensive model offers the advantage of inhibiting delamination of the layers, as compared with dressings in which the transglutaminase layer is coextensive with the entire first and second gelatin layers. However, hemostatic performance of the coextensive model may be superior to that of the noncoextensive model.

According to other embodiments of the present invention, there is provided a dressing of the invention which optionally and preferably comprises: (i) a resorbable or non-resorbable matrix; (ii) gelatin; (iii) a transglutaminase; wherein the gelatin and transglutaminase are incorporated within said matrix.

In another embodiment, the hemostatic device comprises: (i) a porous resorbable or non-resorbable matrix; (ii) gelatin; (iii) a transglutaminase; wherein the gelatin and transglutaminase are adhered to said matrix.

In various embodiments, the transglutaminase layer can be configured in any of a variety of shapes and patterns. For example, and without limitation, the transglutaminase layer can be configured as an array of spots comprising transglutaminase, or as a single spot comprising transglutaminase. Alternatively, the transglutaminase layer can be configured as a plurality of lines comprising transglutaminase.

Each layer of the hemostatic dressings can also optionally contain one or more suitable fillers, binding agents and/or solubilizing agents. In addition, each of the hemostatic dressings can also optionally further comprise a release layer which contains a release agent and/or a backing material.

According to preferred embodiments, each layer of the hemostatic dressings may optionally contain one or more suitable fillers, such as sucrose. Each layer of the hemostatic dressings can also optionally contain one or more suitable binding agents, such as sucrose. Each of the hemostatic dressings can also optionally further comprise a release layer which contains a release agent. An exemplary release agent is sucrose. Each layer of the hemostatic dressings can also optionally contain one or more suitable solubilizing agents, such as sucrose.

Without wishing to be limited by a single hypothesis, the properties of sucrose as part of the present invention may optionally be at least partially determined by an amount added. In relatively high concentrations (20-30% sucrose solution) it can be sprayed onto surface (such as a bandage) to prepare that surface for application of another solution (such as gelatin or mTG solution) to be adhered. At lower concentrations (around 2% for example), the sucrose can be added to the gelatin or mTG solution to help such a solution adhere to a surface (such as the bandage).

Each layer of the hemostatic dressings can also optionally contain one or more suitable foaming agents, such as a mixture of citric acid and sodium bicarbonate.

Each of the hemostatic dressings can also further comprise a backing material on the side of the dressing opposite the wound-facing side when the dressing is in use. The backing material can be affixed with a physiologically-acceptable adhesive or can be self-adhering (e.g. by having a surface static charge). The backing material can be a resorbable material or a non-resorbable material, such as a silicone patch or plastic patch, and/or a device such as a vascular catheter and/or other type of medical device which may optionally be inserted to the body.

The transglutaminase layer can be applied to the first gelatin layer such that it is noncoextensive with the first gelatin layer and/or will be noncoextensive with the second gelatin layer upon application of the second gelatin layer. For example, the transglutaminase layer can occupy about 5% to about 95% of the surface area of the first gelatin layer and/or about 5% to about 95% of the surface area of the second gelatin layer. The transglutaminase can be applied to the gelatin layer in a single spot or as a series of spots on the gelatin layer such that the total surface area of the transglutaminase spots occupies about 5% to about 95% of the surface area of the first gelatin layer and/or about 5% to about 95% of the surface area of the second gelatin layer.

Such a spot or spots of transglutaminase can have any geometric shape, e.g., filled or unfilled circles, rectangles, triangles, lines, amorphous shapes, or combinations thereof. Such spots can be applied to the first gelatin layer in an ordered or random pattern. A plurality of spots can form any of a variety of shapes and patterns, such as an array, a grid, a series of concentric spots (e.g., concentric circles or squares), an overlapping series of spots (e.g., overlapping circles), spokes emanating from an axis, or any other configuration, provided that the total surface area of the transglutaminase is about 5% to about 95% of the surface area of the first gelatin layer and/or about 5% to about 95% of the surface area of the second gelatin layer. In general, a large number of small spots is preferred over a small number of large spots. For example, a 20.times.20 array of spots generally is preferable over a 10.times.10 array of spots occupying the same total surface area. However, the spots can be of any size provided that the total surface area of the transglutaminase is about 5% to about 95% of the surface area of the first gelatin layer and/or about 5% to about 95% of the surface area of the second gelatin layer. For example, depending upon the overall size of the dressing, the spots can be, without limitation, at least about 0.01, 0.1, 0.5, 1, 2, 3, 4, 5, 6, 7, 8, 9, 10 mm or more in diameter, width, or length. In one embodiment, for example, 4 circular spots having a diameter of 2-3 mm each can occupy a square centimeter of a dressing. A variety of other configurations are within the scope of the invention and can readily be utilized by those skilled in the art.

The dressing can optionally be prepared as any of a variety of sizes and shapes. Typically, the dressings are of a size and shape that can readily be handled by those skilled in the art, typically less than 12" in length along any side, e.g., 1"×1", 1"×2", 4"×4", etc. The moisture level of the dressing typically is less than 8% (e.g., less than 7, 6, 5, 4, 3, 2, or 1%).

Any of a variety of resorbable materials known to those skilled in the art can be optionally employed in the present invention. For example, the resorbable material can be a proteinaceous substance, such as fibrin, keratin, collagen and/or gelatin, or a carbohydrate substances, such as alginates, chitin, cellulose, proteoglycans (e.g. poly-N-acetyl glucosamine), glycolic acid polymers, lactic acid polymers, or glycolic acid/lactic acid co-polymers. For example, the resorbable material can be a carbohydrate substance. Illustrative examples of resorbable materials are sold under the tradenames VICRYL™ and DEXON™.

Generally, the various layers of the hemostatic dressing can be affixed to one another by any means known and available to those skilled in the art. For example, optionally and preferably the gelatin layer(s) and/or the transglutaminase layer(s) is (are) applied as a series of quick-frozen aqueous solution layers and subsequently lyophilized or freeze-dried, e.g., after application of each layer, and upon assembly of the entire dressing. The layers can be applied by any of a variety of techniques, including spraying, pipetting (e.g., with a multi-channel pipettor), sprinkling, using a mask, electrostatic deposition, using a microsyringe array system, or dispensing using a dispensing manifold that contains ports for producing a high density array.

In certain embodiments of the present invention, when the dressings are prepared using a mold, a release agent, such as sucrose, is applied to the mold before the first layer of the dressing is applied. In such embodiments, the hemostatic dressing further comprises a release layer, which contains said release agent.

Alternatively, a physiologically-acceptable adhesive can be applied to the resorbable material and/or the backing material (when present) and the gelatin layer(s) and/or the transglutaminase layer(s) subsequently affixed thereto.

In one embodiment of the dressing, the physiologically-acceptable adhesive has a shear strength and/or structure such that the resorbable material and/or backing material can be separated from the gelatin layer after application of the dressing to wounded tissue. In another embodiment, the physiologically-acceptable adhesive has a shear strength such that the resorbable material and/or backing material cannot be separated from the gelatin layer after application of the dressing to wounded tissue.

The concentration of gelatin per area of the wound depends upon a number of factors, including but not limited to the final construction of the bandage, materials employed and so forth.

According to other embodiments of the present invention, there are provided methods for preparing a hemostatic dressing by optionally and preferably providing a first layer of gelatin, applying a layer of transglutaminase to the first layer of gelatin, and applying a second layer of gelatin to the layer of transglutaminase, wherein the layer of transglutaminase is noncoextensive with the first gelatin layer and/or noncoextensive with the second gelatin layer.

Similarly, other embodiments of the invention include a method for preparing a hemostatic dressing by providing a resorbable or nonresorbable backing layer having attached thereto a first layer of gelatin; applying a layer of transglutaminase to said first layer of gelatin on a side of the gelatin layer that is opposite of the side to which the resorbable or nonresorbable backing layer is attached; and applying a second layer of gelatin to the layer of transglutaminase, wherein the layer of transglutaminase is noncoextensive with the first gelatin layer and/or noncoextensive with the second gelatin layer.

Hemostatic Device

Another exemplary embodiment of the present invention is directed to a hemostatic device, e.g., for hemostasis in a surgical environment of a briskly bleeding patient, which comprises: (i) a porous resorbable or non-resorbable matrix; (ii) gelatin in powder, particle, or other solid form, and (iii) transglutaminase in powder, particle or other solid form; wherein the gelatin and transglutaminase are incorporated within said matrix.

Another embodiment of the present invention is directed to a hemostatic device, e.g., for hemostasis in a surgical environment of a briskly bleeding patient, which comprises: (i) a porous resorbable or non-resorbable matrix; (ii) gelatin; (iii) a transglutaminase; wherein the gelatin and transglutaminase are adhered to said matrix.

Other embodiments of the present invention include application of the hemostatic/sealant mixture through accepted methods of sealant application. Such methods may optionally include application of the mixture as part of a gel, foam, or spray. Application of the hemostatic/sealant mixture using these methods may optionally be accomplished for example by storing the mixture components separately and mixing them immediately prior to application; and/or for example optionally by storing the components together in inactivated form and activating them immediately prior to application. Inactivated forms of the sealant components may optionally be provided as one or more of a frozen solution, a lyophilized powder that requires reconstitution, a spray dried powder that requires reconstitution, and/or any other suitable form of inactivated sealant mixture.

Hemostatic Device Preparation

According to some embodiments of the present invention, a freeze drying and/or lyophilizing technique may optionally be applied to adhere or fix the sealant composition according to the present invention onto the surface of any catheters, trocars or implants, or indeed any other such medical device. This may optionally facilitate hemostasis at the penetration wound and its closure, which may optionally be useful for arterial catheters/devices for example. Hemostasis after arterial procedure is critical for patients who have been treated with anti-coagulation medication and who are more prone to bleeding complications. The hemostatic composition of the present invention is independent of blood clotting and so provides additional assistance to prevent excess bleeding.

Use of Device, Composition or Bandage

During use of the hemostatic dressing, device, or agent, the gelatin and the transglutaminase can be activated at the time the dressing, device, or particle mixture is applied to the wounded tissue by the endogenous fluids (e.g., blood, air, bile, intestinal fluid) of the patient escaping from the hemorrhaging or leaking wound. Alternatively, in situations where fluid loss from the wounded tissue is insufficient to provide adequate hydration of the protein layers, the gelatin and or the transglutaminase can be activated by a application of a physiologically-acceptable liquid (e.g., water, buffer, saline), optionally containing any necessary co-factors and/or enzymes, prior to or upon application of the hemostatic dressing, device, or agent to the wounded tissue.

The principles and operation of the present invention may be better understood with reference to the drawings and the accompanying description.

Referring now to the drawings, FIG. 1 is a schematic block diagram of an exemplary bandage according to the present invention. As shown, a bandage 100 preferably features at least one and preferably a plurality of layers of gelatin 102, shown as two such layers for the purpose of description only and without any intention of being limiting. At least one layer of transglutaminase 104 is preferably also provided; in this example, layer of transglutaminase 104 is shown as being sandwiched between the plurality of layers of gelatin 102 for the purpose of illustration only and without any intention of being limiting. A suitable backing 106 is also shown, which preferably provides mechanical strength to bandage 100. Backing 106 may optionally be implemented as a polyglycolic acid mesh or patch, such as for example provided as Dexon™ or Vicryl™.

Figure 2:
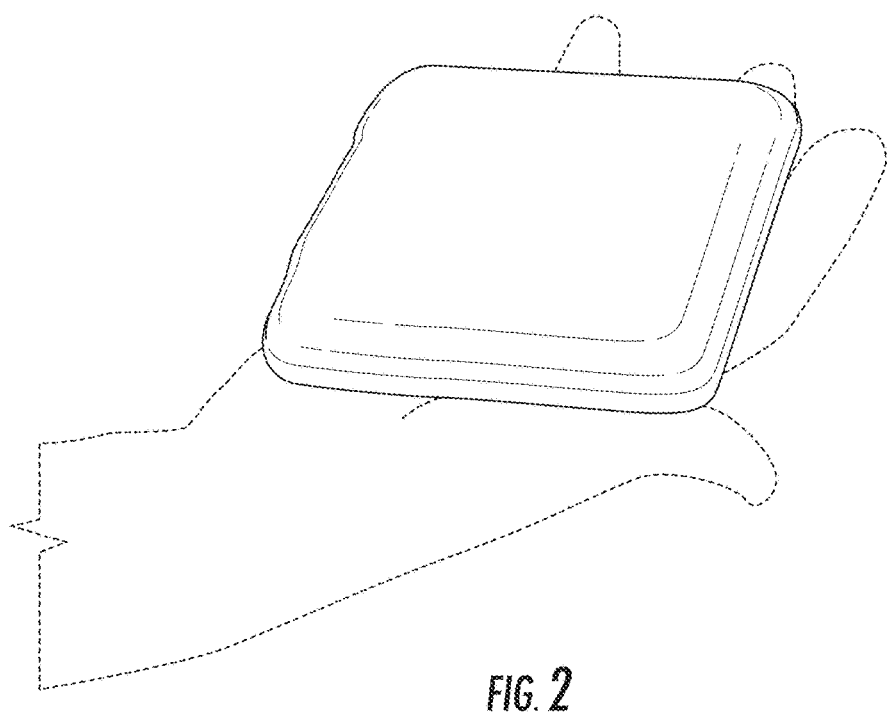
FIG. 2 shows a frontal view of an exemplary bandage according to the present invention, covered with an optional absorbable backing and an optional plastic wrapping.

FIG. 2 shows a frontal view of an exemplary bandage according to the present invention, covered with an optional absorbable backing and an optional plastic wrapping.

Figure 3:
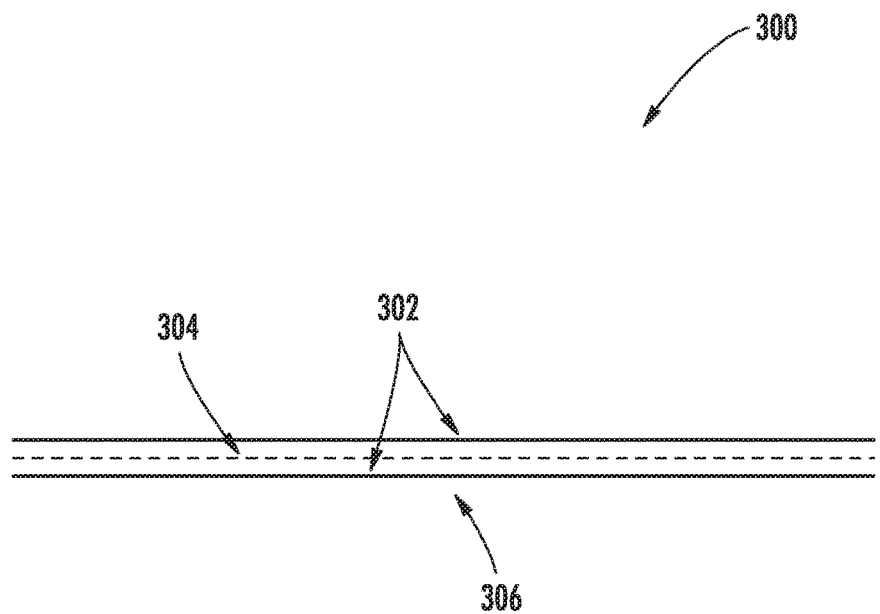
FIG. 3 is a schematic block diagram of an exemplary of a hemostatic device according to the present invention, incorporating a porous matrix.

FIG. 3 is a schematic block diagram of an exemplary of a hemostatic device according to the present invention, incorporating a porous matrix. As shown, a hemostatic device 300 preferably features at least one and preferably a plurality of layers of gelatin 302, shown as two such layers for the purpose of description only and without any intention of being limiting. At least one layer of transglutaminase 304 is preferably also provided; in this example, layer of transglutaminase 304 is shown as being sandwiched between the plurality of layers of gelatin 302 for the purpose of illustration only and without any intention of being limiting. A suitable backing 306 is also shown, which preferably provides mechanical strength to bandage 300. Backing 306 may optionally be implemented as any type of biodegradable material.

Referring now to the below Examples, various compositions according to the present invention were constructed and tested for their ability to reduce bleeding and to induce hemostasis. The tested compositions were found to be very strong and to be able to stop bleeding, even arterial bleeding, in an experimental animal.

Example 1

Preparation of Illustrative Adhesive

This Example relates to the preparation of an illustrative, non-limiting adhesive according to the present invention. For this Example, calcium independent microbial transglutaminase (Lot No. L-04207, Ajinomoto USA, Chicago, Ill.) was used with a specific activity level of 100 U/gm. Also the tested gelatin was Gelatin type A, 300 Bloom from porcine skin (Sigma-Aldrich, St. Louis, Mo.).

The following method was used to prepare the illustrative adhesive: 20% w/w gelatin in PBS (phosphate buffered saline; 20 g gelatin into 80 g of PBS) was prepared. Next a 20% w/v mTG solution was prepared in PBS (1 gm mTG into 5 mL PBS). Then, 5 g of gelatin solution was mixed with 0.5 mL of mTG solution (in other words 10:1 ratio).

Figure 4:
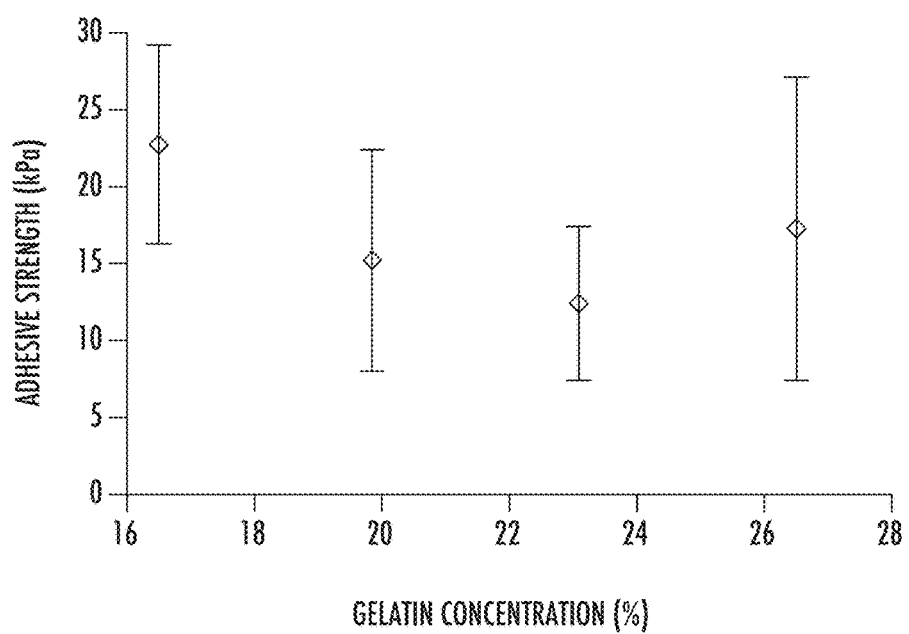
FIG. 4 is a graph showing the effect of different percentages of a tested gelatin on wound strength.

FIG. 4 shows the effect of different percentages of gelatin on the adhesive strength of the adhesive. The adhesive strengths were measured by adhering a porcine skin sample to a second such sample, placing a 47.5 g weight on the joint, and then submerging it immediately in water for 120 minutes. After the submersion period, tension was applied at 5 mm/min to determine the ultimate adhesion strength (Mcdermott et al. Biomacromolecules 2004, 5, 1270-1279).

Figure 5:
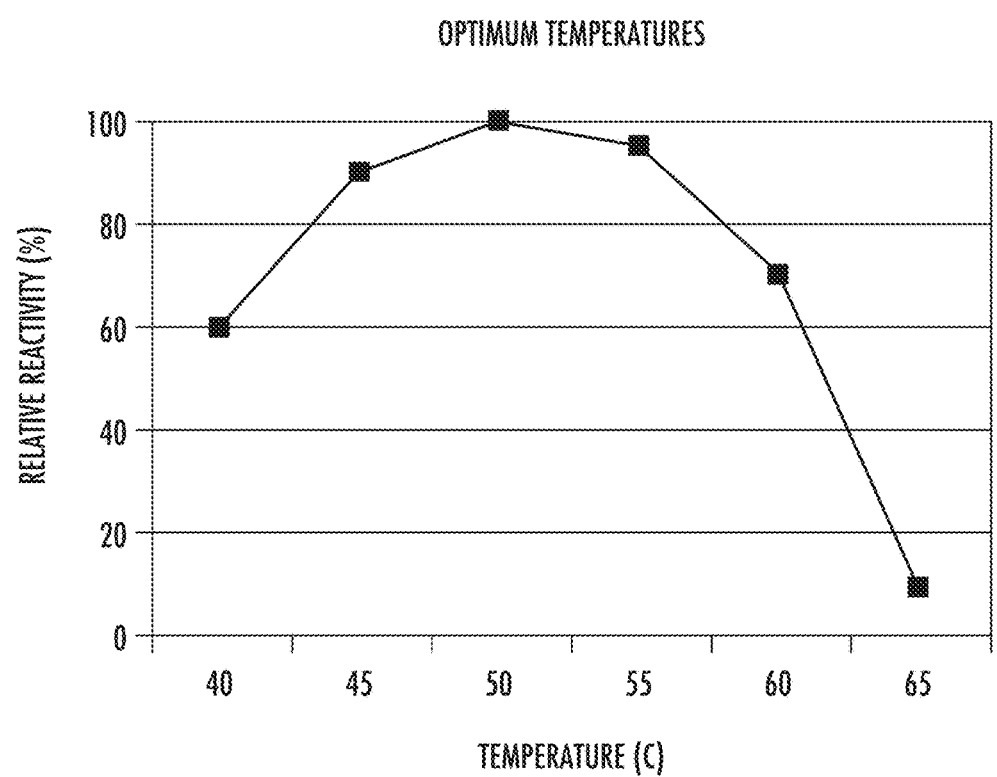
FIG. 5 shows effect of temperature on activity of transglutaminase (Temperature Range tested was 32 to ~150° F.; optimum range was 122-131° F. (50-55° C.))

As demonstrated in FIG. 5, the optimum reactivity level of microbial transglutaminase is in the range of 50-55° C. At the physiological level of 37° C., the reactivity level is only about 60% of the optimum level. As such, raising the temperature of the reaction using an exothermic agent would raise the reactivity level and thus speed up the gelatin cross-linking. Thus, optionally and preferably an exothermic agent is part of the present invention.

Calcium may optionally be used as part of such an agent since calcium chloride releases heat when dissolved but not enough heat to damage tissue. Also, as noted above, it is possible that calcium could help accelerate the reaction in other ways, independent of its exothermic dissolution.

Optionally a non-toxic exothermic substance may be included in the bandage with one or more cross-linking factors. Alternatively or additionally, one or more non-reabsorbable exothermic agents may optionally be added behind the bandage backing, as described previously.

Example 2

In Vitro Burst Pressure Test

This Example demonstrates the ability of a composition according to the present invention to withstand bursting as a proxy for its ability to withstand high-pressure arterial blood flow. A burst pressure system was developed, as describe below, to mimic high pressure blood flow, with warm PBS used in the place of blood to put pressure on a wound in a porcine skin sample. Withstanding 200 mmHg of pressure for 2 minutes was considered the success criteria as physiological blood pressure is nearly always lower than 200 mmHg. These burst test results demonstrated that compositions according to the present invention are suitable for treatment of blood flow, including high pressure arterial flow.

Most samples (8/10) withstood a pressurization of 200 mmHg for 2 minutes. Those that did not pass were likely related to human or system error. The average burst pressure was 320±50 mmHg but this number is conservative since samples that did not burst were assigned a numerical value of 354 mmHg, as this was the maximum pressure measurable by the experimental apparatus. These results demonstrate the capability of the adhesive composition according to some embodiments of the present invention to be used for hemostatic purposes, even under rigorous testing conditions.

Materials

Gelatin (type A from porcine, Bloom value 300) was obtained from Sigma-Aldrich (St. Louis, Mo.). The calcium-independent microbial transglutaminase (mTG) mixture TG-TI was obtained from Ajinomoto and was used without further purification. This enzyme is reported by the manufacturer to have a specific activity of 100 U/gm. Porcine skin tissue was purchased from a local grocery store.

Sample Preparation

The porcine skin was treated with dilute NaOH for 1 h before cutting into a disk shape, with a diameter of about 6-6.5 cm. The fat on the skin was removed with a scalpel. A 2-mm hole was punched at the center of the skin section to simulate a wound. The skin was washed with copious amounts of water and PBS buffer, and stored in a Petri dish with about 1 ml PBS buffer to keep the skin wet until use. For all experiments described herein, Dulbecco's Phosphate Buffered Saline was used with a pH of 7.4 for the PBS buffer.

Gelatin solution (25% w/w) in PBS buffer was freshly prepared each day and stored at 65° C. before use. The mTG (20% w/w) stock solution in PBS buffer was prepared and aliquotted into 2 ml vials, and stored at −18° C. The enzyme solution was thawed at room temperature before use.

The skin surface was touch-dried with a lab tissue wipe before the adhesive was applied. The adhesive was prepared in a 2 ml vial by mixing 1 ml gelatin and 0.5 ml mTG. Two different compositions were prepared. Composition "A" used transglutaminase from Ajinomoto, while composition "B" used transglutaminase from (Yiming Biological Products Co. (Jiangsu, China); the preferred product as described above). 0.6 ml of the resultant mixture (an exemplary tissue adhesive composition according to the present invention) was applied onto the porcine skin over the hole. After applying the adhesive, the skin tissue was incubated at 37° C. for 30 min Burst tests were performed immediately after incubation.

Burst Test

The home-built device was equilibrated in warm buffer (~44° C.) before assembly. After quickly assembling the incubated skin into the device, about 50 ml of 42° C. PBS buffer was poured into the device on top of the skin tissue. A nitrogen stream was manually controlled to increase the pressure. The overall procedure for the burst test was as follows:

Step 1—Increase pressure to 200 mmHg and hold for 2 minutes;

Step 2—Increase pressure to 300 mmHg and hold for 2 minutes;

Step 3—Increase pressure to >354 mmHg (maximum pressure measurable).

As controls, pure gelatin solution was applied onto the skin and allowed to gel (i.e., set) at room temperature for 30 min by forming a physical gel. Gelatin-Warm refers to the use of 42° C. buffer solution that can melt the physical gelatin gel.

Results

Figure 6:
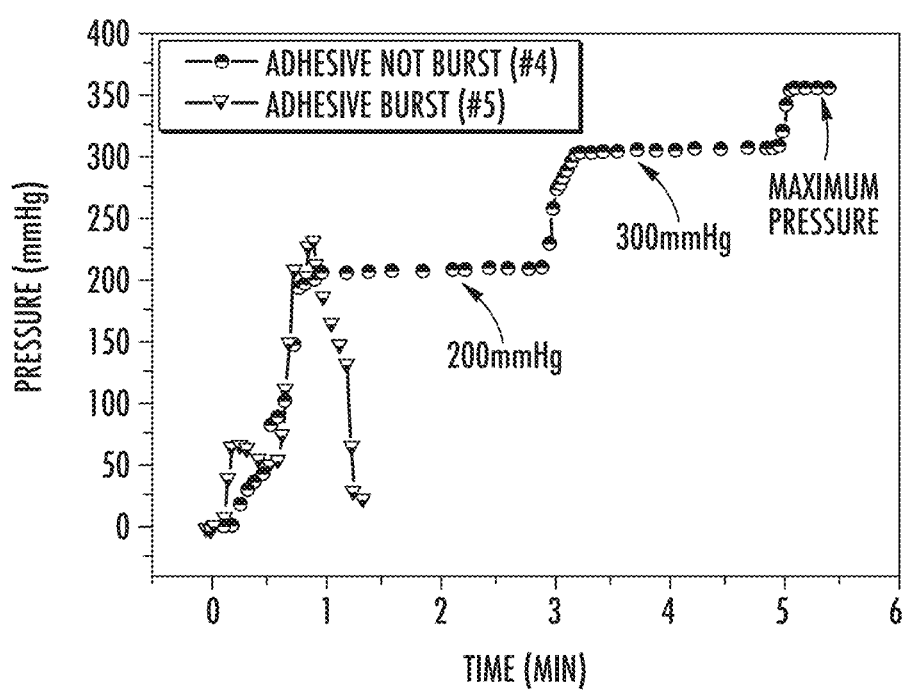
FIG. 6 shows representative burst pressure measurements of tissue adhesives based on composition A.

FIG. 6 shows representative burst pressure measurements of tissue adhesives based on composition A. Data are shown for samples #4 and #5 in FIG. 6. A summary of the burst test results for composition A is given in Table 2, while the full list of samples is shown in Table 3.

TABLE 2

Summary of burst test results for composition A

| Total number of samples tested | 10 |
| No burst | 5 |
| Burst after Step #2 | 1 |
| Burst after Step #1 | 2 |
| Burst during Step #1 | 2 |
| Average burst pressure* | 320 ± 50 mmHg |

*A numerical value of 354 mmHg (maximum pressure measurable) was adopted for "No failure" samples.

TABLE 3

Burst test results of samples of composition A

| Sample # | 200 mmHg | 300 mmHg | Burst pressure (mmHg) | Burst type | Notes |
| --- | --- | --- | --- | --- | --- |
| 1 | 2 min | — | 325 | cohesive | |
| 2 | 2 min | 2 min | >354 | | |
| 3 | 2 min | 2 min | >354 | | |
| 4 | 2 min | 2 min | >354 | | |
| 5[a] | 30 sec | — | 232 | cohesive | Device leak |
| 6 | 2 min | 2 min | >354 | | |
| 7 | 2 min | 2 min | 348 | cohesive | |
| 8 | 2 min | — | 250 | cohesive | 44° C. PBS |
| 9 | 2 min | 2 min | >354 | | |
| 10 | 10 sec | — | 245 | cohesive | 44° C. PBS |
| Controls: Gelatin-Warm | | | | | |
| 13 | — | — | 181 | melted | 42° C. PBS |
| 14 | — | — | 45 | melted | 37° C. PBS |
| 15 | — | — | 93 | melted | |
| 16 | — | — | 105 | melted | |
| 17 | — | — | 84 | melted | |
| 18 | — | — | 45 | melted | |
| 19 | — | — | 15 | melted | |
| 20 | — | — | 140 | melted | |

[a]At ~200 mmHg device started to leak. Tightening the device increased the pressure but may have also distorted the skin, resulting in adhesive failure at 232 mmHg.

Figure 7:
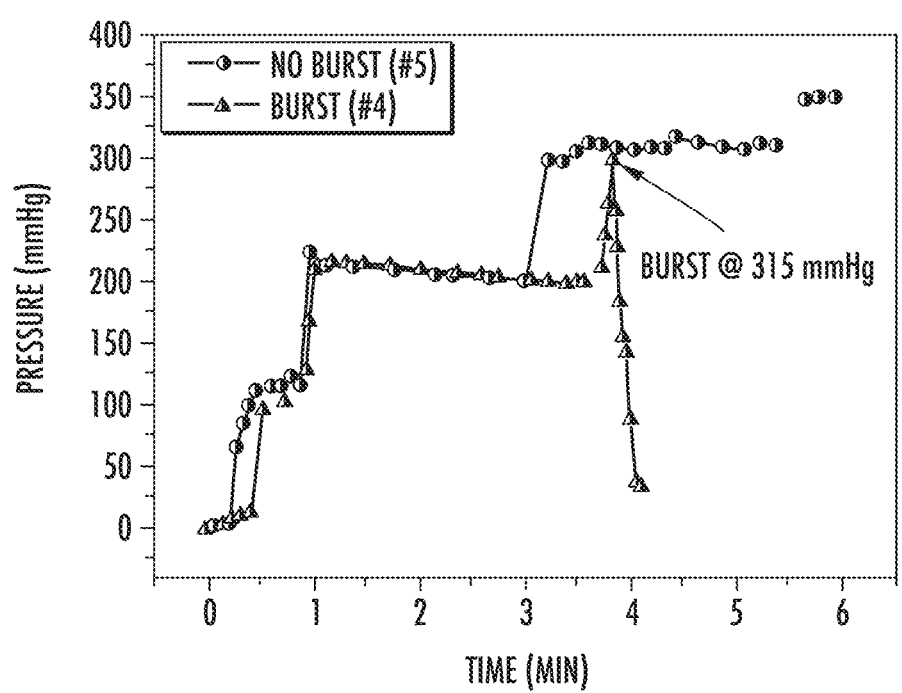
FIG. 7 shows representative burst pressure measurements of tissue adhesives based on composition B.

FIG. 7 shows representative burst pressure measurements of tissue adhesives of composition B. Data are shown for samples #4 and #5 in FIG. 7. Results for the full list of samples are shown in Table 4.

TABLE 4

Burst test results of samples of composition B.

| Sample # | 200 mmHg | 300 mmHg | Burst pressure (mmHg) | Burst type | Notes |
| --- | --- | --- | --- | --- | --- |
| 1* | | 2 min | max | | |
| 2 | 2 min | 2 min | max | | |
| 3* | | | max, 2 min | | |
| 4 | 2 min | — | 315 | cohesive | 44° C. PBS |
| 5 | 2 min | 2 min | max | | |

*The pressures of these samples were inadvertently set above 200 mmHg since the pressure was controlled manually and there is no pressure release valve.

Example 3

Hemostasis in a Rat Model

This Example provides an initial in vivo demonstration of a gelatin-mTG composition according to the present invention for achieving hemostasis in a live animal. The rat was an adult female Syrian Rat.

Materials

A gelatin solution was used which featured 25% w/w gelatin (porcine, type A, 300 bloom from Sigma-Aldrich (St. Louis, Mo.)) in PBS. The solution was mixed by mixing heated (50° C.) PBS into gelatin powder as it was manually stirred using a spatula. Prior to application, gelatin solution was stored in capped 5 mL syringes submerged in a 50° C. water bath to maintain its liquid phase.

The transglutaminase (mTG) solution featured 20% w/w microbial transglutaminase (Activa WM, Ajinomoto™) in PBS. The mTG solution was maintained at room temperature.

Prior to application, 1 mL of gelatin solution was added to 0.5 mL of mTG solution in a 2 mL eppendorf tube. The tube was inverted 2-3 times to mix the solutions and then solution was applied to the wound site using a 1 mL pipette tip. This was the experimental solution.

For the control solution, the protocol was repeated but without the addition of mTG solution, such that gelatin alone was administered.

For both experimental and control applications, pipette tips were cut approximately ½ cm from the end in order to expand the opening and enable the passage of the viscous gelatin-mTG solution.

Liver Wound

For both the experimental and control applications, the left lobe of the liver was cut using a scalpel in the rostral-to-caudal direction, creating a 1 cm long, ½ cm deep sagittal cut. After approximately 10 seconds of bleeding, cotton gauze was used to remove the accumulated blood immediately prior to application of either the gelatin (control) or gelatin-mTG (experimental) solutions.

First, the experimental solution was applied to a cut on the left side of the lobe. A gel formed approximately two minutes after application and bleeding was completely stopped in less than about 2.5 minutes after application. After 5 minutes, the tissue was vigorously agitated and tension was applied across the wound site using forceps, yet the gel remained intact and the wound closed. FIG. 8 is a photograph showing the formation of the gel and also induction of hemostasis (FIG. 8A shows the entire area while FIG. 8B shows a portion of the area, magnified for further details).

Figure 9A:
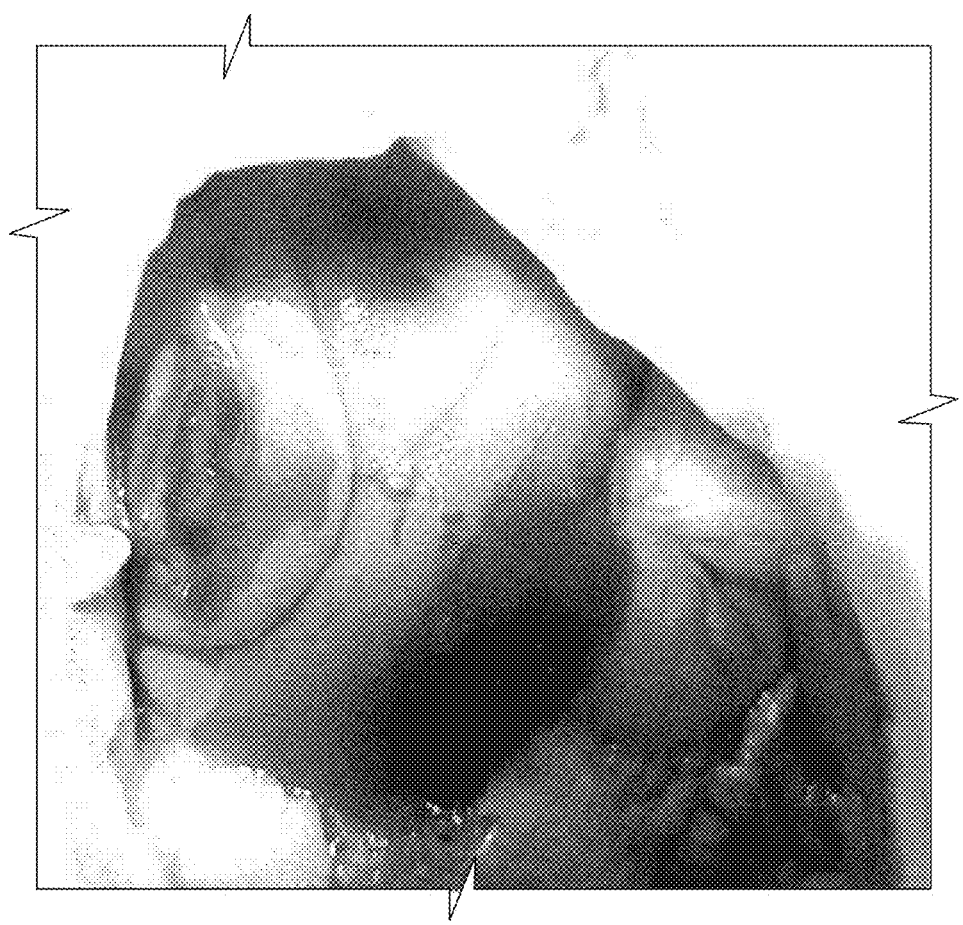

Afterward, the control solution was applied to a cut on the right side of the lobe. No gel formed and the solution was mostly washed out of the wound site by the blood flow. Even after 6-7 minutes, no clot was formed and the liver continued bleeding (FIG. 9A).

Figure 9B:
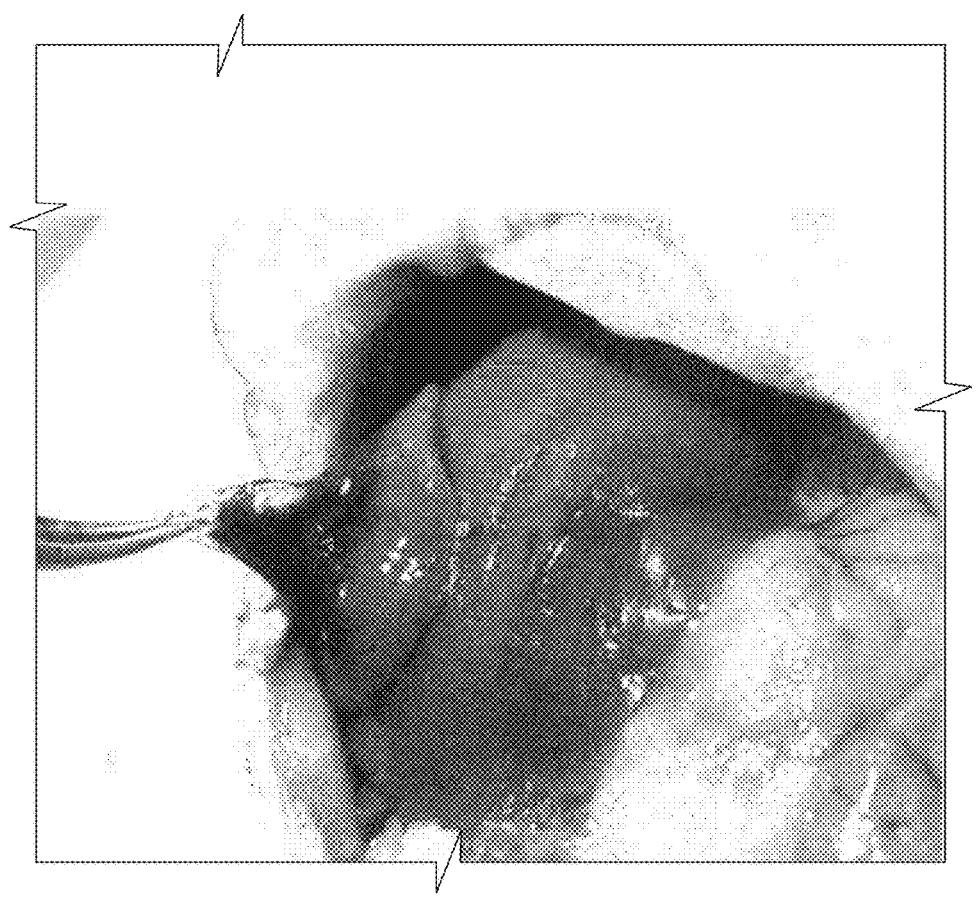
FIG. 9B shows gelation of the experimental solution and hemostasis.
Figure 10B:
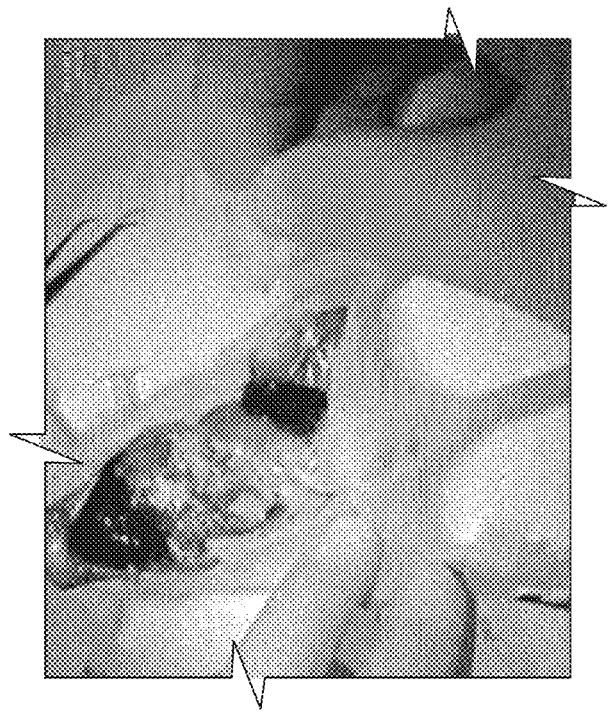
FIGS. 10, 10C and 10D (note that the Figure labeled "FIG. 10" includes "A" and "B" labels in the photographs themselves) show photographs of the artery as it was being cut (see photograph labeled "A"); the cut artery, bleeding profusely (see photograph labeled "B"); application of the composition of the present invention to the cut artery (10C); and hemostasis, with formation of a biomimetic clot (10D)
Figure 10A:
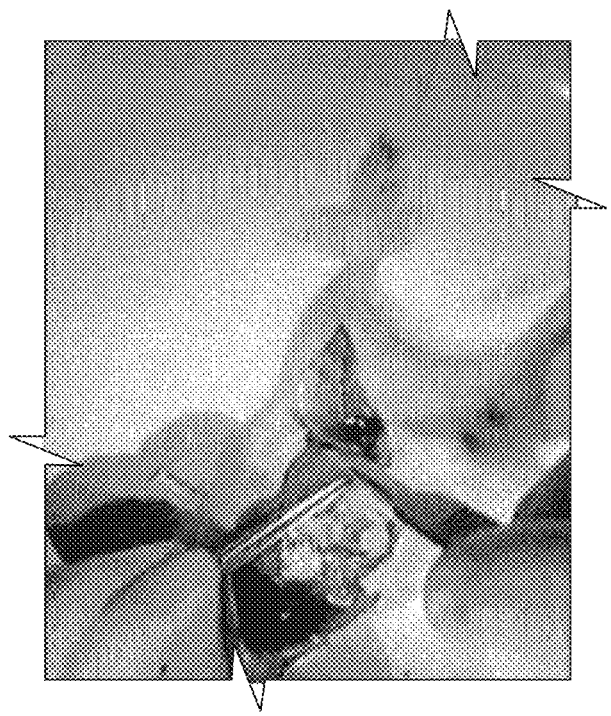
Figure 10D:
Figure 10C:

The control solution was removed and the experimental solution was then applied to the wound site without removing the accumulated blood. Though the accumulated blood observably hindered adhesion of the experimental solution to the liver, a gel still formed that greatly slowed blood flow after about one minute and completely stopped it after 4.5 minutes (FIG. 9B). This demonstrated that the composition of the present invention is able to slow blood flow and induce hemostasis even in the presence of accumulated blood.

Femoral Artery Cut

The left femoral artery of the rat was severed using a scalpel. After approximately 10 seconds of heavy bleeding, cotton gauze was used to remove the accumulated blood immediately prior to application of the gelatin-mTG (experimental) solution. As the solution was applied, blood mixed with the experimental gel as it was undergoing gelation. Under these rigorous conditions, the gel still completely stopped the bleeding in less than three minutes. After 5 minutes, the gel was manually tested using forceps. Gel was noticeably less stiff and less adherent when it was mixed heavily with blood but still formed a strong clot over the severed artery site. FIGS. 10A-D show photographs of the artery as it was being cut (10A); the cut artery, bleeding profusely (10B); application of the composition of the present invention to the cut artery (10C); and hemostasis, with formation of a biomimetic clot (10D).

The right femoral artery of the rat was then severed using a scalpel. After approximately 10 seconds of bleeding, cotton gauze was used to remove the accumulated blood immediately prior to application of the gelatin-mTG (experimental) solution. Heavy bleeding was observed but was almost immediately halted by the gel and bleeding was completely stopped in less than one minute. The gel held very strongly and the blood that was trapped by gel was readily observable. After 5 minutes, the gel was manually tested using forceps. It was adhered very strongly to the tissue in the area of the artery, despite the presence of trapped blood in the formed gel.

Thus, clearly compositions according to the present invention are able to slow down the rate of bleeding and to induce hemostasis in an in vivo model, even in the presence of accumulated blood and/or heavy bleeding (as for example from an artery and/or a vascularized organ including but not limited to liver, stomach, kidneys, heart, lung and/or skin for example).

Example 4

Hemostasis in a Porcine Model

This example provides an initial in vivo demonstration of a gelatin-mTG composition according to the present invention for achieving hemostasis in a large animal model. The potential for hemostasis utility in a large animal model was clearly demonstrated.

Materials

The gelatin solution featured 25% w/w gelatin (porcine, type A, 300 bloom from Sigma-Aldrich (St. Louis, Mo.)) in PBS (pH 7.4) and was prepared as described herein. PBS was stirred continuously at 60° C. using a hot plate magnetic stirrer while gelatin powder was gradually added. Manual stirring using a glass stick was performed occasionally to increase the dissolution rate of the powder and to achieve a homogenous solution. Throughout the entire experiment, the gelatin solution was stored in a thermal bath adjusted to ~50° C. to maintain its liquid phase and prevent the formation of a thermoreversible gel.

The mTG solution featured 20% w/w microbial transglutaminase (Activa WM, Ajinomoto™) dissolved in PBS (pH 7.4). It was prepared as follows. Room temperature (RT) PBS solution was stirred using a magnetic stirrer and mTG powder was gradually added. Throughout the entire experiment the mTG solution was kept in a thermal bath adjusted to ~30° C., except when in actual use.

An adult, female pig weighing 45 kg was put under general anesthesia prior to the start of the experiment. Throughout the experiment the pig was ventilated and its vital signs were monitored.

Prior to application to the wound site as described below, the gelatin-mTG solution according to the present invention was prepared and an applicator was used to place the sealant onto the wound site. Several different applicators were examined as the bandage's supportive material. Unless otherwise stated, before its immediate application onto wound site, 6 mL of novel surgical sealant solution were spread over the applicator and left to cool for 1 min at RT. This sealant-containing pad is considered the "bandage prototype". For the "control bandage", a similar protocol was followed, but with the control solution being spread over the applicator.

Novel Surgical Sealant Solution—A 2:1 gelatin to mTG mixture was prepared. Unless otherwise stated, the mixture was prepared by adding 2 mL mTG solution to 4 mL gelatin solution in a 15 mL tube and the tube was inverted 5 times to mix the solutions.

Control Solution—For the control solution the procedure described for Novel Surgical Sealant preparation was repeated, except that PBS alone was used instead of the mTG solution. Accordingly, gelatin was diluted in a 2:1 ratio with PBS solution (pH 7.4), submerged in a ~30° C. thermal bath. Unless otherwise stated, the mixture was prepared by adding 2 mL PBS solution to 4 mL gelatin solution in a 15 mL tube and the tube was inverted 5 times to mix the solutions.

Applicators were used as follows:
1. A 4 cm×4 cm cotton gauze pad.
2. A 4 cm×4 cm disposable plastic backed absorbent pad. The solution was spread on the plastic, non-absorbing side of the pad.
3. A silicon mold.
4. A 4 cm×4 cm disposable plastic backed absorbent pad placed inside a silicon mold. The solution was spread on the plastic, non-absorbing side of the pad.
5. A transparent flexible plastic mold with high margins.
6. Direct application of the sealant on the wound site using a syringe or spilling from a 15 mL tube.

Application of the novel surgical sealant in this study was accomplished by the surgeon manually placing the sealant over the wound site using different applicators. If needed, cotton gauze was used to remove the accumulated blood immediately prior to application. Hemostatic pressure was applied on the inverse side of the bandage for 3 minutes. After 3 minutes, the surgeon relieved pressure and wound site was observed for hemostasis. If full hemostasis did not occur, the wound site was closed by accepted surgical hemostatic techniques. Application of the control solution followed the same technique, with accepted hemostatic techniques being immediately applied if hemostasis was not observed after the control bandage was removed.

Gluteal Muscle Wound

The animal was placed in a prone position and the skin above the gluteal muscles was removed. Overall, 7 experiments were conducted in which hemostasis and tissue adhesion were examined. Unless otherwise stated, in each trial a 3 cm×3 cm square of muscle was cut 2 cm deep into the muscle, using a #15 scalpel. Excess blood was removed from the wound area as needed and the novel surgical sealant solution or control solution were applied as previously described.

Tables 5 and 6 summarize and describe the experimental procedure and results of each of the experiments. Table 5 relates to hemostasis while Table 6 relates to tissue adhesive properties.

Turning first to hemostasis, the control solution was applied to a wound site using a cotton gauze pad (Table 5, Control #1). The control solution was applied on the cotton gauze and left to cool for 1 min 20 sec prior to its immediate application. The wound site bled only lightly and complete hemostasis was observed 2 min after application of the control bandage. Though no biomimetic clot was observed at the wound site, the hemostatic pressure applied to the wound site was sufficient to encourage hemostasis.

The experiment was repeated in a different wound site, with the difference being that the applicator used was a disposable plastic backed absorbent pad and the control solution was left to sit for 30 sec prior to its application (Table 5, Control #2). The wound site showed very little bleeding and 2 min after applying the control bandage, complete hemostasis was observed. As in the previous case, this was probably due to the hemostatic pressure applied over the site while applying the bandage. No biomimetic clot was observed at the wound site.

Due to the small amount of bleeding observed during the first two control experiment, the experiment was repeated, with the exception being that a deeper, 4 cm deep cut, was made (Table 5, Control #3). Consequently, heavy bleeding was observed. The control solution was applied over an absorbent pad and left to sit for 50 s. The surgeon removed excess blood from the wound area and applied the control bandage. After 3 min, bleeding decreased but full hemostasis was not observed.

The control solution was removed from the wound site created at the former experiment using a cotton gauze pad. Bleeding was still observed. The novel surgical sealant was applied to the wound area to achieve hemostasis (Table 5, Sealant #1). The sealant solution was placed over an absorbent pad, left to sit for 1 min and applied over the wound site. After 3 min, complete hemostasis was observed. The sealant formed a biomimetic clot over the wound site. The gel was agitated using forceps and strong adherence to the tissue was observed. The gel was removed after applying some force and appeared as a film. Thus, these results demonstrated the hemostatic properties of the composition according to the present invention.

TABLE 5

| | | | | Gluteal Muscle | | |
|---|---|---|---|---|---|---|
| Experiment | RT (° C.) | Heart Rate | Application Technique | Description | Time to Hemostasis (min) | Results |
| Control #1 | 21 | 99 | Cotton gauze pad | The wound site showed little bleeding following the incision. Prior to applying, control solution was placed over the applicator and left to cool for 1 min 20 sec. | 2 | Note that following the incision, little bleeding from the wound area was observed. Hemostasis was achieved, likely by just applying pressure over the wound site. |

TABLE 5-continued

Gluteal Muscle

| Experiment | RT (° C.) | Heart Rate | Application Technique | Description | Time to Hemostasis (min) | Results |
|---|---|---|---|---|---|---|
| Control # 2 | 21 | 98 | disposable plastic backed absorbent pad | The wound site showed little bleeding following the incision. Control solution was placed over the applicator and left to cool for 30 sec prior to applying onto the wound site. | 2 | Note that following the incision, little bleeding from the wound area was observed. Hemostasis was achieved, likely by just applying pressure over the wound site. |
| Control # 3 | 22 | 98 | disposable plastic backed absorbent pad | 4 cm deep cut was made. Massive bleeding was observed. Control bandage was left to cool for 50 sec. Prior to its application over the wound site, excess blood was removed. | — | The surgeon applied hemostatic pressure due to the massive bleeding. After 3 min, bleeding decreased but did not stop. |
| Sealant # 1 | 22 | 99 | disposable plastic backed absorbent pad | Control solution was removed from the wound site performed for control # 3. Excess blood was removed. The sealant was placed over the bleeding wound site. | 3 | A strong biomimetic clot was formed over the wound site. Complete hemostasis and strong adhesion of the sealant were observed. |

After demonstrating the hemostasis capacity of the sealant in a gluteal muscle model, tissue adhesion was examined (Table 6). Surgical incisions were made to lift a segment of tissue from the muscle bed, opening a wound site.

At the first adhesion experiment (Table 6, Sealant #2), the sealant was directly applied over the wound site and the surgeon applied strong immediate pressure on the upper part of the tissue for 3 min, displacing all of the sealant from the wound site and resulting in no adhesion.

The experiment was repeated with the exception that following the application of the sealant, the surgeon applied only moderate pressure (Table 6, Sealant #3). After 3 min it appeared the tissues adhered. When the upper part of the tissue was agitated, a moderate amount of resistance was experienced to its complete removal.

The experiment was repeated with special care taken to not displace the sealant from the wound site upon application of pressure (Table 6, Sealant #4). On a different wound site, the sealant was applied on both parts of the tissue and left for 10 sec. Then, the upper side of the tissue was replaced and moderate pressure was applied. After 3 min, strong tissue adhesion was observed. A significant amount of force was needed to then separate the adhered tissues.

TABLE 6

| Experiment | RT (° C.) | Heart Rate | Application Technique | Description | Tissue Adhesion | Results |
|---|---|---|---|---|---|---|
| Sealant # 2 | 23 | 99 | Direct application from a tube | Excess blood was removed using a cotton gauze pad. The sealant was placed over the wound site and immediate displacing pressure was applied by the surgeon. | N/A | No sealant remained in the wound site. |
| Sealant # 3 | 23 | 94 | Direct application from a tube | Excess blood was removed using a cotton gauze pad. The sealant was placed at the wound site and the surgeon applied moderate pressure. | + | Adhesion was observed with slight resistance. |

TABLE 6-continued

Tissue Adhesion

| Experiment | RT (° C.) | Heart Rate | Application Technique | Description | Tissue Adhesion | Results |
|---|---|---|---|---|---|---|
| Sealant #4 | 24 | 95 | Direct application from a tube | The sealant solution was placed over the wound site, on both parts of the tissue and left for ~10 sec. then the upper side of the tissue was replaced and very low pressure was applied. | + | Strong adhesion was observed. Only after applying intensive force the tissue was removed. |

Hemostasis in Liver

The pig was placed supine and its liver was exposed through a midline laparotomy. Serial cuts were performed to remove progressively deeper biopsies of the liver, consequently exposing larger blood vessels. Overall, 5 biopsies were preformed. When needed, cotton gauze was used to remove the accumulated blood immediately prior to application of the composition according to the present invention.

For the first series of biopsies, the control bandage was applied with hemostatic pressure on the inverse side of the bandage for 3 minutes. After 3 minutes, the surgeon relieved pressure and the wound site was observed for hemostasis. When full hemostasis did not occur, a deeper biopsy was performed, followed by application of the novel surgical sealant. Again, the sealant was applied with hemostatic pressure on the inverse side of the bandage for 3 min and then hemostasis was examined. When full hemostasis was observed, a deeper liver biopsy was removed and the experiment was repeated with the sealant. This demonstrated the hemostasis capability of the sealant for higher blood pressures. Table 7 summarizes the experimental procedure and results of each experiment.

A 4 cm deep biopsy was removed from the left lobe of the liver (Table 7, Control #1). The control solution was applied over an absorbent pad placed in a silicon mold and left to sit for 1 min. The control bandage was applied over the wound site with hemostatic pressure. After 3 min, pressure was removed and no hemostasis was observed.

After no hemostasis was achieved by applying the control bandage, a 1 cm deeper biopsy was removed and left to bleed for 30 sec. The experiment was then repeated with the novel sealant (Table 7, Sealant #1). The novel sealant was placed on the pad in a silicon mold and after 1 min applied to the wound site with hemostatic pressure. After 3 min, the pressure was relieved, the prototype bandage was peeled, and hemostasis was examined. The sealant created a visible biomimetic film. Hemostasis was achieved but was not complete since the sealant did not cover the entire wound. It was visible that areas covered with the sealant stopped bleeding. When the biomimetic film was removed after several minutes, bleeding resumed.

Next, a 1 cm deeper biopsy was removed, resulting in heavy bleeding. The experiment was repeated with the exception that a silicon mold was used as the applicator and excess blood was removed prior to application (Table 7, Sealant #2). The surgeon then applied pressure to the wound site for 3 min. When the surgeon removed his hand, a biomimetic clot was visible over the wound site. The pressure of the blood pushing against the biomimetic clot was apparent and after several more minutes, blood breached from the rim of the biomimetic sealant. The breach was through a side part of the wound site that was not covered by the sealant. This indicated that, at this stage, the hemostatic ability of the sealant is reliant on covering the entire wound site.

To avoid breaching, the former experiment was repeated; with the exception that a larger amount of sealant was applied over the wound site (Table 7, Sealant #3). A 0.5 cm deeper biopsy was removed from the liver lobe. 9 mL sealant was applied over the wound site with pressure. Unfortunately, during application, nearly all of the sealant dripped off to the sides of the wound site, leaving no discernable sealant on the wound site after pressure was applied by the surgeon.

The experiment was repeated (Table 7, Sealant #4). Another 1 cm biopsy was removed and massive bleeding was observed. This time, 15 mL of sealant was applied over the wound site using a transparent plastic mold with high margins to keep the sealant in place. The sealant was placed on the applicator and left to cool for 1 min 20 sec. The sealant was applied over the wound site and 4 min later, a thick layer of biomimetic clot was observed and complete hemostasis was achieved. 50 min later the tissue was reexamined and hemostasis was still observed. This indicated the strong hemostatic capacity of the sealant when sufficient sealant is applied to a wound site and maintained in place. The formed biomimetic film was difficult to remove as it was strongly adhered to the tissue surface and removal of the film resulted in a small amount of bleeding.

TABLE 7

Hemostasis in Left Liver Lobe

| Experiment | RT (° C.) | Heart Rate | Application Technique | Description | Time to Hemostasis (min) | Results |
|---|---|---|---|---|---|---|
| Control #1 | 25 | 87 | diposable plastic backed absorbent pad in a silicon mold | 4 cm biopsy was removed. The control solution was placed over the applicator, left for 1 min and applied with hemostatic pressure over the wound site for 3 min. | — | Massive bleeding after application. No hemostasis or biomimetic film was observed. |
| Sealant #1 | 24 | 86 | diposable plastic backed absorbent pad in a silicon mold | Another 1 cm biopsy was removed and left to bleed for 30 sec. | 3 | The novel sealant partially stopped the massive bleeding by creating a biomimetic film. Complete hemostasis was not achieved since the sealant did not cover the entire wound. |
| Sealant #2 | 24 | 86 | A silicon mold | Another 1 cm biopsy was removed and excess blood was removed. The sealant was applied with hemostatic pressure. | 3 | The sealant did not cover the entire wound area, though hemostasis was achieved where the sealant was present. |
| Sealant #3 | 24 | 84 | Silicon mold | Another 0.5 cm biopsy was removed and excess blood was removed prior to application of the sealant. 9 mL of sealant were applied. | — | All sealant was displaced during the application process. |
| Sealant #4 | 24 | 80 | Transparent, flexible plastic mold with high margins | Another 1 cm biopsy was removed. 15 mL sealant were applied over the applicator, left 1 min 20 sec to cool and then placed over the wound site. | 4 | A thick layer of biomimetic clot was formed. Complete hemostasis was achieved. 50 min later the tissue was reexamined and hemostasis was still observed. The formed film was hard to remove and after |

TABLE 7-continued

Hemostasis in Left Liver Lobe

| Experiment | RT (° C.) | Heart Rate | Application Technique | Description | Time to Hemostasis (min) | Results |
|---|---|---|---|---|---|---|
| | | | | | | removal some bleeding continued. |

Hemostasis in Femoral Artery

Next, the ability of the composition of the present invention to induce hemostasis in wounds or trauma to an artery, specifically the femoral artery, was examined. The animal's right femoral artery was exposed. Then, a circular 2 mm longitudinal cut was preformed using a surgical blade. Massive bleeding was observed and therefore a hemostat was used. Excess blood was removed using a cotton gauze pad immediately prior to application of the sealant. About 9 mL Novel Surgical Sealant were prepared and applied using a syringe over the wound area. After 4 min, the hemostat was gently removed and hemostasis via the sealant was examined. A biomimetic clot was observed and complete hemostasis was reached. Table 9 summarizes the experimental procedure and results of this experiment.

TABLE 9

Hemostasis in Femoral Artery

| Experiment | RT (° C.) | Heart Rate | Application Technique | Description | Time to Hemostasis (min) | Results |
|---|---|---|---|---|---|---|
| Sealant #1 | 24 | 96 | A syringe | 2 mm punch was performed and a hemostat was used to stop the massive bleeding. ~9 mL of sealant solution were applied over the wound site using a syringe. After 4 min the hemostat was gently removed. | 4 | After removal of the hemostat complete hemostasis was observed. The sealant created a biomimetic clot over the wound site that managed to block the massive bleeding. |

Example 5

Protocol

Effect of Guanidine Hydrochloride on Gelation and Cross Linking

This Example relates to the effect of an exemplary denaturant, guanidine hydrochloride (described herein as "GuCl"), on compositions according to some embodiments of the present invention. A preferred concentration ratio range is as follows: from about 1:2 to about 2:2 GuHCl: gelatin, weight per weight.

Solution Preparation 1) 10 g of GuCl (Fluka, St. Louis, Mo.) was dissolved in 30 mL of Dulbecco's PBS (Biological Industries, Israel) at room temperature (RT). 10 g of type A, 300 bloom porcine gelatin powder (Sigma, St. Louis, Mo.) was weighed separately. Gelatin and GuCl solution were then mixed under moderate stirring to form a homogenous solution. The resulting solution had a gelatin:GuCl ratio (w:w) of 1:1.

The molecular weight (MW) of GuCl is 95.53. In this solution, the final concentration of GuCl was thus 3.489 M. Final solution was 20% gelatin w/w, but according to volume, equivalent to 25% w/w gelatin solution in PBS.

2) 2 g of GuCl was dissolved in 30 mL of PBS at RT. 10 g of type A, 300 bloom porcine gelatin powder was weighed separately. Gelatin and GuCl solution were then mixed under moderate stirring to form a homogenous solution. Resulting solution had gelatin:GuCl ration (w:w) of 5:1. Final concentration of GuCl was 698 mM. Final solution was 23.8% gelatin w/w, but according to volume, equivalent to 25% w/w gelatin solution in PBS.

3) 6 g of GuCl was dissolved in 30 mL of PBS at RT. 10 g of type A, 300 bloom porcine gelatin powder was weighed separately. Gelatin and GuCl solution were then mixed under moderate stirring to form a homogenous solution. Resulting solution had gelatin:GuCl ration (w:w) of 5:3. Final concentration of GuCl was 2.09 M. Final solution was 21.7% gelatin w/w, but according to volume, equivalent to 25% w/w gelatin solution in PBS.

4) 4 g of GuCl was dissolved in 30 mL of PBS at RT. 10 g of type A, 300 bloom porcine gelatin powder was weighed separately. Gelatin and GuCl solution were then mixed under moderate stirring to form a homogenous solution. Resulting solution had gelatin:GuCl ration (w:w) of 5:2. Final concentration of GuCl was 1.40 M. Final solution was 22.7% gelatin w/w, but according to volume, equivalent to 25% w/w gelatin solution in PBS.

5) 8 g of GuCl was dissolved in 30 mL of PBS at RT. 10 g of type A, 300 bloom porcine gelatin powder was weighed separately. Gelatin and GuCl solution were then mixed under moderate stirring to form a homogenous solution. Resulting solution had gelatin:GuCl ration (w:w) of 5:1. Final concentration of GuCl was 2.79 M. Final solution was 20.8% gelatin w/w, but according to volume, equivalent to 25% w/w gelatin solution in PBS.

Addition of mTG

A 20% w/w solution of 1% microbial transglutaminase powder (mTG) (Ajinomoto Activa TI-WM, Japan) in PBS was prepared.

A) 2 mL of each gelatin-GuCl solution was mixed with 1 mL of mTG solution in clear, 4 mL plastic tubes. mTG solution was injected into the gelatin-GuCl solution. Each tube was inverted several times and then allowed to stand.

B) 2 mL of each gelatin-GuCl solution was mixed with 1 mL of mTG solution in plastic weighing dishes. Mixtures were manually mixed with a pipette tip.

C) Gelatin-GuCl solutions were heated to 43° C. and then 2 mL aliquots of gelatin-GuCl solutions were mixed with 1 mL of mTG solution in plastic weighing dishes. Mixtures were manually mixed with a pipette tip.

D) Gelatin-GuCl solutions 1 (10 g GuCl) and 5 (8 g GuCl) was heated to 43° C. and then 2 mL aliquots of gelatin-GuCl solutions were mixed with 2 mL of mTG solution in plastic weighing dishes. Mixtures were manually mixed with a pipette tip.

Results 1) 1:1 gelatin:GuCl solution formed a homogenous solution at RT within 2 minutes. Immediately after formation, solution contained many bubbles. After 2 hrs standing at RT, nearly all of the air bubbles had left the solution. The solution remained in liquid form and appeared clear with a yellow tint, like standard gelatin solutions. After 24 hours, solution properties were unchanged and no more bubbles were visible.

2) 5:1 gelatin:GuCl did not form a homogenous solution at RT. Gelatin granules were swollen but did not dissolve, as would normally occur with gelatin in PBS at RT. Solution was heated to 42° C. until it formed a solution. Upon cooling to RT, it formed a gel at approximately 32° C.

3) 5:3 gelatin:GuCl formed a homogenous solution at RT after 5-6 minutes of vigorous stirring. Immediately after formation, solution contained many bubbles. After 2 hrs standing at RT, nearly all of the air bubbles had left the solution. The solution remained in liquid form and appeared clear with a yellow tint, like standard gelatin solutions. Solution was in liquid form but more viscous than the 1:1 gelatin:GuCl solution. However, it could still be pipetted without difficulty. After 24 hours, solution properties were unchanged and no more bubbles were visible.

4) 5:2 gelatin:GuCl formed a slightly grainy solution at RT after 10 minutes of vigorous stirring Immediately after formation, solution contained many, many bubbles Immediately after formation, the solution appeared to be very viscous but still in liquid form. However, after 2 hrs standing at RT, many air bubbles were still visible in the solution and the solution was gelatinous. The solution could not easily be pipetted and was too viscous to mix with other solutions. After 24 hours, many air bubbles remained in the solution and the solution had formed a thermoreversible gel.

5) 5:4 gelatin:GuCl formed a homogenous solution at RT after 2-3 minutes of stirring. Immediately after formation, solution contained many bubbles. After 2 hrs standing at RT, nearly all of the air bubbles had left the solution. The solution remained in liquid form and appeared clear with a yellow tint, like standard gelatin solutions. The solution was in liquid form, more viscous than the 1:1 gelatin:GuCl solution but less than the 5:3 gelatin:GuCl solution, and could be pipetted without difficulty. After 24 hours, the solution properties were unchanged and no more bubbles were visible.

mTG Results

A) 2 mL Gelatin-GuCl Solution, 1 mL mTG Solution at RT in 4 mL Tube

1) For the 1:1 gelatin:GuCl solution, a small, gelatinous clump was formed near the top of the tube after 4 minutes. The clump was removed and an additional 1 mL of mTG solution was added. After 35 minutes, a soft-medium gel was formed. The clump was not thermoreversible, as confirmed by microwave heating. However, it was also not strongly cohesive as a cross-linked gel would be. The soft-medium gel was confirmed, using microwave heating, to be thermally irreversible.

2) The 5:1 gelatin:GuCl solution was too viscous to mix with the mTG.

3) For the 5:3 gelatin:GuCl solution, a small, gelatinous clump was formed near the top of the tube after 4 minutes. It was not removed. After 20 minutes, a medium gel was formed throughout the solution. The clump was of a distinctly different consistency than the rest of the gel. As above, though it was not thermoreversible, as confirmed by microwave heating, it was also not very cohesive and broke apart easily when palpated. The medium gel formed became slightly softer upon heating in the microwave, but was thermally irreversible.

4) Results for the 5:2 gelatin:GuCl solution were very uneven as the solution became very viscous during the first few minutes after mTG addition as a result of thermoreveresible gelation (indicated by control solution where mTG was not added). After 15 minutes, a moderately firm gel was formed but it was partially thermoreversible and became much softer upon heating.

5) For the 5:4 gelatin:GuCl solution, a small, gelatinous clump was formed near the top of the tube after 4 minutes. It was not removed. After 30 minutes, a medium gel was formed throughout the solution. The clump was of distinctly different consistency than the rest of the gel. As above, though it was not thermoreversible, as confirmed by microwave heating, it was also not very cohesive and broke apart easily when palpated. The medium gel formed became slightly softer upon heating in the microwave, but was thermally irreversible.

B) 2 mL Gelatin-GuCl Solution, 1 mL mTG Solution at RT in a Plastic Dish

The gelation time results for the solutions mixed in a plastic dish were nearly identical to those found in the solutions mixed in a 4 mL plastic tube: 1:1 gelatin:GuCl formed a soft-medium gel after 35 minutes, 5:3 gelatin:GuCl formed a medium gel after 20 minutes, 5:4 gelatin:GuCl formed a medium gel after 30 minutes.

However, the gelatinous clumps observed when the mTG was injected into the gelatin-GuCl solutions was not observed in these experiments.

C) 2 mL gelatin-GuCl solution at 43° C., 1 mL mTG solution in a plastic dish—the results were as follows: for the 1:1 gelatin: GuCl solution, no gel was formed after 35 minutes; for the 5:3 gelatin:GuCl solution, a medium gel was formed after 17 minutes; for the 5:4 gelatin:GuCl solution, a medium gel was formed after 25 minutes.

D) 2 mL gelatin-GuCl solution at 43° C., 2 mL mTG solution in a plastic dish, the results were as follows: for the 1:1 gelatin:GuCl solution, no gel was formed after 25 minutes; for the 5:4 gelatin:GuCl solution, a medium gel was formed after 9 minutes.

From the above results, it was found that GuCl significantly improves the solubility of gelatin in PBS. For concentrations of 25% w/w gelatin in PBS, the addition of GuCl at ratios of 5:4 and 1:1 gelatin:GuCl allow gelatin to dissolve in RT PBS almost immediately. This effect is significantly decreased at a ratio of 5:3 gelatin:GuCl. For concentrations of 25% w/w gelatin in PBS, the addition of GuCL at ratios of 5:3, 5:4, and 1:1 gelatin:GuCl can maintain the gelatin-GuCl solution in liquid form indefinitely. At a ratio of 5:2 gelatin:GuCl, the solution undergoes delayed thermoreversible gelation and forms a full gel after 2 hours. At a ratio of 2:1, gelatin-GuCl solution:mTG solution, no gel was formed if the gelatin:GuCl solution ratio is 1:1. At lower GuCl concentrations, cross-linked gels were formed. Gelation time appears to be dependant on GuCl concentration.

Heating the gelatin-GuCl solution to 43° C. prior to mixture with mTG accelerates the cross-linking process when the gelatin:GuCl ratio is 5:4 and 5:3. This was expected as mTG activity increases with increases in reaction temperature up to 55° C. It is likely that if mTG activity is increased, gelatin:GuCl solutions will be cross-linked more rapidly by mTG.

At a ratio of 1:1, gelatin-GuCl solution:mTG solution, cross-linked gels were formed even when the gelatin:GuCl solution ratio is 1:1. The increase in mTG amount greatly decreased the gelation time of gels that did form gels at a gelatin:GuCl solution:mTG solution ratio of 2:1. Gelation time was observed to be dependant on GuCl concentration. This was expected as well as the GuCl likely denatures a certain amount of mTG. The mTG that is added above that amount is free to cross-link gelatin.

Without wishing to be limited by a single hypothesis, it is possible that if more mTG enzyme is added, gelatin:GuCl solutions would be cross-linked much more rapidly by mTG. This can be accomplished, for example, optionally by removing the carrier from the mTG powder and forming a concentrated solution of the enzyme itself.

Example 6

Protocol

Addition of $MgCl_2$ to Gelatin—Effect on Gelation and Cross Linking

This Example relates to the effect of an exemplary reducing agent, magnesium chloride, on compositions according to some embodiments of the present invention. A preferred concentration range for dissolving gelatin into Magnesium Chloride-PBS solution is preferably from about 2 to about 4 M, more preferably from about 2.5 to about 3.5M.

Materials and Methods

Materials

Type A 300 bloom porcine gelatin and MgCl2 powder, −325 mesh were obtained from Sigma-Aldrich corporation (St. Louis, Mo.). Activata TI-WM microbial transglutaminase (mTG) was supplied by Ajinomoto (Japan). Dulbecco's PBS (pH 7.4) was obtained from Biological Industries (Kibbutz Beit HaEmek, Israel).

mTG Solution Preparation:

Fresh Activa TI-WM (Ajinomoto, Japan) microbial transglutaminase (mTG) mixture was prepared by dissolving in Dulbecco's PBS to form a 20% w/w solution. The solution was maintained at room temperature (RT) over the course of the experiment.

Gelatin-MgCl2 Solution Preparation:

Gelatin was dissolved in different concentrations of MgCl2 solutions as follows.

Solution A—5 gr of MgCl2 was dissolved in 15 ml of Dulbecco's PBS to a final concentration of 3.5 M. The dissolution reaction of MgCl2 is exothermic, reaching to 90° C. The solution was left to cool to RT. 25% gelatin aliquot (w/w) was prepared by dissolving 5 gr of gelatin in 15 gr of 3.5M MgCl2 solution and stirring at RT.

Solution B— 2.5 gr of MgCl2 was dissolved in 15 ml of Dulbecco's PBS to a final concentration of 1.75 M. The dissolution reaction of MgCl2 is exothermic, reaching to 63° C. The solution was left to cool to RT. 25% gelatin aliquot (w/w) was prepared by dissolving 5 gr of gelatin in 15 gr of 63° C. 1.75M MgCl2 solution and stirring.

Effect of MgCl2 on Gelation of Gelatin:

Gelatin dissolved in MgCl2 solutions in different concentrations were left to cool to RT. A thermometer was used to follow the temperature of each solution. The appearance and viscosity of the gelatin-MgCl2 solutions were assessed as the temperature decreased by observation and palpating the solution with a glass rod.

MgCl2 Effect on Chemical Cross Linking of Gelatin Solutions Using mTG:

Gelatin-MgCl2 "solution A" was tested for chemical cross linking using mTG. 1 or 2 ml of 20% w/w mTG solution were mixed with 2 ml of gelatin-MgCl2 solution in a 4 ml technicon tube. The gelatin-MgCl2 solution was added either at RT or preheated to 50° C. using a water bath. The solutions were mixed by gently stirring with the pipette tip and inverting the tube 4 times and time to gelation was measured. The appearance and viscosity of the gelatin-MgCl2 solutions after mixture with mTG were assessed by observation and by palpating the solution with a glass rod. When gel was formed it was tested for thermoreversibility by heating the gel to 50° C. using a water bath.

Results

Effect of MgCl2 on Gelation of Gelatin:

Solution A—3.5 M MgCl2 solution reduced transition point of gelatin. Gelatin-MgCl2 solution was viscous at RT. The solution appeared rather opaque and consisted small black particles. These particles are probably magnesium particles that gone oxidation. Solution B— 1.75 M gelatin-MgCl2 solution gelled at RT. The transition point was 29° C. The gel was opaque and consisted few black particles that probably formed by oxidation of Mg.

MgCl2 Effect on Chemical Cross Linking of Gelatin Solutions Using mTG:

MgCl2 effect on cross linking was tested with solution A, as follows. 2 ml of RT solution A mixed with 1 ml of mTG solution-Irreversible gel was produced after 90 min. The gel was very viscous and somewhat soft. 2 ml of 50° C. heated solution A mixed with 1 ml of mTG solution-Irreversible gel was produced after 70 min 2 ml of 50° C. heated solution A mixed with 2 ml of mTG solution-Irreversible gel was produced after 25 min the gel was rather weak. The gel's viscosity increased after heating it in a 50° C. water bath.

From the above, it appears that addition of magnesium chloride to gelatin solutions decreases the transition point of gelatin significantly. It appears that the transition point is inversely proportional to the magnesium chloride concentration. The transition point is reduced to below RT by the addition of 3.5 M of magnesium chloride. At 1.75 M of magnesium chloride, the transition point of the gelatin solutions is slightly above RT. The addition of magnesium chloride to gelatin should be optimized to find the minimum concentration that reduces the gelatin transition point below RT.

It was also shown that cross linking of gelatin using mTG in the presence of magnesium chloride is possible. Magnesium chloride has a detrimental effect on the cross linking ratio of gelatin. Adding further amounts of mTG may optionally be performed to overcome this effect.

mTG activity at 50° C. is far greater than mTG activity at RT. This confirms the theoretical data and indicates the utility of adding an exothermic element into the gelatin-mTG mixture to ensure a reaction temperature that is higher than RT.

The exothermic dissolution of magnesium chloride may optionally be used for both liquefying gelatin and increasing mTG's activity, from the above data.

Example 7

Protocol

Addition of Hydroquinone to Gelatin—Effect on Gelation and Cross Linking

This Example relates to the effect of an exemplary reducing agent, hydroquinone, on compositions according to some embodiments of the present invention. Hydroquinone is a naturally occurring, water soluble reducing agent. Reducing agents can increase gelatin's solubility, allowing it to remain liquid at room temperature (RT). A preferred concentration range is preferably determined for dissolving gelatin into hydroquinone-PBS solution at concentration of from about 0.2 to about 0.5 M, and more preferably from about 0.3 to about 0.4 M.

Materials and Methods

Materials

Type A 300 bloom porcine gelatin and Hydroquinone (ReagentPlus™, >99%) were obtained from Sigma-Aldrich corporation (St. Louis, Mo.). Activata TI-WM microbial transglutaminase (mTG) was supplied by Ajinomoto (Japan). Dulbecco's PBS (pH 7.4) was obtained from Biological Industries (Kibbutz Beit HaEmek, Israel).

mTG Solution Preparation:

Fresh Activa TI-WM (Ajinomoto, Japan) microbial transglutaminase (mTG) mixture was prepared by dissolving in Dulbecco's PBS to form a 20% w/w solution. The solution was maintained at room temperature (RT) over the course of the experiment.

Gelatin-Hydroquinone Solution Preparation:

Gelatin was dissolved in different concentrations of Hydroquinone solutions as follows. Solution A—2.75 gr of hydroquinone was dissolved in Dulbecco's PBS to a final concentration of 0.5 M. Throughout the experiment the solution was kept at a sealed beaker, wrapped in aluminum foil, to avoid its exposure to air and light. 25% gelatin aliquot (w/w) in 0.5 M hydroquinone solution was prepared by mixing 5 gr of gelatin with 15 gr of 0.5 M hydroquinone solution and stirring.

Solution B— 1.32 gr of hydroquinone was dissolved in Dulbecco's PBS to a final concentration of 0.4 M. Throughout the experiment the solution was kept at a sealed beaker, wrapped in aluminum foil, to avoid its exposure to air and light. 25% gelatin aliquot (w/w) in 0.4 M hydroquinone solution was prepared by mixing 5 gr of gelatin with 15 gr of 0.4 M hydroquinone solution. The mixture was stirred and then heated in a 50° C. water bath.

Effect of Hydroquinone on Gelation of Gelatin:

Solutions of gelatin dissolved in different concentrations of hydroquinone were either kept at RT or heated at a 50° C. water bath and then cooled to RT. A thermometer was used to follow the temperature of each solution. The appearance and viscosity of the gelatin-hydroquinone solutions were assessed as the temperature decreased by observation and palpating the solution with a glass rod.

Hydroquinone Effect on Chemical Cross Linking of Gelatin Solutions Using mTG:

Gelatin-Hydroquinone "solution B" was tested for chemical cross linking using mTG. 1 ml of 20% w/w mTG solution was mixed with 2 ml of gelatin-hydroquinone solution, heated to 50° C., in a 4 ml technicon tube. The solutions were mixed by gently stirring with the pipette tip and inverting the tube 4 times and time to gelation was measured. The appearance and viscosity of the gelatin-hydroquinone solution after mixture with mTG was assessed by observation and by palpating the solution with a glass rod. When gel was formed it was tested for thermoreversibility by heating the gel to 50° C. using a water bath.

Results

Effect of Hydroquinone on Gelation of Gelatin

Solution A—0.5 M of hydroquinone solution at RT did not dissolve gelatin. Gelatin powder soaked in the hydroquinone solution, creating a grainy, brown colored, heterogeneous solution. Solution B— 0.4 M of hydroquinone solution managed to reduce the transition point of gelatin. Hydroquinone solution did not dissolve gelatin at RT. After heating the mixture at 50° C. water bath, gelatin dissolved and a homogenous solution was obtained. The solution was cooled to RT. At 28° C. gelatin remained soluble, but was very viscous. Gel was formed when cooled to RT. The gel was brown colored.

Hydroquinone Effect on Chemical Cross Linking of Gelatin Solutions Using mTG:

The effect on cross linking was tested with solution B. 2 ml of solution B heated to 50° C. was mixed with 1 ml of mTG solution. After 4 min irreversible gel was formed. The gel was strong, resembling cross linked gel that is formed by mixture of 25% (w/w) of gelatin alone with 20% (w/w) of mTG.

From the above it appears that addition of Hydroquinone to gelatin solutions decreases the transition point of gelatin. At 0.4 M of hydroquinone, the transition point of the gelatin solutions is slightly above RT (28° C.).

In contrast to other substances that have been tested as methods of reducing transition point of gelatin, hydroquinone did not have a significant inhibitory effect on the cross linking of gelatin with mTG.

Hydroquinone may optionally be used to reduce the sol-gel transition temperature of gelatin without negatively impacting mTG cross-linking of gelatin, as demonstrated the above data. This is very desirable for many embodiments of the present invention, as previously described.

Example 8

Protocol

Addition of $CaCl_2$ to Gelatin—Effect on Gelation and Cross-Linking

This Example relates to the effect of an exemplary desiccant, calcium chloride, on compositions according to some embodiments of the present invention. A preferred concentration range with regard to dissolving gelatin into Calcium Chloride-PBS solution is preferably in a range of from about 1 to about 2 M, to decrease the transition point of gelatin. To create an exothermic reaction that could help dissolve gelatin or increase mTG activity, approximately 0.2-0.7 g of Calcium Chloride per mL of solution is optionally and preferably added for each degree Celsius increase in temperature above the ambient temperature, though the exact amount depends on several factors.

A gelatin-calcium chloride solution in DPBS was prepared as follows: 4 M CaCl2 stock solution was prepared by dissolving 44.396 g of CaCl2 (97%, MW=110.99, Alfa Aesar, Lancaster) in 100 mL of Dulbecco's PBS (Biological Industries, Israel) under stirring. After dissolution, the solution reached a peak temperature of 80° C. as a result of the exothermic CaCl2 dissolution reaction.

Solution 1 was prepared as follows. 5 g of type A, 300 bloom porcine gelatin powder (Sigma, St. Louis, Mo.) was weighed. 25% w/w gelatin solutions in PBS-CaCl2 were formed by adding 15 g of different concentration PBS-CaCl2 solutions to the 5 g of gelatin. Gelatin-CaCl2 was mixed using stir bar as well as occasional manual stirring to disperse clumps. The CaCl2 concentrations tested were:
  a. 2M CaCl2 solution in PBS.
  b. 2M CaCl2 solution in PBS.
  c. 1M CaCl2 solution in PBS.

For both a & b, 2 mL of the gelatin-CaCl2 solution was mixed with 1 mL of 20% w/w microbial transglutaminase (mTG) powder solution, each in a 4 mL plastic tube. The mTG product used (Activa TI-WM, Ajinomoto, Japan) had a specific activity of approximately 100 U/g of mTG product powder.

Solution 2 was prepared as follows. A 20% w/w base solution of mTG was formed by dissolving 10 g of mTG powder into 40 mL of PBS.
  a. A 25% w/w gelatin solution was prepared by dissolving 5 g of gelatin in 15 mL PBS by heating gelatin-PBS mixture in microwave for 5 seconds and then 15 seconds. Solution was immediately stirred after each microwave heating period. The temperature after the second heating was 72° C. 3.325 g of CaCl2 was then added to form a 2M CaCl2 solution. The temperature after the CaCl2 addition was 74° C. Immediately after CaCl2 was dissolved and temperature measured, 2 mL of the gelatin-CaCl2 solution was mixed with 1 mL of 20% w/w microbial transglutaminase (mTG) powder solution in a 4 mL plastic tube.
  b. 5 g of gelatin powder was mixed with 3.33 g of CaCl2 powder. 30 mL of PBS were then stirred into this mixture to form a solution. Solution temperature upon dissolution reached 42° C. After homogenous solution was formed, 2 mL of the gelatin-CaCl2 solution was mixed with 1 mL of 20% w/w microbial transglutaminase (mTG) powder solution in a 4 mL plastic tube.

Solution 3 was prepared as follows. A 25% gelatin solution in 2M CaCl2-PBS (1a, above) was allowed to sit for 2 hours. Then, 2 mL of gelatin-CaCl2 solution were mixed with 2 mL of 20% w/w mTG solution in a 4 mL plastic tube.

Solution 4 was prepared as follows. After sitting for two hours, a 25% Gelatin solution in 2M CaCl2-PBS (1b, above) was heated to 43° C. Then, 2 mL of gelatin-CaCl2 solution were mixed with a. 1 mL of 20% w/w mTG solution; or b. 2 mL of 20% w/w mTG solution; each in a 4 mL plastic tube.

Results

Solutions were formed at all concentrations of CaCl2. Using a 2M CaCl2 solution (1a), a homogenous solution was formed and remained in liquid form. The solution was moderately viscous and contained many air bubbles. Prior to mixture with mTG solution, gelatin-CaCl2 solution was allowed to sit for 30 minutes to allow bubbles to disperse.

The second 2M solution (1b) was identical to the first except that it required more manual stirring to disperse a gelatin clump that had been formed.

Using a 1M CaCl2 (1c) solution, a homogenous solution was formed but started to gel after a few minutes. After 2 hours, a thorough thermoreversible gel had been formed. However, this gel was much softer than the thermoreversible gel normally formed by the gelatin at room temperature. The solution was too viscous to be mixed with mTG solution after half an hour.

After addition of the mTG solution to the 2M gelatin-CaCl2 solutions, the solutions became progressively more viscous over a 20 minute period but did not form a cohesive gel.

The heating of gelatin-CaCl2 solutions increased the gelling effect of the mTG. The microwave heated solution became progressively more viscous. After 20 minutes, a very soft, irreversible (as confirmed by heating to 50° C.) gel had been formed. The CaCl2 heated solution became progressively more viscous. After 20 minutes, a very soft, irreversible (as confirmed by heating to 50° C.) gel had been formed.

For the gelatin-CaCl2 (2M) solution mixed with 2 mL of 20% w/w mTG solution, a soft gel was formed after 10 minutes. After 20 minutes, a medium strength gel was formed. After 35 minutes, a medium-firm strength gel was formed.

For the gelatin-CaCl2 (2M) solution heated to 43° C., after being mixed with 1 mL of 20% w/w mTG solution, a soft gel was formed after 10 minutes and a soft-medium strength gel was formed after 20 minutes. However, after being mixed with 2 mL of 20% w/w mTG solution, a medium strength gel was formed after 10 minutes and a medium-firm strength gel was formed after 20 minutes.

Example 9

Protocol

Microwave Drying of Gelatin—Effect on Gelation and Cross Linking

This Example examines the effect of drying gelatin in a microwave on solubility. Increased solubility was observed. An optional but preferred microwave radiation range of energy preferably features an overall specific absorption rate (SAR) of from about 1 to about 100 mW/cubic centimeter, more preferably of from about 30 to about 60 mW/cubic centimeter. The method was performed as follows.

Gelatin Preparation and Drying 10 gr. portions of type A, 300 bloom porcine gelatin powder (Sigma, St. Louis, Mo.) were weighed into either 50 mL or 250 mL beakers. The gelatin was then heated in a microwave at 700 W and 2,450 MHz (Kennedy model KN-949, China) for the following amounts of time:
  Sample A: 30 seconds, 50 mL beaker
  Sample B: 60 seconds, 250 mL beaker
  Sample C: 120 seconds, 250 mL beaker
  Sample D: 180 seconds, 250 mL beaker
  Control: Gelatin that has not undergone microwave heating After heating, 30 mL of Dulbecco's PBS (Biological Industries, Israel) at 37° C. was added to the gelatin and the mixture was stirred at 37° C. For Sample A, the PBS was immediately added after the gelatin was removed from the microwave. For the rest of the samples, the gelatin was allowed to cool to room temperature (RT) prior to the addition of the PBS.

For sample C, after gelatin was mixed with the PBS, part of the mixture was separated, heated to 50° C. and then mixed with a 20% w/w microbial transglutaminase (mTG) (Ajinomoto Activa TI-WM, Japan) solution according to a 2:1 gelatin solution:mTG solution ratio.

Microwave Heating of Gelatin/PBS Mixture

In Sample F, the gelatin was not heated in powder form. Rather, the gelatin was poured directly into 30 mL of RT PBS in a 50 mL beaker and then the mixture was heated in the microwave for 15 seconds twice consecutively, with a 5 second pause in between the heating periods. After the heating, it was manually stirred. The gelatin solution was then mixed with a 20% w/w mTG solution according to a 2:1 gelatin solution:mTG solution ratio.

Heating of mTG

20% w/w mTG solution was heated in the microwave for 15 seconds twice consecutively, with a 5 second pause in between the heating periods. The mTG was then added to 25% w/w gelatin solution in a 1:2 mTG:gelatin solution ratio.

Results

Sample A: The gelatin dissolved easily into the PBS, forming a viscous solution. When cooled to RT, the gelatin solution formed a firm thermo-reversible gel comparable to the thermo-reversible gel formed by standard gelatin solutions at RT.

Control: The gelatin did not fully dissolve in the PBS. Though it was fully soaked in PBS, the gelatin remained very grainy.

Sample B: The gelatin did not fully dissolve in the PBS. Though it was fully soaked in PBS, the gelatin remained very grainy.

Sample C: The gelatin did not fully dissolve in the PBS. Though it was fully soaked in PBS, the gelatin remained very grainy. The grainy gelatin-PBS mixture was then heated in the microwave for 30 seconds. The temperature upon removal from the microwave was 76° C. The mixture was then manually stirred to form a homogenous solution. The solution was allowed to cool to RT and formed a thermo-reversible gel comparable to the thermo-reversible gel formed by standard gelatin solutions at RT.

When the solution was heated to 50° C. and mixed with mTG, a firm and sticky gel was formed after 3 minutes. This gel was heated for 10 seconds in the microwave to confirm its irreversibility. Upon exit from the microwave, the gel was stickier but stronger. It appeared to be slightly dry.

Sample D: During heating, the gelatin formed a carbonized bubble. The bubble was formed inside the gelatin powder by burnt gelatin. A strong burning smell accompanied this occurrence.

Heated Gelatin/PBS Mixture: A liquid solution was formed by heating of the gelatin/PBS mixture in the microwave. Addition of mTG to the solution resulted in a firm irreversible gel.

Heated mTG: The mTG that had been heated in the microwave did not cross-link gelatin.

From the above, it appears that heating gelatin powder in a microwave reduces the moisture content of the gelatin, as indicated by significant reductions in the weight of the gelatin (data not shown). Heating gelatin powder in the microwave, followed by immediate addition of 37° C. PBS reduces the gelatin dissolution time. However, if the gelatin powder is cooled to RT, then no improvement in gelatin dissolution time occurs.

If microwave heated gelatin is microwave heated after it has been mixed with PBS, then the solution formed can be cross-linked by mTG. It is possible to dissolve gelatin in RT PBS and then heat it in a microwave by heating for 15 s and then again by 15 s. Dissolving it in this way does not negatively affect mTG cross-linking.

Dry gelatin will burn if heated in the microwave for more than 2 minutes. Heating mTG in the microwave drastically reduces its activity.

Example 10

Effect of Urea on Gelation and Cross Linking of Gelatin

This Example relates to the effect of urea as part of an exemplary composition according to the present invention. Urea was found to lower the transition point of gelatin solutions. The below data confirms that it sufficiently lowers the transition point of even high concentration gelatin solution to below room temperature so that the solution is still in liquid form at room temperature. Transglutaminase was found to be able to cross-link gelatin even in the presence of urea.

Gelatin Solution Preparation:

Type A 300 bloom porcine gelatin (Sigma, St. Louis, Mo.) was used. 25% and 15% w/w gelatin solutions were prepared by dissolving 50 gr and 30 gr of gelatin in 150 ml and 170 ml of Dulbecco's PBS (Biological Industries, Israel), respectively, while stirring on hot plate at 50° C. Gelatin was added to PBS gradually and stirred manually using a glass rod. Gelatin solutions were kept in a water bath at 50° C. over the course of the experiment.

Transglutaminase Solution Preparation:

Activa TI-WM (Ajinomoto, Japan) microbial transglutaminase (mTG) mixture was dissolved in Dulbecco's PBS to form a 20% w/w solution. The solution was maintained at room temperature (RT) over the course of the experiment.

Gelatin-Urea Solution Preparation:

40 g aliquots of 25% or 15% w/w gelatin solutions was transferred to 100 ml beakers and stirred at 50° C. Urea (98%, Alfa Aesar, Lancaster, UK) was added to these beakers in different ratios, as detailed in the below table:

| Gelatin % | | Gelatin:Urea ratio | Amount of added Urea (gr) |
|---|---|---|---|
| 25% | Solution 1 | 1:0 | 0 (Control) |
|     | Solution 2 | 1:1 | 10 |
| 15% | Solution 3 | 1:0 | 0 (Control) |
|     | Solution 4 | 1:0.5 | 2.65 |
|     | Solution 5 | 1:1 | 5.3 |
|     | Solution 6 | 1:1.5 | 8.025 |

After urea addition, the gelatin-urea solution was stirred at 50° C. for 5 min to ensure homogeneity and then transferred to a 37° C. water bath.

Effect of Urea on Thermo-Reversible Gelation of Gelatin:

Each gelatin-urea solution was removed, in turn, from the 37° C. water bath and left to cool at RT. A thermometer was used to follow the temperature decrease of each solution. The appearance and viscosity of the gelatin-urea solution were assessed as the temperature decreased by observation and palpating the solution with a glass rod. Results of this experience are described at the following table:

| Gelatin % (w/w) | Gelatin:Urea ratio | Results |
|---|---|---|
| 25% | Solution 1  1:0 | At 25° C., the gelatin formed a firm thermo-reversible gel. |
|  | Solution 2  1:1 | At 25° C., the solution remained in liquid form. Though slightly viscous, it could be easily pipetted. |
| 15% | Solution 3  1:0 | At 25° C., the gelatin formed a firm thermo-reversible gel. |
|  | Solution 4  1:0.5 | At temperatures >26° C., the solution remained significantly more liquid than gelatin alone. However, at RT (23-25° C.), solution formed gel. |
|  | Solution 5  1:1 | At 25° C., the solution remained in liquid form. After refrigeration at 4° C. and return to 25° C., solution returned to liquid form. |
|  | Solution 6  1:1.5 | At 25° C., the solution remained in liquid form. After refrigeration at 4° C. and return to 25° C., solution returned to liquid form. |

Cross Linking of Gelatin-Urea Solution Using mTG:

Gelatin-urea solutions were cross linked using mTG. 1 or 2 ml of 20% w/w mTG solution was manually mixed with 2 ml of gelatin-urea solution in a plastic dish. The gelatin-urea solution was added either at RT or preheated to 50° C. In some tests, it was heated to 50° C. to facilitate comparison with gelatin alone, which needs to be heated to be mixed with mTG. The solutions were mixed by gently stirring with the pipette tip and left to cross-link for several minutes. As in examination of thermo-reversible gel formation, the appearance and viscosity of the gelatin-urea solution after mixture with mTG were assessed by observation and by palpating the solution with a glass rod. The results are summarized in the following table:

| Gelatin % (w/w) | Gelatin:Urea ratio | T ° C. of solution | Amount of mTG added (ml) | Results |
|---|---|---|---|---|
| 25% | Solution 1  1:0 | 50° C. | 1 | Normal cross-linking: gelation after 3 minutes. |
|  | Solution 2  1:1 | RT | 1 | No gel was formed, even after 30 min. |
|  |  |  | 2 | Soft, sticky gel was formed after 30 minutes |
|  |  | 50° C. | 1 | No gel was formed, even after 30 min. |
|  |  |  | 2 | Soft, sticky gel was formed after 10 min. Firm, slightly brittle gel was observed after 30 min. |
| 15% | Solution 3  1:0 | 50° C. | 1 | Normal cross-linking: gelation after 3 minutes. |
|  | Solution 4  1:0.5 | 50° C. | 1 | Gelation was observed after 6 min. Complete gelation was observed after 20 min. Gel was heated in a 50° C. bath yet remained a firm gel. |
|  | Solution 5  1:1 | RT | 1 | After 12 min gelation began, creating soft gel. After 30 min the gel appears firm. The gel remained firm even after heating in a 50° C. water bath. |

The above studies show that addition of urea to gelatin solutions decreases the transition point of gelatin significantly. For both 15% and 25% w/w gelatin solutions, the transition point is reduced to below RT by the addition of urea at ratios of 1:1 urea:gelatin and above. At urea:gelatin ratios of 0.5:1, the transition point of the gelatin solutions is slightly above RT. It is likely that a urea:gelatin ratio between 0.5:1 and 1:1 will suffice to lower the transition point of gelatin below RT.

It was also shown that cross-linking of gelatin using mTG in the presence of Urea is possible. However, urea has a detrimental effect on mTG activity. It appears that this effect is relative to urea concentration, such that mTG activity in the presence of urea is inversely proportional to the urea concentration.

Transglutaminase activity at 50° C. was far greater than mTG activity at RT, as would be expected. The addition of urea to gelatin can be optimized to find the minimum concentration that reduces the gelatin transition point below RT. If a sufficient amount of mTG is added, it should be able to overcome the detrimental effect of urea.

Example 11

Effect of pH on Gelatin Transition Point

This Example demonstrates the effect of changing the pH of gelatin solutions on the transition point of those gelatin solutions.

Solution Preparation 58.82 gr. of 99% sodium citrate dihydrate (Alfa Aesar, Lancaster, UK) were dissolved in 100 mL of double distilled water to create a 2M stock solution of sodium citrate. A base solution of 25% w/w gelatin solution in Dulbecco PBS (Biological Industries, Israel) was prepared using type A, 300 bloom porcine gelatin (Sigma, St. Louis, Mo.). The gelatin solution was continuously stirred and maintained at 50° C. 19.21 gr. of citric acid anhydrous (Frutarom, Israel) was dissolved in 50 mL of double distilled water to create a 2M stock solution of citric acid.

pH Measurements

The pH of the solution was measured using a pH meter (Eutech pH510, Singapore) with a glass electrode. pH meter was calibrated prior to experiment using calibration solutions with pH values of 4.01, 7, and 10.01. The accuracy of the pH measurement was determined periodically over the course of the experiment. The pH of the 2M sodium citrate solution was 8.54. The pH of the 2M citric acid solution was 1.4.

Addition of Sodium Citrate

A 20 mL aliquot of 25% w/w gelatin solution was separated into a 100 mL beaker, which was maintained at 50° C. with moderate stirring. The initial pH of the gelatin solution was measured to be 4.89. Different amounts of 2M sodium citrate solution were added to 20 mL gelatin solutions to form the following solutions:
Solution 1: pH of 5.87-2 mL of sodium citrate solution
Solution 2: pH of 6.55-4 mL of sodium citrate solution
Solution 3: pH of 6.7-6 mL of sodium citrate solution
Each solution was then allowed to cool to RT.
Addition of Citric Acid A 100 mL aliquot of 25% w/w gelatin solution was separated into a 250 mL beaker, which was maintained at 50° C. with moderate stirring. The initial pH of the gelatin solution was measured to be 5.19.

Different amounts of 2M citric solution were added to gelatin solutions to form the following solutions:
Solution 1: pH of 3.99
Solution 2: pH of 3.54
Solution 3: pH of 2.72
Solution 4: pH of 2.35
Solution 5: pH of 2.17
Solution 6: pH of 2.04
Solution 7: pH of 1.7
Each solution was then allowed to cool to RT.
Sodium Citrate Results As sodium citrate was added, the addition formed a cloudy, white clump in the gelatin solution. Vigorous stirring dispersed the clump, first into smaller clumps, and then into a homogenous solution. The homogenous solution that was formed was cloudy and opaque.

At a pH value of 5.87, the gelatin solution aliquot that was allowed to cool formed a thermo-reversible gel in approximately the same amount of time that gelatin alone forms a thermo-reversible gel.

At a pH value of 6.55, the gelatin solution aliquot that was allowed to cool formed a thermo-reversible gel very rapidly, in under a minute. This was far faster than gelatin alone.

At a pH value of 6.70, the aliquot formed a thermo-reversible gel almost instantaneously. After the gelatin-sodium citrate solution was left at 50° C. for several minutes, the entire solution formed a gel. The transition point had increased to a point above 50° C.

At all pH values, the gels were demonstrated to be thermo-reversible as they all reverted to liquid form after immersion in 60° C. water Citric Acid Results A clear difference in transition point was not observed at pH values above 3.54. At the pH value of 3.54, the gelatin solution remained liquid from 50° C. until approximately 32° C., at which point a very sticky gel was formed.

At a pH value of 2.72, the transition point was approximately 31° C. and the gel formed was porous: grainy, with many air bubbles.

At a pH value of 2.04, the transition point dropped to 29° C. The gel formed was more porous than the gel formed at a pH value of 2.72.

At a pH value of 1.7, the transition point dropped to 27-28° C. The gel formed was quite porous.

At all pH values, the gels were demonstrated to be thermo-reversible as they all reverted to liquid form after immersion in 50° C. water.

However, after the gels were left in the 50° C. water for 30 minutes, a gel was formed that did not revert to liquid form. This may have indicated that the citric acid resulted in cross-linking of gelatin after 30 minutes at 50° C.

The above shows that lowering the pH of a gelatin solution through addition of citric acid can significantly decrease the gel transition point. The addition of citric acid, which decreases the gelatin solution pH to values down to 2, does not result in cross-linking of the gelatin. Further additions of citric acid to lower the pH below 2 may result in cross-linking of the gelatin after 30 minutes at 50° C.

Example 12

Effect of Polyhydric Alcohols on Gelation and Cross Linking of Gelatin

This Example relates to the effect of polyhydric alcohols such as sorbitol on gelatin cross linking.
Materials and Methods
Materials Type A 300 bloom porcine gelatin and 97% D-sorbitol were obtained from Sigma-Aldrich corporation (St. Louis, Mo.). Glycerol 99% was purchase from Frutarom (Israel). Activata TI-WM microbial transglutaminase (mTG) was supplied by Ajinomoto (Japan). Dulbecco's PBS (pH 7.4) was obtained from Biological Industries (Kibbutz Beit HaEmek, Israel).
mTG Solution Preparation:

Fresh Activa TI-WM (Ajinomoto, Japan) microbial transglutaminase (mTG) mixture was prepared by dissolving in Dulbecco's PBS to form a 20% w/w solution. The solution was maintained at room temperature (RT) over the course of the experiment.
Gelatin-Polyhydric Alcohol Solutions Preparation:

Solution A—10 gr. of glycerol was dissolved in 30 ml PBS. 10 gr of gelatin were then soaked in the glycerol solution for 1.5 hours at RT. After 1.5 hours of soaking, 10 ml of PBS were added and the mixture was heated to 50° C. The mixture was manually stirred until a homogenous, liquid solution (1:1 glycerol:gelatin ratio) formed.

Solution B—27.5 ml of 20% w/w gelatin solution was heated to 50° C. while being stirred. 11 gr glycerol was added to the gelatin solution (2:1 glycerol:gelatin ratio). The glycerol-gelatin solution was then allowed to cool. The 2:1 glycerol:gelatin solution was allowed to soak for 1.5 h at 50° C. The solution was then removed and allowed to cool at RT.

Solution C—20% gelatin solution containing glycerol in a 2:1 glycerol:gelatin ratio, was heated to 50° C. while being stirred. 11 gr of sorbitol was added to form a homogenous solution (glycerol:sorbitol:gelatin ratio of 2:2:1).

Solution D—12 gr of sorbitol was added to 20 ml of 20% w/w gelatin solution at 50° C. to form a homogenous solution with a sorbitol:gelatin ration of 3:1. The solution was then allowed to cool.

Solution E—A 5:1 glycerol:gelatin solution was prepared by adding 25 gr of RT glycerol to 20 ml of 20% w/w gelatin solution at 50° C. The mixture was mixed by stirring at 50° C.

Solution F—20 gr of sorbitol was added to 20 ml of 20% gelatin solution, resulting in a 5:1 sorbitol:gelatin ratio. The mixture was mixed at 50° C. The mixture was then cooled at RT.
Effect of Polyhydric Alcohol on Gelation of Gelatin:

As prepared with regard to the above description, 2 ml of gelatin solutions with polyhydric alcohols (see solutions A-F above) were removed and left to cool to RT. A thermometer was used to determine the temperature of each solution. The appearance and viscosity of the gelatin-polyhydric alcohol solutions were assessed as the temperature decreased by observation and palpating the solution with a glass rod.
Effect of Polyhydric Alcohols on Cross Linking of Gelatin Solutions Using mTG:

Gelatin-polyhydric alcohol solutions were tested for chemical cross linking using mTG. 1 ml of 20% w/w mTG solution was mixed with 2 ml of gelatin-polyhydric alcohol solutions in a small plastic dish. The gelatin-polyhydric alcohol solutions were added either at RT or preheated to 50° C. using a water bath. The solutions were manually mixed by gently stirring with the pipette tip and time to gelation was measured. The appearance and viscosity of the gelatin-polyhydric alcohol solutions after mixture with mTG were assessed by observation and by palpating the solution with a glass rod. When gel was formed it was tested for thermoreversibility by heating the gel to 50° C. using a water bath.

Results

Effect of Polyhydric Alcohol on Gelation of Gelatin:

Solution A—After soaking in the glycerol, the gelatin particles clumped together to form a very brittle, solid, grainy material. The presence of glycerol did not seem to slow thermoreversible gelatin gelation at all. A thermoreversible gel was formed in 2-3 minute, as occurs with 20% w/w gelatin solutions without glycerol. At 35° C., the gelatin-glycerol solution was very viscous, on the verge of gelation. As with the cooling to room temperature, the gelatin-glycerol phase transition was nearly identical to that of gelatin alone.

Solution B—As with the 1:1 glycerol:gelatin solution, glycerol at a ratio of 2:1 glycerol:gelatin did not lower the transition temperature of the gelatin. The solution was highly viscous at 35° C. and formed a cohesive gel at 33-34° C. Soaking the 2:1 glycerol:gelatin solution for 1.5 hours had no effect on the gelatin transition point. A thermoreversible gel started to form at 34° C.

Solution C—At 50° C., the gelatin-glycerol-sorbitol solution was more viscous than the gelatin-glycerol solution alone and was far more opaque. When this mixture was cooled, a gel formed at 35° C. The transition point was not lowered at all as a result of the sorbitol and glycerol.

Solution D—The gelatin-sorbitol solution started to gel at 40° C., indicating that high concentrations of sorbitol actually increase the gelatin transition point. At RT, the thermoreversible gel formed was far more elastic than gelatin gel alone.

Solution E—Even at the very high concentrations of 5:1 glycerol:gelatin ratio, the transition temperature of gelatin was not reduced. A thermoreversible gel formed as it would form with gelatin alone.

Solution F—A thermoreversible gel formed at 40° C. Very little difference was observed between the properties of 3:1 and 5:1 sorbitol:gelatin solutions. Both solutions slightly raised the transition point of gelatin but resulted in extremely sticky and elastic thermoreversible gels.

Effect of Polyhydric Alcohols on Cross Linking of Gelatin Solutions Using mTG:

Solution A—The gelatin-glycerol solution was turned into a stiff gel by the mTG in 3 minutes. The gel formed after 3 minutes was more cohesive than the gels formed by gelatin and mTG without glycerol over the same time period. The gel was reheated to 50° C. using a water bath and remained solid, confirming that mTG cross-linking was the mechanism of gelation.

Solution B—After 3 min, an irreversible gel formed. The gel was reheated to 50° C. using a water bath and remained solid, confirming that mTG cross-linking was the mechanism of gelation. As noted in the 1:1 glycerol:gelatin ratio solution, the presence of glycerol resulted in a firmer gel after 3 minutes. In the 2:1 glycerol:gelatin ratio solution, it was also observed that the formed gel was significantly more brittle than gels formed with gelatin alone and also noticeably more brittle than gels formed from the glycerol:gelatin solution with a ratio of 1:1.

Solution C—After 3 minutes, a solid, sticky, very elastic gel was formed. This gel was not at all brittle and was not easily separated. This was considered a very significant result as the cross-linked gelatin gel with only glycerol was very brittle. The sorbitol greatly increased the elasticity of an otherwise brittle material. The gel was reheated to 50° C. using a water bath and remained solid, confirming that mTG cross-linking was the mechanism of gelation.

Solution E—Results were very similar to results with glycerol at a ratio of 2:1 glycerol:gelatin: the presence of glycerol resulted in the formation of a much more brittle gel than the gels that are formed by gelatin alone. However, after 3 minutes in the presence of mTG, the gel that was formed was more solid than the gel that is formed by gelatin alone with mTG after 3 minutes.

Solution F—After 3 minutes, a solid yet extremely elastic and sticky gel was formed by mTG cross-linking of the gelatin-sorbitol solution. The sorbitol seemed to have no effect on the mTG cross-linking of gelatin outside of greatly increasing the elasticity and stickiness of the mTG-cross-linked gelatin gels.

From the above it was found that the addition of glycerol to gelatin does not seem to reduce the transition point of gelatin at all. Soaking gelatin in glycerol does not seem to significantly change its propensity for forming thermoreversible gels. The presence of glycerol seems to result in stiffer gels after the gelatin solution has been mixed with mTG for 3 minutes. This may indicate an acceleration of the mTG cross-linking of gelatin when gelatin is in the presence of glycerol.

The presence of high concentrations of glycerol during the mTG cross-linking of gelatin appears to make the resulting cross-linked gels more brittle than gels formed by the cross-linking of gelatin alone. Glycerol does seem to accelerate the mTG cross-linking of gelatin.

The addition of sorbitol in concert with glycerol does not reduce the transition point of gelatin. However, sorbitol greatly increases the elasticity and stickiness of gelatin gels. Sorbitol may be able to be used to increase the elasticity of gelatin gels that are rendered more brittle by the addition of other substances. Sorbitol does not seem to inhibit the mTG cross-linking of gelatin. Though sorbitol seems to slightly increase the transition point of gelatin, it greatly increases the elasticity and stickiness of gelatin gels.

Increasing the glycerol:gelatin ration to 5:1 makes the cross-linked gelatin gels more brittle than those made using a solution of 2:1 glycerol:gelatin but does not have any further effect on the gelatin transition point. The slight cross-linking accelerating effect still occurs at this higher glycerol:gelatin ratio but is not more pronounced than this effect at glycerol:gelatin rations of 1:1 and 2:1.

The solution with a sorbitol:gelatin ratio of 5:1 increases the gelatin transition point but not more than it is increased by the solution with a sorbitol:gelatin ratio of 3:1. However, the cross-linked gelatin gel formed with the 5:1 solution was even more elastic and sticky. This further suggests that the amount of sorbitol can be altered to vary the elasticity of a cross-linked gelatin gel.

Example 13

Effect of Spray Drying on Gelation and Cross Linking of Gelatin

This Example relates to the effect of spray drying on gelatin cross linking. A preferred range for particle size formed by using spray drying is preferably as follows: from about 20 to about 140 μm, more preferably from about 60 to about 100 μm (diameter).

Various strategies for particle formation may optionally be considered. One potential strategy is to form easily reconstitutable particle of gelatin and mTG separately either utilizing specialized drying techniques to this end or by including additives and then drying the gelatin and mTG with additives into particles. Another potential strategy is to form easily reconstitutable particles that incorporate gelatin and mTG together. These particles can be formed just by utilizing specialized drying techniques or by including additives that improve the reconstitutability of these particles. Furthermore, these particles can be created when the gelatin and mTG have not undergone any cross-linking or after they have undergone partial cross-linking.

Materials and Methods

Materials

Type A 300 bloom porcine gelatin was obtained from Sigma-Aldrich corporation (St. Louis, Mo.). Activata TI-WM microbial transglutaminase (mTG) was supplied by Ajinomoto (Japan). Dulbecco's PBS (pH 7.4) was obtained from Biological Industries (Kibbutz Beit HaEmek, Israel). Urea, 98% was obtained by Alfa Aesar (Lancaster, UK).

mTG Solution Preparation:

20% (w/w) microbial transglutaminase (mTG) solution was prepared by dissolving 4 gr of mTG with 16 gr of Dulbecco's PBS. The solution was maintained at room temperature (RT) over the course of the experiment.

4% (w/w) microbial transglutaminase (mTG) solution was prepared by dissolving 2.04 gr of mTG with 50 gr of Dulbecco's PBS. The solution was maintained at room temperature (RT) over the course of the experiment.

Gelatin Solution Preparation:

5% (w/w) gelatin solution was prepared by dissolving 10.52 gr of gelatin powder in 200 gr of Dulbecco's PBS. The mixture was heated to 50° C. and stirred until a homogenous solution was formed. Solution 1 featured 50 ml of 5% gelatin solution. Solution 2—1:1 (w/w) gelatin—mannitol solution was prepared by adding 2.63 gr of mannitol to 50 ml of 5% gelatin solution. The solution was stirred and kept at 50° C. water bath. Throughout the experiment the solution was kept in ~50° C. water dish to prevent thermoreversible gelation.

Solution 3—1:1 (w/w) gelatin-trehalose solution was prepared by dissolving 2.63 gr of trehalose in 50 ml of 5% gelatin solution, while stirring and heating to 50° C. Throughout the experiment the solution was kept at 50° C.

Solution 4—1:1 (w/w) gelatin-urea solution was prepared by dissolving 2.63 gr of urea in 50 ml of 5% gelatin solution, while stirring and heating to 50° C. Throughout the experiment the solution was kept at 50° C.

Solution 5—40 gr of 5% gelatin solution was mixed with 20 gr of 4% mTG solution. Throughout the experiment the solution was kept at 50° C.

Spray Drying of Gelatin Solutions

For the preparation of spray dried gelatin particles, different 5% gelatin solutions in DULBECCO's PBS were prepared (solutions 1-5). Gelatin solutions were spray dried using a BÜCHI micro spray dryer. The flow type is co-current with mixing of air and liquid at the nozzle head. The aspirator rate and inlet temperature were kept constant at 100% and 100° C., respectively. The liquid feed rate was varied according to the process conditions, affecting the outlet temperature as given below.

Solution 1—50 ml of 5% (w/w) gelatin solution was kept heated and spray dried at 15% feed rate, with an outlet temperature of 57° C.

Solution 2—50 ml of 1:1 (w/w) gelatin-mannitol solution was kept soluble in a 50° C. water bath. The liquid feed rate was 15% with an outlet temperature of 62° C.

Solution 3—50 ml of 1:1 (w/w) gelatin-trehalose solution was kept soluble in a 50° C. water bath. The liquid feed rate was 15% with an outlet temperature of 54° C.

Solution 4—50 ml of 1:1 (w/w) gelatin-urea solution was kept soluble in a 50° C. water bath. The liquid feed rate was set to 15% with an outlet temperature of 57° C. Throughout the experiment the liquid feed rate was changed to 20% with an outlet temperature of 54° C., to enable the formation of powder.

Solution 5—40 ml of 5% gelatin solution mixed with 4% mTG solution was spray dried in a 20% liquid feed rate and 56° C. outlet temperature. Throughout the experiment the solution was kept in a 37° C. water dish.

Effect of Spray Drying on Gelation of Gelatin Solutions:

Spray dried gelatin powders were dissolved in 4 ml vials using Dulbecco's PBS and mixed by inverting the tube 4 times. The precipitant solutions were heated at 50° C. water bath and manually mixed, until dissolved. The solutions were then left to cool at RT and the appearance and viscosity of each solution were assessed as the temperature decreased by observation and palpating the solution with a glass rod.

Solution 1—0.33 gr of 5% spray dried gelatin solution was dissolved in 1 ml of RT Dullbeco's PBS, to a final of 25% (w/w) gelatin. Than, another 1 ml of Dulbecco's PBS was added, reducing gelatin content to 12.5% (w/w).

Solution 2—0.33 gr of spray dried 1:1 gelatin-mannitol solution was dissolved in 1 ml of RT Dulbecco's PBS.

Solution 3—0.33 gr of spray dried 1:1 gelatin-trehalose solution was dissolved in 1 ml of RT Dulbecco's PBS.

Solution 4—3 gelatin-urea spray drying failed to produce powder.

Solution 5—0.25 gr of spray dried gelatin-mTG solution was dissolved in 0.75 ml of 37° C. Dulbecco's PBS.

Effect of Spray Drying on Chemical Cross Linking of Gelatin Solutions Using mTG:

Spray dried gelatin powders were dissolved as described in the previous section and kept at 50° C. water bath. 20% of RT mTG solution was added in a 2:1 gelatin to mTG ratio and gently mixed using a pipette tip and by inverting the tube 4 times. Time to gelation was measured and the appearance and viscosity of the solutions after mixture with mTG were assessed by observation and by palpating the solution with a glass rod. When gel was formed it was tested for thermoreversibility by heating the gel to 50° C. using a water bath.

Results:

Spray Drying of Gelatin Solutions

Spray drying of gelatin solutions provided fine white powder in different amounts. Solution 1—~50 ml of 5% gelatin solution provided 0.78 gr. Solution 2—~40 ml of 5% gelatin solution mixed with mannitol in 1:1 ratio (w/w) provided 0.73 gr. Solution 3—~50 ml of 5% gelatin solution mixed with trehalose in a 1:1 ratio (w/w) provided 1.135 gr. Solution 4—no powder was produced. The experiment was terminated since gelatin mixed with urea provided a highly viscous paste that could not be collected. Solution 5—~40 ml of 5% gelatin solution mixed with 4% mTG solution provided 1.27 gr.

Effect of Spray Drying on Gelation of Gelatin Solutions:

Solution 1—gelatin powder partially dissolved in RT PBS to a final 25% (w/w) of gelatin, forming a white non-soluble precipitant. After heating at 50° C. water bath, the powder dissolved, creating a homogenous solution. When cooled to RT, the solution gelled, another 1 ml of PBS was added, to decrease gelatin to 12.5% (w/w). The 12.5% gelatin solution gelled at 26-27° C.

Solution 2—gelatin-mannitol powder partially dissolved in RT PBS to a final ~12.5% (w/w) of gelatin (gelatin is expected to be ½ the amount of the produced powder, yet the accurate percentage of gelatin is unknown). A white non-soluble precipitant was formed. After heating in 50° C. water bath, the powder dissolved, creating a homogenous solution. When cooled to RT, the solution gelled at 28-29° C.

Solution 3—gelatin-trehalose powder partially dissolved in RT PBS to a final ~12.5% (w/w) of gelatin (gelatin is expected to be ½ the amount of the produced powder, yet the accurate percentage of gelatin is unknown). A white non-soluble precipitant was formed. After heating in 50° C. water bath, the powder dissolved, creating a homogenous solution. When cooled to RT, the solution gelled at 25-26° C.

Solution 4—the solution contained a cross-linking agent and therefore was examined for cross-linking rather than gelation.

Effect of Spray Drying on Chemical Cross Linking of Gelatin Solutions Using mTG:

Solution 1—500 ul of 20% mTG solution was added to 2 ml of 12.5% gelatin solution. After 4 min. a strong white gel was formed. The gel was irreversible.

Solution 2—250 ul of 20% mTG solution was added to 1 ml of 12.5% gelatin solution with mannitol. After 2.5 min a strong white gel was formed. The gel was irreversible.

Solution 3—250 ul of 20% mTG solution was added to 1 ml of 12.5% gelatin solution with trehalose. After 3 min a strong white colored gel was formed. The gel was irreversible.

Solution 4—the mTG-gelatin solution was dissolved in 1 ml of Dulbecco's PBS heated to 37° C. A white, weak gel was immediately formed preventing the complete dissolution in PBS. The formed gel was irreversible.

From the above, it appears that spray drying of gelatin solutions is possible. For example, 5% gelatin solutions can be spray dried, producing fine white powders. Gelatin can be spray dried with mannitol and trehalose in 1:1 (w/w) gelatin to mannitol or trehalose ratio. Spray dried gelatin-mannitol solutions have a higher transition point compared to spray dried gelatin alone. Spray dried gelatin-trehalose have a lower transition point compared to spray dried gelatin alone.

Cross linking of spray dried gelatin solutions is possible. Spray drying of 1:1 (w/w) gelatin-mannitol solutions improved cross-linking. Spray drying of 1:1 (w/w) gelatin-trehalose solutions did not affect cross-linking.

Spray drying of gelatin solutions mixed with mTG is possible. The particles formed can immediately form a gel upon reconstitution.

Example 14

Applicator for Applying Sealant

Figure 11A:
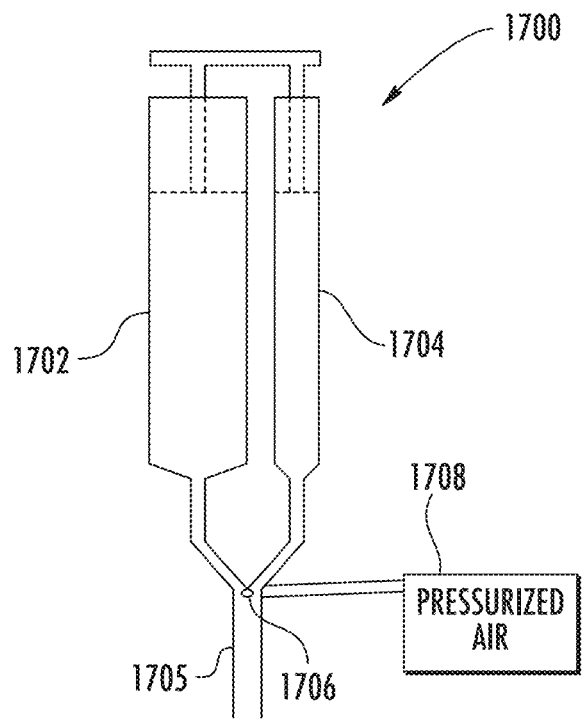
FIGS. 11A and 11B show an example of the double syringe method of application of the two component hemostatic sealant.
Figure 11B:
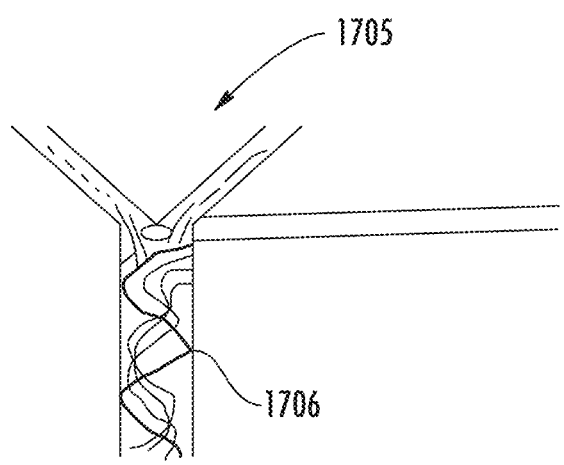

This Example relates to an exemplary, illustrative applicator for applying a hemostatic sealant according to some embodiments of the present invention. FIG. 11A shows an example of a double syringe applicator 1700, featuring two syringes 1702 and 1704, for containing each component of the two component hemostatic sealant. Syringe 1702 may optionally include gelatin or a substitute as described herein, while syringe 1704 may optionally include transglutaminase or a substitute as described herein. The difference in volume of the vials will reflect the related ratio of mixing between the two components. The two components may mix in the nozzle 1705. For improved mixing the nozzle 1705 may contain a whirlpool creating element 1706 (shown in more detail in FIG. 11B). Syringe applicator 1700 may optionally be connected to a pressurized air system 1708 at the nozzle 1705, to create a spray effect. The pressurized air may optionally enter in the proximal or distal end of the nozzle 1705 according to the desired application.

Example 15

Catheter and Method of Use Thereof

Figure 12A:
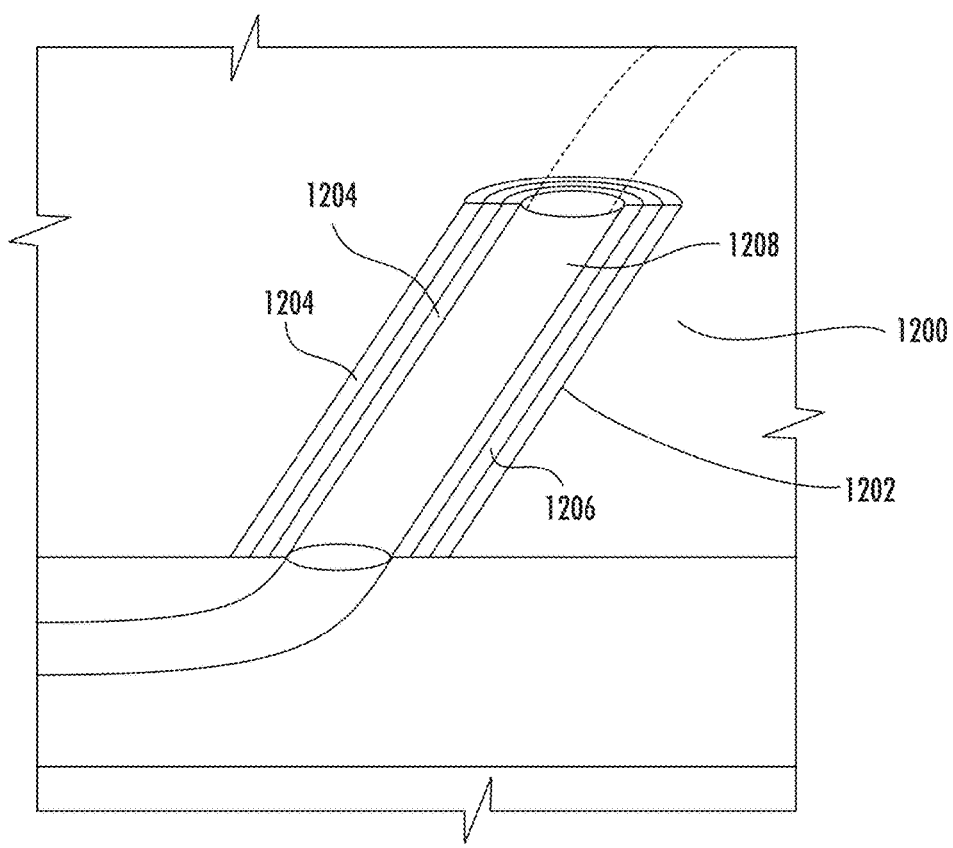
FIGS. 12A and 12B show an example of a vascular insertion point closure where the catheter is covered by the components described herein.

This Example relates to an exemplary, illustrative catheter and method of use thereof according to some embodiments of the present invention. FIG. 12A shows an example of a vascular insertion point closure where a catheter 1200 preferably features a coating 1202, comprising the sealant components described herein. Coating 1202 optionally and preferably features at least one gelatin layer 1204, of which two are shown for the purpose of illustration only and without any intention of being limiting. Gelatin layer 1204 may optionally be substituted by another type of protein substrate as described herein. Coating 1202 also optionally and preferably features at least one transglutaminase layer 1206, which again may optionally be substituted by another cross-linking material as described herein. Coating 1202 is preferably wrapped around an vascular introducer sheath 1208, also referred to as a trocar.

Figure 12B:
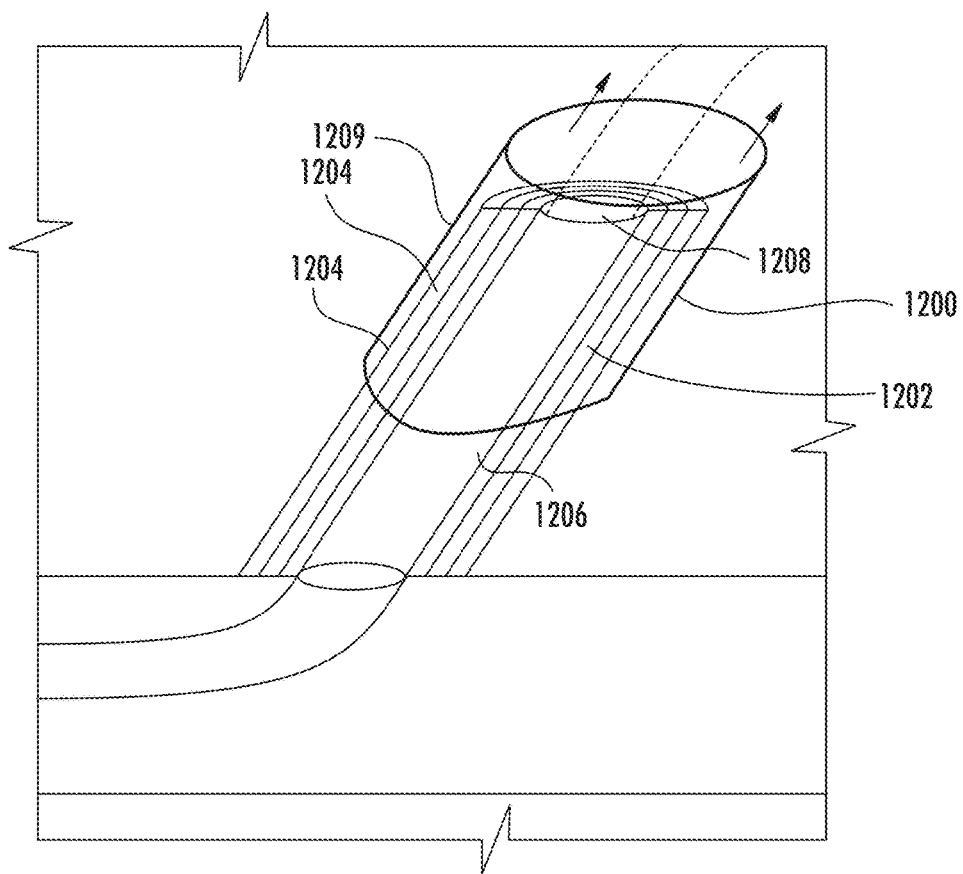

The sheath 1208 may optionally be covered by yet another external sheath 1209 that creates a mechanical barrier between the dry sealant component and the body fluids, as shown in FIG. 12B. Once the external sheath 1209 is removed, the sealant components are activated by the body fluids to create a peri-vascular entry point closure plug.

While the invention has been described with reference to the foregoing detailed description thereof and preferred embodiments, the foregoing description in intended to illustrate and not limit the invention, which is defined by the scope of the included claims. Other aspects, advantages, and modifications are within the scope of those claims.

What is claimed is:

1. A hemostatic or body fluid sealing agent wherein said agent comprises a composition of gelatin and a transglutaminase composition wherein said transglutaminase composition has a specific gelatin crosslinking activity of from 40U to 200 U/gm of gelatin and in which the weight ratio of gelatin to transglutaminase composition is in a range of from 1:1 to 300:1; such that said agent when applied to a wound site cross links between gelatin chains and endogenous collagen of tissue extracellular matrix to create a barrier to fluid leakage or bleeding.

2. The agent according to claim 1, wherein said transglutaminase composition comprises a plant, recombinant, animal, or microbe derived transglutaminase other than blood derived Factor XIII.

3. The agent according to claim 1, wherein said animal origin is selected from the group consisting of fish and mammals.

4. The agent according to claim 1, wherein said microbial derived transglutaminase is isolated from one or more of *Streptoverticillium aldaccii, Streptomyces hygroscopicus*, or *Escherichia coli*.

5. The agent according to claim 1, wherein said composition has a pH in a range of from 5 to 8.

6. The agent according to claim 1, further comprising a stabilizer or a filler.

7. The agent according to claim 1, wherein gelatin is purified to remove salts and wherein said transglutaminase composition comprises a recombinant or animal derived transglutaminase.

8. The agent according to claim 1, wherein said agent induces hemostasis or stasis of other leaking bodily fluids in said tissue.

9. The agent according to claim 1 wherein bodily fluid is selected from the group consisting of blood, cerebral spinal fluid, intestinal fluid, air, bile, and urine.

10. The agent according to claim 1, wherein said agent induces the formation of a biomimetic clot at a site of a damaged blood vessel.

11. The agent according to claim 1, wherein said wounded site is selected from the group consisting of surgically cut tissue and traumatized tissue.

12. A hemostatic or body fluid sealing agent wherein said agent comprises a composition of gelatin and a transglutaminase composition wherein said transglutaminase composition has a specific gelatin crosslinking activity of from 40U to 200 U/gm of gelatin for use in the treatment of wounded tissue, and in which the weight ratio of gelatin to transglutaminase composition is in a range of from 1:1 to 300:1.

* * * * *